US006772012B2

(12) United States Patent
Ricart et al.

(10) Patent No.: US 6,772,012 B2
(45) Date of Patent: Aug. 3, 2004

(54) METHODS FOR ELECTROSURGICAL TREATMENT OF SPINAL TISSUE

(75) Inventors: Olivier Ricart, Dudelange (LU); Jean Woloszko, Mountain View, CA (US); David C. Hovda, Mountain View, CA (US); Hira V. Thapliyal, Los Altos, CA (US); Philip E. Eggers, Dublin, OH (US)

(73) Assignee: ArthroCare Corporation, Sunnyvale, CA (US)

( * ) Notice: Subject to any disclaimer, the term of this patent is extended or adjusted under 35 U.S.C. 154(b) by 0 days.

(21) Appl. No.: 09/848,843

(22) Filed: May 3, 2001

(65) Prior Publication Data

US 2001/0032001 A1 Oct. 18, 2001

Related U.S. Application Data

(63) Continuation-in-part of application No. 09/316,472, filed on May 21, 1999, now Pat. No. 6,264,650, which is a continuation-in-part of application No. 09/295,687, filed on Apr. 21, 1999, now Pat. No. 6,203,542, which is a continuation-in-part of application No. 09/054,323, filed on Apr. 2, 1998, now Pat. No. 6,063,079, which is a continuation-in-part of application No. 09/268,616, filed on Mar. 15, 1999, now Pat. No. 6,159,208, which is a continuation-in-part of application No. 08/990,374, filed on Dec. 15, 1997, now Pat. No. 6,109,268, which is a continuation-in-part of application No. 08/485,219, filed on Jun. 7, 1995, now Pat. No. 5,697,281, application No. 09/848,843, which is a continuation-in-part of application No. 09/026,851, filed on Feb. 20, 1999, which is a continuation-in-part of application No. 08/690,159, filed on Jul. 18, 1996.

(60) Provisional application No. 60/201,459, filed on May 3, 2000.

(51) Int. Cl.⁷ .......................... A61F 7/00; A61B 18/12; A61B 18/14
(52) U.S. Cl. ........................ 607/99; 606/32; 606/41; 607/105; 607/113
(58) Field of Search ........................ 606/32, 41; 607/99, 607/105, 113

(56) References Cited

U.S. PATENT DOCUMENTS

| 2,056,377 A | 10/1936 | Wappler |
| 3,815,604 A | 6/1974 | O'Malley et al. |

(List continued on next page.)

FOREIGN PATENT DOCUMENTS

| DE | 3930451 | 3/1991 | ........... A61B/17/39 |
| EP | 0 703 461 | 3/1996 | ........... G01R/27/02 |

(List continued on next page.)

OTHER PUBLICATIONS

Pearce, John A. (1986) *Electrosurgery*, pp. 17, 69–75, 87, John Wiley & Sons, New York.

(List continued on next page.)

*Primary Examiner*—Lee Cohen
(74) *Attorney, Agent, or Firm*—John T. Raffle; Richard R. Batt

(57) ABSTRACT

Systems, apparatus, and methods for treating spinal tissue and other body structures in open and endoscopic spine surgery to relieve symptoms, such as neck or back pain. In particular, the present invention provides methods for the controlled heating of various tissues in or around the vertebral column, including various interspinous tissues, such that spinal ligaments and cartilage surrounding the vertebrae and the facet joints are shrunk or tightened to stabilize the vertebral column of a patient. Thermal energy is applied to the target tissue in a subablation mode of an electrosurgical system to cause shrinkage of the tissue, thereby stiffening the interspinous tissue and stabilizing the vertebral column. In an exemplary embodiment, a high frequency RF voltage can be applied between one or more active electrode(s) and one or more return electrode(s) to heat a target interspinous tissue to within a temperature range at which irreversible shrinkage of the tissue occurs.

59 Claims, 37 Drawing Sheets

U.S. PATENT DOCUMENTS

| | | |
|---|---|---|
| 3,828,780 A | 8/1974 | Morrison, Jr. et al. |
| 3,901,242 A | 8/1975 | Storz |
| 3,920,021 A | 11/1975 | Hiltebrandt |
| 3,939,839 A | 2/1976 | Curtiss |
| 3,970,088 A | 7/1976 | Morrison |
| 4,040,426 A | 8/1977 | Morrison, Jr. |
| 4,043,342 A | 8/1977 | Morrison, Jr. |
| 4,074,718 A | 2/1978 | Morrison, Jr. |
| 4,092,986 A | 6/1978 | Schneiderman |
| 4,116,198 A | 9/1978 | Roos |
| 4,181,131 A | 1/1980 | Ogiu |
| 4,184,492 A | 1/1980 | Meinke et al. |
| 4,202,337 A | 5/1980 | Hren et al. |
| 4,228,800 A | 10/1980 | Degler, Jr. et al. |
| 4,232,676 A | 11/1980 | Herczog |
| 4,248,231 A | 2/1981 | Herczog et al. |
| 4,326,529 A | 4/1982 | Doss et al. |
| 4,381,007 A | 4/1983 | Doss |
| 4,476,862 A | 10/1984 | Pao |
| 4,532,924 A | 8/1985 | Auth et al. |
| 4,548,207 A | 10/1985 | Reimels |
| 4,567,890 A | 2/1986 | Ohta et al. |
| 4,590,934 A | 5/1986 | Malis et al. |
| 4,593,691 A | 6/1986 | Lindstrom et al. |
| 4,658,817 A | 4/1987 | Hardy |
| 4,660,571 A | 4/1987 | Hess et al. |
| 4,674,499 A | 6/1987 | Pao |
| 4,682,596 A | 7/1987 | Bales et al. |
| 4,706,667 A | 11/1987 | Roos |
| 4,727,874 A | 3/1988 | Bowers et al. |
| 4,765,331 A | 8/1988 | Petruzzi et al. |
| 4,785,823 A | 11/1988 | Eggers et al. |
| 4,805,616 A | 2/1989 | Pao |
| 4,823,791 A | 4/1989 | D'Amelio et al. |
| 4,832,048 A | 5/1989 | Cohen |
| 4,896,671 A | 1/1990 | Cunningham et al. |
| 4,920,978 A | 5/1990 | Colvin |
| 4,931,047 A | 6/1990 | Broadwin et al. |
| 4,936,281 A | 6/1990 | Stasz |
| 4,936,301 A | 6/1990 | Rexroth et al. |
| 4,943,290 A | 7/1990 | Rexroth et al. |
| 4,958,539 A | 9/1990 | Stasz et al. |
| 4,966,597 A | 10/1990 | Cosman |
| 4,967,765 A | 11/1990 | Turner et al. |
| 4,976,709 A | 12/1990 | Sand |
| 4,976,711 A | 12/1990 | Parins et al. |
| 4,979,948 A | 12/1990 | Geddes et al. |
| 4,998,933 A | 3/1991 | Eggers et al. |
| 5,007,908 A | 4/1991 | Rydell |
| 5,009,656 A | 4/1991 | Reimels |
| 5,035,696 A | 7/1991 | Rydell |
| 5,047,026 A | 9/1991 | Rydell |
| 5,047,027 A | 9/1991 | Rydell |
| 5,078,717 A | 1/1992 | Parins et al. |
| 5,080,660 A | 1/1992 | Buelna |
| 5,084,044 A | 1/1992 | Quint |
| 5,085,659 A | 2/1992 | Rydell |
| 5,088,997 A | 2/1992 | Delahuerga et al. |
| 5,098,431 A | 3/1992 | Rydell |
| 5,099,840 A | 3/1992 | Goble et al. |
| 5,108,391 A | 4/1992 | Flachenecker et al. |
| 5,112,330 A | 5/1992 | Nishigaki et al. |
| 5,122,138 A | 6/1992 | Manwaring |
| 5,125,928 A | 6/1992 | Parins et al. |
| 5,137,530 A | 8/1992 | Sand |
| 5,167,659 A | 12/1992 | Ohtomo et al. |
| 5,171,311 A | 12/1992 | Rydell et al. |
| 5,178,620 A | 1/1993 | Eggers et al. |
| 5,190,517 A | 3/1993 | Zieve et al. |
| 5,192,280 A | 3/1993 | Parins |
| 5,195,959 A | 3/1993 | Smith |
| 5,197,466 A | 3/1993 | Marchosky et al. |
| 5,197,963 A | 3/1993 | Parins |
| 5,201,729 A | 4/1993 | Hertzmann et al. |
| 5,207,675 A | 5/1993 | Canady |
| 5,217,457 A | 6/1993 | Delahuerga et al. |
| 5,217,459 A | 6/1993 | Kamerling |
| 5,230,334 A | 7/1993 | Klopotek |
| 5,267,994 A | 12/1993 | Gentelia et al. |
| 5,267,997 A | 12/1993 | Farin et al. |
| 5,273,524 A | 12/1993 | Fox et al. |
| 5,277,201 A | 1/1994 | Stern |
| 5,290,282 A | 3/1994 | Casscells |
| 5,300,069 A | 4/1994 | Hunsberger et al. |
| 5,306,238 A | 4/1994 | Fleenor |
| 5,312,400 A | 5/1994 | Bales et al. |
| 5,314,406 A | 5/1994 | Arias et al. |
| 5,318,564 A | 6/1994 | Eggers |
| 5,324,254 A | 6/1994 | Phillips |
| 5,330,470 A | 7/1994 | Hagen |
| 5,334,140 A | 8/1994 | Phillips |
| 5,342,357 A | 8/1994 | Nardella |
| 5,366,443 A | 11/1994 | Eggers et al. |
| 5,370,675 A | 12/1994 | Edwards et al. |
| 5,374,265 A | 12/1994 | Sand |
| 5,375,588 A | 12/1994 | Yoon |
| 5,380,277 A | 1/1995 | Phillips |
| 5,383,876 A | 1/1995 | Nardella |
| 5,383,917 A | 1/1995 | Desai et al. |
| 5,395,312 A | 3/1995 | Desai |
| 5,403,311 A | 4/1995 | Abele et al. |
| 5,417,687 A | 5/1995 | Nardella et al. |
| 5,419,767 A | 5/1995 | Eggers et al. |
| 5,423,810 A | 6/1995 | Goble et al. |
| 5,423,882 A | 6/1995 | Jackman et al. |
| 5,433,739 A | 7/1995 | Sluijter et al. |
| 5,436,566 A | 7/1995 | Thompson et al. |
| 5,438,302 A | 8/1995 | Goble |
| 5,439,446 A | 8/1995 | Barry |
| 5,441,499 A | 8/1995 | Fritzsch |
| 5,451,224 A | 9/1995 | Goble et al. |
| 5,454,809 A | 10/1995 | Janssen |
| 5,458,596 A * | 10/1995 | Lax et al. ............... 606/41 |
| 5,496,312 A | 3/1996 | Klicek |
| 5,496,314 A | 3/1996 | Eggers |
| 5,496,317 A | 3/1996 | Goble et al. |
| 5,514,130 A * | 5/1996 | Baker ................. 606/41 |
| 5,542,945 A | 8/1996 | Fritzsch |
| 5,556,397 A | 9/1996 | Long et al. |
| 5,562,703 A | 10/1996 | Desai |
| 5,569,242 A | 10/1996 | Lax et al. |
| 5,571,100 A | 11/1996 | Goble et al. |
| 5,584,872 A | 12/1996 | LaFontaine et al. |
| 5,609,151 A | 3/1997 | Mulier et al. |
| 5,633,578 A | 5/1997 | Eggers et al. |
| 5,647,869 A | 7/1997 | Goble et al. |
| 5,660,836 A | 8/1997 | Knowlton |
| 5,662,680 A | 9/1997 | Desai |
| 5,676,693 A | 10/1997 | LaFontaine et al. |
| 5,681,282 A | 10/1997 | Eggers et al. |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,700,262 A | 12/1997 | Acosta et al. |
| 5,720,744 A | 2/1998 | Eggleston et al. |
| 5,725,524 A | 3/1998 | Mulier et al. |
| 5,766,153 A | 6/1998 | Eggers et al. |
| 5,807,395 A | 9/1998 | Mulier et al. |
| 5,810,764 A | 9/1998 | Eggers et al. |

| | | |
|---|---|---|
| 5,810,809 A | 9/1998 | Rydell |
| 5,823,955 A | 10/1998 | Kuck et al. |
| 5,843,019 A | 12/1998 | Eggers et al. |
| 5,846,196 A | 12/1998 | Siekmeyer et al. |
| 5,860,951 A | 1/1999 | Eggers et al. |
| 5,860,975 A | 1/1999 | Goble et al. |
| 5,871,469 A | 2/1999 | Eggers et al. |
| 5,873,855 A | 2/1999 | Eggers et al. |
| 5,885,277 A | 3/1999 | Korth |
| 5,888,198 A | 3/1999 | Eggers et al. |
| 5,891,095 A | 4/1999 | Eggers et al. |
| 5,897,553 A | 4/1999 | Mulier |
| 5,902,272 A | 5/1999 | Eggers et al. |
| 5,944,715 A | 8/1999 | Goble et al. |
| 5,954,716 A * | 9/1999 | Sharkey et al. ............... 606/32 |
| 5,980,504 A | 11/1999 | Sharkey et al. |
| 6,004,319 A | 12/1999 | Goble et al. |
| 6,007,570 A | 12/1999 | Sharkey et al. |
| 6,013,076 A | 1/2000 | Goble et al. |
| 6,015,406 A * | 1/2000 | Goble et al. .................. 606/41 |
| 6,024,733 A | 2/2000 | Eggers et al. |
| 6,027,501 A | 2/2000 | Goble et al. |
| 6,039,734 A | 3/2000 | Goble et al. |
| 6,056,746 A | 5/2000 | Goble et al. |
| 6,063,079 A | 5/2000 | Hovda et al. |
| 6,066,134 A | 5/2000 | Eggers et al. |
| 6,068,628 A * | 5/2000 | Fanton et al. .................. 606/41 |
| 6,073,051 A | 6/2000 | Sharkey et al. |
| 6,074,386 A | 6/2000 | Goble et al. |
| 6,090,106 A | 7/2000 | Goble et al. |
| 6,093,186 A | 7/2000 | Goble et al. |
| 6,102,046 A | 8/2000 | Weinstein et al. |
| 6,109,268 A | 8/2000 | Thapliyal et al. |
| 6,117,109 A | 9/2000 | Eggers et al. |
| 6,126,682 A | 10/2000 | Sharkey et al. |
| 6,142,992 A | 11/2000 | Cheng et al. |
| 6,149,620 A | 11/2000 | Baker et al. |
| 6,159,194 A | 12/2000 | Eggers et al. |
| 6,159,208 A | 12/2000 | Hovda et al. |
| 6,168,593 B1 | 1/2001 | Sharkey et al. |
| 6,179,824 B1 | 1/2001 | Eggers et al. |
| 6,179,836 B1 | 1/2001 | Eggers et al. |
| 6,183,469 B1 | 2/2001 | Thapliyal et al. |
| 6,190,381 B1 | 2/2001 | Olsen et al. |
| 6,203,542 B1 | 3/2001 | Ellsberry et al. |
| 6,210,402 B1 | 4/2001 | Olsen et al. |
| 6,224,592 B1 | 5/2001 | Eggers et al. |
| 6,228,081 B1 | 5/2001 | Goble |
| 6,235,020 B1 | 5/2001 | Cheng et al. |
| 6,238,391 B1 | 5/2001 | Olsen et al. |
| 6,254,600 B1 | 7/2001 | Willink et al. |
| 6,261,286 B1 | 7/2001 | Goble et al. |
| 6,261,311 B1 | 7/2001 | Sharkey et al. |
| 6,264,652 B1 | 7/2001 | Eggers et al. |
| 6,277,112 B1 | 8/2001 | Underwood et al. |
| 6,293,942 B1 | 9/2001 | Goble et al. |
| 6,296,636 B1 | 10/2001 | Cheng et al. |
| 6,296,638 B1 | 10/2001 | Davison et al. |
| 6,306,134 B1 | 10/2001 | Goble et al. |
| 6,312,408 B1 | 11/2001 | Eggers et al. |
| 6,319,250 B1 | 11/2001 | Falwell et al. |
| 6,322,549 B1 | 11/2001 | Eggers et al. |
| 6,355,032 B1 | 3/2002 | Hovda et al. |
| 6,363,937 B1 | 4/2002 | Hovda et al. |
| 6,379,351 B1 | 4/2002 | Thapliyal et al. |
| 6,391,025 B1 | 5/2002 | Weinstein et al. |
| 6,416,507 B1 | 7/2002 | Eggers et al. |
| 6,416,508 B1 | 7/2002 | Eggers et al. |
| 6,432,103 B1 | 8/2002 | Ellsberry et al. |
| 6,500,173 B2 * | 12/2002 | Underwood et al. .......... 606/32 |
| 6,530,922 B2 | 3/2003 | Cosman |
| 6,575,968 B1 | 6/2003 | Eggers et al. |
| 6,602,248 B1 | 8/2003 | Sharps et al. |
| 2002/0029036 A1 | 3/2002 | Goble et al. |

FOREIGN PATENT DOCUMENTS

| | | | |
|---|---|---|---|
| EP | 0 740 926 A2 | 11/1996 | ........... A61B/17/39 |
| EP | 0 754 437 | 1/1997 | ........... A61B/17/39 |
| EP | 515867 | 7/1999 | |
| EP | 0 694 290 | 11/2000 | ........... A61B/18/04 |
| FR | 2313949 | 1/1977 | ........... A61N/3/02 |
| GB | 2 308 979 | 7/1997 | ........... A61B/17/36 |
| GB | 2 308 980 | 7/1997 | ........... A61B/17/36 |
| GB | 2 308 981 | 7/1997 | ........... A61B/17/36 |
| GB | 2 327 350 | 1/1999 | ........... A61B/17/39 |
| GB | 2 327 351 | 1/1999 | ........... A61B/17/39 |
| GB | 2 327 352 | 1/1999 | ........... A61B/17/39 |
| JP | 57-57802 | 4/1982 | ........... A61B/1/00 |
| JP | 57-117843 | 7/1982 | ........... A61B/17/39 |
| WO | 90/03152 | 4/1990 | ........... A61B/17/39 |
| WO | WO 90/07303 | 7/1990 | ........... A61B/17/39 |
| WO | 92/21278 | 12/1992 | ............ A61B/5/04 |
| WO | WO 93/13816 | 7/1993 | ........... A61B/17/36 |
| WO | 93/20747 | 10/1993 | ............ A61B/5/00 |
| WO | WO 94/04220 | 3/1994 | ............ A61N/1/06 |
| WO | 94/08654 | 4/1994 | ......... A61M/37/00 |
| WO | 94/14383 | 7/1994 | |
| WO | WO 95/34259 | 12/1995 | ............ A61F/5/48 |
| WO | 96/00042 | 1/1996 | ........... A61B/17/39 |
| WO | 97/00646 | 1/1997 | ........... A61B/17/39 |
| WO | 97/00647 | 1/1997 | ........... A61B/17/39 |
| WO | 97/24073 | 7/1997 | ........... A61B/17/39 |
| WO | WO 97/24074 | 7/1997 | ........... A61B/17/39 |
| WO | 97/24993 | 7/1997 | ........... A61B/17/39 |
| WO | 97/24994 | 7/1997 | ........... A61B/17/39 |
| WO | 97/249992 | 7/1997 | |
| WO | 97/48345 | 12/1997 | ........... A61B/17/39 |
| WO | 97/48346 | 12/1997 | ........... A61B/17/39 |
| WO | 98/01087 | 1/1998 | |
| WO | 98/07468 | 2/1998 | ............ A61N/1/40 |
| WO | 98/11944 | 3/1998 | |
| WO | 98/17190 | 4/1998 | |
| WO | 98/27879 | 7/1998 | ........... A61B/17/36 |
| WO | 98/27880 | 7/1998 | ........... A61B/17/39 |
| WO | 99/47058 | 9/1999 | |
| WO | 99/51155 | 10/1999 | ........... A61B/17/36 |
| WO | 99/51158 | 10/1999 | ........... A61B/17/39 |

OTHER PUBLICATIONS

J.W. Ramsey et al. *Urological Research* vol. 13, pp. 99–102 (1985).

V.E. Elsasser et al. *Acta Medicotechnica* vol. 24, No. 4, pp. 129–134 (1976).

P.C. Nardella (1989) *SPIE* 1068:42–49 Radio Frequency Energy and Impedance Feedback.

R. Tucker et al., Abstract P14–11, p. 248, "A Bipolar Electrosurgical Turp Loop".

R. Tucker et al. *J. of Urology* vol. 141, pp. 662–665, (1989).

R. Tucker et al. *Urological Research* vol. 18, pp. 291–294 (1990).

Kramolowsky et al. *J. of Urology* vol. 143, pp. 275–277 (1990).

Kramolowsky et al. *J. of Urology* vol. 146, pp. 669–674 (1991).

Slager et al. *Z. Kardiol.* 76:Suppl. 6, 67–71 (1987).

Slager et al. *JACC* 5 (6) :1382–6 (1985).

Olsen MD, Bipolar Laparoscopic Cholecstectomy Lecture (marked confidential), Oct. 7, 1991.

Codman & Shurtleff, Inc. "The Malis Bipolar Electrosurgical System CMC–III Instruction Manual" Jul. 1991.

Valley Forge's New Products, CLINICA, 475, 5, Nov. 6, 1991.

Valley Forge Scientific Corp., "Summary of Safety and Effective Information from 510K," 1991.

Codman & Shurtleff, Inc. "The Malis Bipolar Coagulating and Bipolar Cutting System CMC–II" brochure, early 1991.

L. Malis, "The Value of Irrigation During Bipolar Coagulation" See ARTC 21602, early Apr. 9, 1993.

L. Malis, "Excerpted from a seminar by Leonard I. Malis, M.D. at the 1995 American Association of Neurological Surgeons Meeting," 1995.

L. Malis, "Electrosurgery, Technical Note," *J. Neursurg.*, vol. 85, 970–975, 11/96.

Ian E. Shuman, "Biopolar Versus Monopolar Electrosurgery: Clinical Applications," *Dentistry Today*, vol. 20, No. 12, 12/01.

Protell et al., "Computer–Assisted Electrocoagulation: Bipolar v. Monoplar in the Treatment of Experimental Canine Gastric Ulcer Bleeding," *Gastroenterology* vol. 80, No. 3, pp. 451–455.

Cook and Webster, "Therapeutic Medical Devices: Application and Design," 1982.

Valleylab SSE2L Instruction Manual, Jan. 6, 1983.

Robert D. Tucker et al., "Demodulated Low Frequency Currents from Electrosurgical Procedures," *Surgery, Gynecology and Obstetrics*, 159:39–43, 1984.

Lu, et al., "Electrical Thermal Anioplasty: Catheter Design Features, In Virtro Tissue Ablation Studies and In Vito Experimental Findings," *Am J. Cardiol* vol. 60, pp. 1117–1122.

Selikowitz & LaCourse, "Electric Current and Voltage Recordings on the Myocardium During Electrosurgical Procedures in Canines," *Surgery, Gynecology & Obstetrics*, vol. 164, 219–224, Mar. 1987.

J. O'Malley, Schaum's Outline of Theory and Problems of Basic Circuit Analysis, McGraw–Hill, $2^{nd}$ Ed., 1992, pp. 3–5.

Arnaud Wattiez et al., "Electrosurgery in Operative Endoscopy," Electrosurgical Effects, Blackwell Science, pp. 85–93, 1995.

Leslie A. Geddes, "Medical Device Accidents: With Illustrative Cases" CRC Press, 1998.

Wyeth, "Electrosurgical Unit" pp. 1181–1202.

C.P. Swain, et al., *Gut* vol. 25, pp. 1424–1431 (1984).

Piercey et al., *Gastroenterology* vol. 74 (3), pp. 527–534 (1978).

A.K. Dobbie *Bio–Medical Engineering* vol. 4, pp. 206–216 (1969).

B. Lee et al. JACC vol. 13 (5), pp. 1167–1175 (1989).

K. Barry et al. *American Heart Journal* vol. 117, pp. 332–341 (1982).

W. Honig *IEEE* pp. 58–65 (1975).

Jacob Kline, *Handbook of Biomedical Engineering*, Academic Press Inc., N.Y., pp. 98–113, 1988.

M.B. Dennis et al. "Evolution of Electrofulguration in Control of Bleeding of Experimental Gastric Ulcers," Digestive Diseases and Sciences, vol. 24, No. 11, 845–848.

Letter from Department of Health to Jerry Malis dated Apr. 15, 1985.

Letter from Jerry Malis to FDA dated Jul. 25, 1985.

Letter from Department of Health to Jerry Malis dated Apr. 22, 1991.

Leonard Malis, "Instrumenation for Microvascular Neurosurgery" *Cerebrovascular Surgery*, vol. 1, 245–260, 1985.

Saal, J., Thermal Characteristics and the Lumbar Disc, NASS, APS First Joint Meeting, Apr. 1998.

* cited by examiner

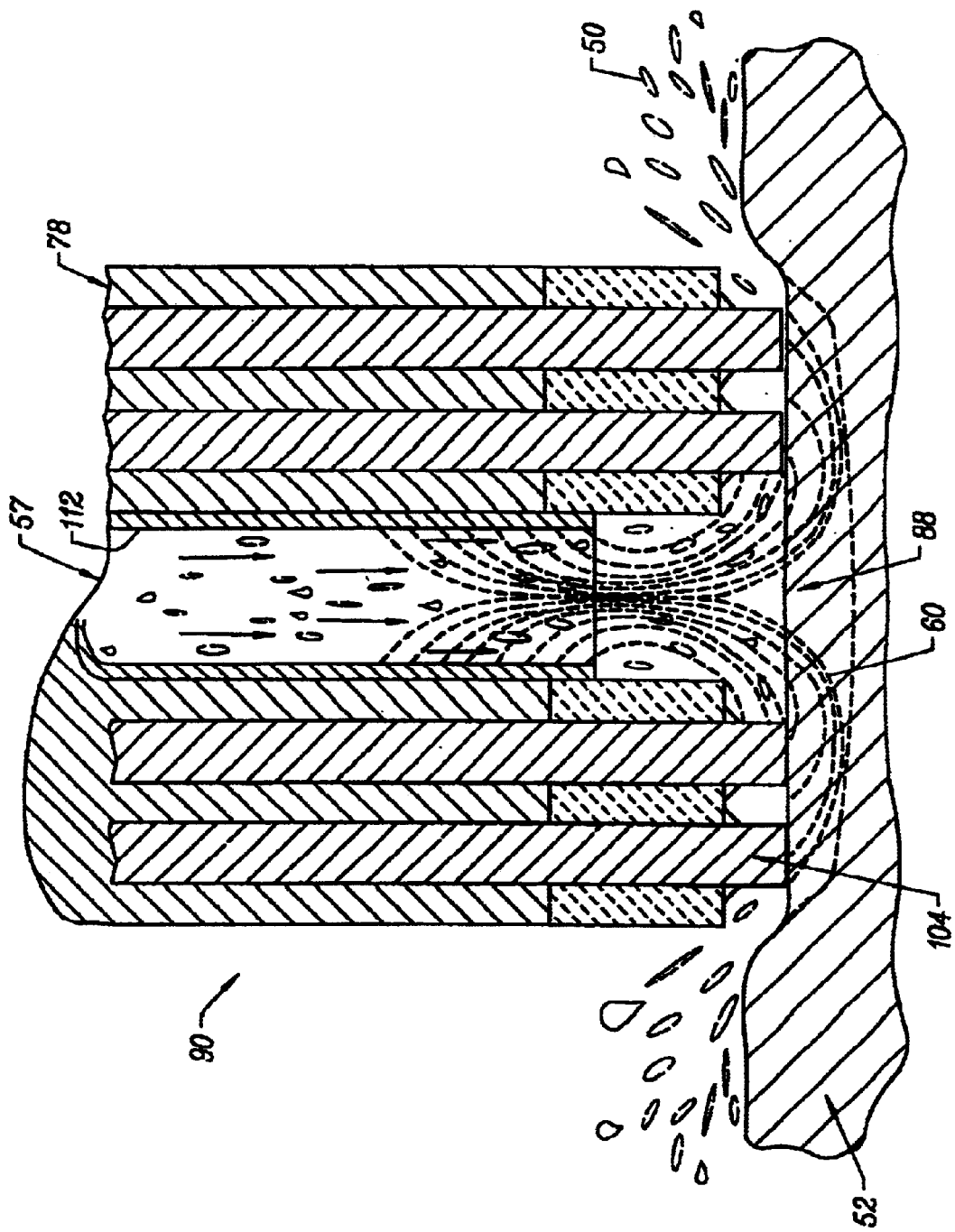

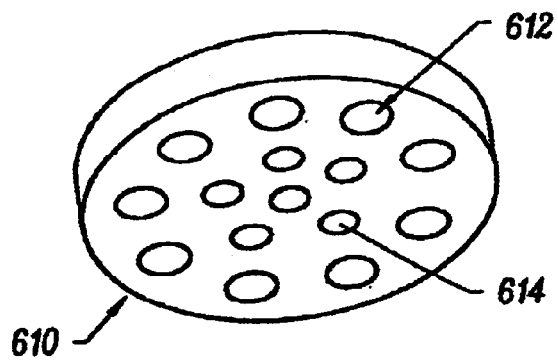
FIG. 13A
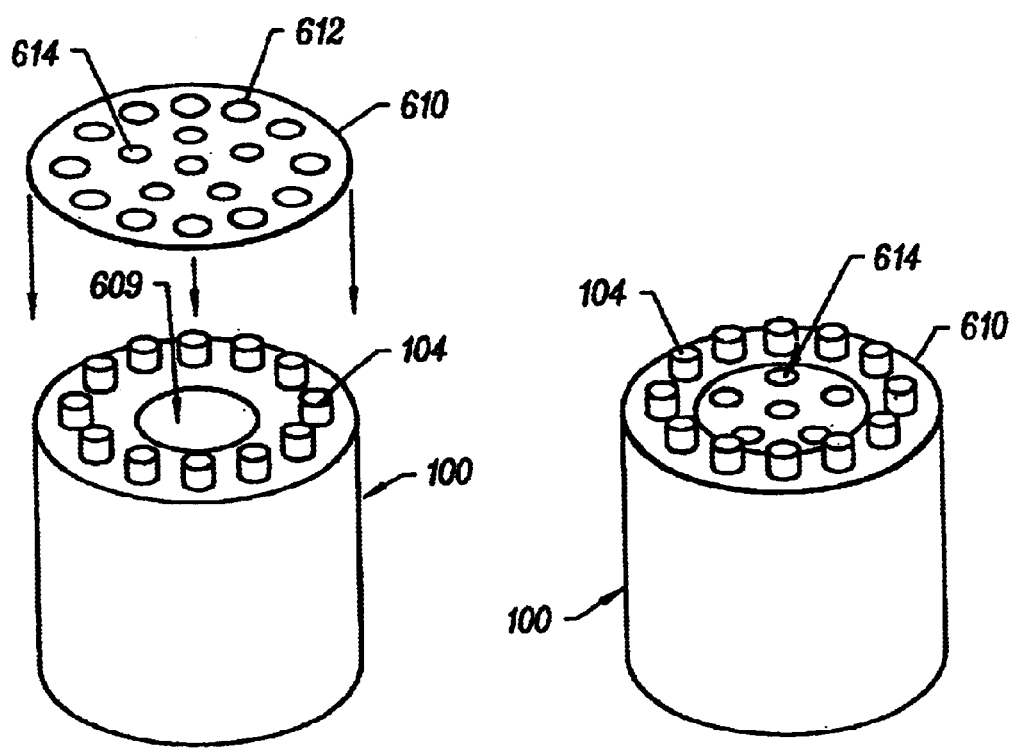
FIG. 13B
FIG. 13C

METHODS FOR ELECTROSURGICAL TREATMENT OF SPINAL TISSUE

RELATED APPLICATIONS

The present invention claims priority from U.S. Provisional Patent Application No. 60/201,459 filed May 3, 2000, and the present invention is a continuation-in-part of U.S. patent application Ser. No. 09/316,472, filed May 21, 1999 now U.S. Pat. No. 6,264,650, which is a continuation-in-part of U.S. patent application Ser. No. 09/295,687, filed Apr. 21, 1999 now U.S. Pat. No. 6,203,542 and U.S. patent application Ser. No. 09/054,323 now U.S. Pat. No. 6,063,079 and Ser. No. 09/268,616 now U.S. Pat. No. 6,159,208 filed Apr. 2, 1998 and Mar. 15, 1999, respectively, each of which is a continuation-in-part of U.S. patent application Ser. No. 08/990,374, filed Dec. 15, 1997 now U.S. Pat. No. 6,109,268, which is a continuation-in-part of U.S. Patent application Ser. No. 08/485,219, filed on Jun. 7, 1995 now U.S. Pat. No. 5,697,281, the complete disclosures of which are incorporated herein by reference for all purposes. This application is also a continuation-in-part of U.S. patent application Ser. No. 09/026,851, filed Feb. 20, 1999, which is a continuation-in-part of U.S. patent application Ser. No. 08/690,159, filed Jul. 18, 1996, the complete disclosure of which is incorporated herein by reference for all purposes.

The present invention is related to commonly assigned co-pending U.S. patent application Ser. No. 09/181,926, filed Oct. 28, 1998, U.S. patent application Ser. No. 09/130,804, filed Aug. 7, 1998, U.S. patent application Ser. No. 09/058,571, filed on Apr. 10, 1998, U.S. patent application Ser. No. 09/248,763, filed Feb. 12, 1999, U.S. patent application Ser. No. 09/026,698, filed Feb. 20, 1998, U.S. patent application Ser. No. 09/074,020, filed on May 6, 1998, U.S. patent application Ser. No. 09/010,382, filed Jan. 21, 1998, U.S. patent application Ser. No. 09/032,375, filed Feb. 27, 1998, U.S. patent application Ser. No. 08/977,845, filed on Nov. 25, 1997, Ser. No. 08/942,580, filed on Oct. 2, 1997, U.S. patent application Ser. No. 08/753,227, filed on Nov. 22, 1996, U.S. patent application Ser. No. 08/687,792, filed on Jul. 18, 1996, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application Ser. No. 07/817,575, filed on Jan. 7, 1992, the complete disclosures of which are incorporated herein by reference for all purposes. The present invention is also related to commonly assigned U.S. Pat. No. 5,697,882, filed Nov. 22, 1995, the complete disclosure of which is incorporated herein by reference for all purposes.

BACKGROUND OF THE INVENTION

The present invention relates generally to the field of electrosurgery, and more particularly to surgical devices and methods which employ high frequency electrical energy to treat tissue in regions of the spine. The present invention is particularly suited for the treatment of the discs, cartilage, ligaments, and other tissues within or around the vertebral column.

The major causes of persistent, often disabling, back pain are disruption of the disc annulus fibrosus, chronic inflammation of the disc (e.g., herniation), or relative instability of the vertebral bodies surrounding a given disc, such as the instability that often occurs due to a stretching of the interspinous tissue surrounding the vertebrae. Intervertebral discs mainly function to cushion and tether the vertebrae, while the interspinous tissue including various ligaments, tendons and cartilage, and the like) functions to support the vertebrae so as to provide flexibility and stability to the patient's spine.

Spinal discs comprise a central hydrostatic cushion, the nucleus pulposus, surrounded by a multi-layered fibrous ligament, the annulus fibrosus. As discs degenerate, they lose their water content and height, bringing the adjoining vertebrae closer together. This results in a weakening of the shock absorption properties of the disc and a narrowing of the nerve openings of the vertebral column which may lead to pinching of the nerve or nerve root. This disc degeneration can eventually cause back and leg pain. Weakness in the annulus from degenerative discs or disc injury can allow fragments of nucleus pulposus to migrate into the annulus fibrosus or spinal canal. There, displaced nucleus fibrosus or protrusion of annulus fibrosus, e.g., herniation, may impinge on spinal nerves. The mere proximity of the nucleus pulposus or a damaged annulus to a nerve can cause direct pressure against the nerve, resulting in pain and sensory and motor deficit.

Often, inflammation from disc herniation can be treated successfully by non-surgical means, such as rest, therapeutic exercise, oral anti-inflammatory medications or epidural injection of corticosteroids. In some cases, the disc tissue is irreparably damaged, thereby necessitating removal of a portion of the disc or the entire disc to eliminate the source of inflammation and pressure. In more severe cases, the adjacent vertebral bodies must be stabilized following excision of the disc material to avoid recurrence of the disabling back pain. One approach to stabilizing the vertebrae, termed spinal fusion, is to insert an interbody graft or implant into the space vacated by the degenerative disc. In this procedure, a small amount of bone may be grafted and packed into the implants. This allows the bone to grow through and around the implant, fusing the vertebral bodies and preventing re-occurrence of the symptoms.

In addition to degenerative discs, many patients have interspinous tissue that has become loose or stretched. Unfortunately, once such tissue has become stretched, it stays stretched. The stretched tissues do not hold the adjacent vertebrae in a stable configuration and allow the vertebrae to separate and "float" within the vertebral column. The unstable vertebrae can impinge on surrounding nerves and cause the patient pain. Consequently, even if a patient's discs have been surgically repaired, the patient may still feel pain if there is excessive mobility in their vertebral column.

Until recently, surgical spinal procedures resulted in major operations including traumatic dissection of muscle, and bone removal or bone fusion. To overcome the disadvantages of traditional traumatic spine surgery, minimally invasive spine surgery was developed. In endoscopic spinal procedures, the spinal canal is not violated and therefore epidural bleeding with ensuing scarring is minimized or completely avoided. In addition, the risk of increased instability due to ligament and bone removal is generally lower in endoscopic procedures than with open procedures. Further, minimally invasive procedures allow more rapid rehabilitation, facilitating faster recovery and return to work.

Minimally invasive techniques for the treatment of spinal diseases or disorders include chemonucleolysis, laser techniques, and mechanical techniques. These procedures generally require the surgeon to form a passage or operating corridor from the external surface of the patient to the spinal disc(s) for passage of surgical instruments, implants and the like. Typically, the formation of this operating corridor requires the removal of soft tissue, muscle or other types of tissue depending on the procedure (e.g., laparascopic, thoracoscopic,). This tissue is usually removed with mechanical instruments, such as pituitary rongeurs, curettes, graspers, cutters, drills, microdebriders and the like. Unfortunately, these mechanical instruments greatly lengthen and increase the complexity of the procedure. In addition, these instruments might sever blood vessels within this tissue, usually causing profuse bleeding that obstructs the surgeon's view of the target site.

Once the operating corridor is established, the nerve root is retracted and a portion or all of the disc is removed with mechanical instruments, such as a pituitary rongeur. In addition to the above problems with mechanical instruments, there are serious concerns because these instruments are not precise, and it is often difficult, during the procedure, to differentiate between the target disc tissue, and other structures within the spine, such as bone, cartilage, ligaments, nerves and non-target tissue. Thus, the surgeon must be extremely careful to minimize damage to the cartilage, ligaments, and bone of the spine, and to avoid damaging nerves, such as the spinal nerves and the dura mater surrounding the spinal cord.

Lasers were initially considered ideal for spine surgery because lasers ablate or vaporize tissue with heat, which also acts to cauterize and seal the small blood vessels in the tissue. Unfortunately, lasers are both expensive and somewhat tedious to use in these procedures. Another disadvantage with lasers is the difficulty in judging the depth of tissue ablation. Since the surgeon generally points and shoots the laser without contacting the tissue, he or she does not receive any tactile feedback to judge how deeply the laser is cutting. Because healthy tissue, bones, ligaments and spinal nerves often lie within close proximity of the spinal disc, it is essential to maintain a minimum depth of tissue damage, which cannot always be ensured with a laser.

Monopolar and bipolar radiofrequency (RF) devices have been used in limited roles in spine surgery, such as to cauterize severed vessels to improve visualization. Monopolar devices, however, suffer from the disadvantage that the electric current will flow through undefined paths in the patient's body, thereby increasing the risk of undesirable electrical stimulation to portions of the patient's body. In addition, since the defined path through the patient's body has a relatively high impedance (because of the large distance or resistivity of the patient's body), large voltage differences must typically be applied between the return and active electrodes in order to generate a current suitable for ablation or cutting of the target tissue. This current, however, may inadvertently flow along paths within the patient's body having less impedance than the defined electrical path, which will substantially increase the current flowing through these paths, possibly causing damage to or destroying surrounding tissue or neighboring peripheral nerves.

Other disadvantages of conventional RF devices, particularly monopolar devices, is nerve stimulation and interference with nerve monitoring equipment in the operating room. In addition, these devices typically operate by creating a voltage difference between the active electrode and the target tissue, causing an electrical arc to form across the physical gap between the electrode and tissue. At the point of contact of the electric arcs with tissue, rapid tissue heating occurs due to high current density between the electrode and tissue. This high current density causes cellular fluids to rapidly vaporize into steam, thereby producing a "cutting effect" along the pathway of localized tissue heating. Thus, the tissue is parted along the pathway of evaporated cellular fluid, inducing undesirable collateral tissue damage in regions surrounding the target tissue site. This collateral tissue damage often causes indiscriminate destruction of tissue, resulting in the loss of the proper function of the tissue. In addition, the device does not remove any tissue directly, but rather depends on destroying a zone of tissue and allowing the body to eventually remove the destroyed tissue.

Thus, there is a need for apparatus and methods for electrosurgical treatment of tissues of the vertebral column, wherein damage to tissues in the region of the spine is minimal or non-existent. There is a further need for apparatus and methods for shrinking stretched interspinous tissues, including ligaments, by the controlled direct or indirect application of thermal energy to targeted interspinous tissues, wherein excessive mobility in the vertebral column is decreased and symptoms are alleviated. The instant invention provides such apparatus and methods, as is described in enabling detail hereinbelow.

SUMMARY OF THE INVENTION

The present invention provides systems, apparatus, and methods for selectively applying electrical energy to structures within a patient's body, such as support tissue within or around the spinal column. The systems and methods of the present invention are useful for shrinkage, ablation, resection, aspiration, and/or hemostasis of tissue and other body structures in open and less-invasive spine surgery. In particular, the present invention includes apparatus and methods for the controlled shrinking of interspinous tissue, in which such tissue is treated with thermal energy to cause the tissue to shrink, thereby stiffening the interspinous tissue structure and stabilizing the vertebral column.

In one aspect of the invention, a method is disclosed for treating herniated discs that exhibit progressive instability. In this procedure, the surgeon performs a discectomy with an electrosurgical probe through a small, one to two inch incision in the patient. The surgeon then applies sufficient voltage to the electrode(s) on the probe to shrink the capsule surrounding the posterior facet joints, which enables rotation, thereby tightening the joint, potentially reducing pain, and providing increased stability. This less invasive technique combines the advantages of spine surgery with the traditional clinical benefits of ArthroCare's Coblation technology (ArthroCare Corporation, Sunnyvale, Calif.). Such clinical benefits include reduced thermal injury, potentially less pain, and faster healing for the patient.

In another aspect, the present invention provides a method of treating interspinous tissue. The method includes positioning one or more active electrode(s) adjacent a target interspinous tissue, and applying high frequency voltage between the active electrode(s) and one or more return electrode(s) to heat and shrink at least a portion of the tissue. The high frequency voltage effects a controlled depth of thermal heating of the tissue to shrink and stiffen the interspinous tissue, thereby at least partially stabilizing the vertebrae and potentially relieving neck or back pain.

In another exemplary embodiment, an electrically conductive media, such as isotonic saline or an electrically conductive gel, is delivered to the target site within the spine to substantially surround the active electrode(s) with the conductive media. The conductive media may be delivered through an instrument to the specific target site, or the entire target region may be filled with conductive media such that the active electrode(s) are submerged during the procedure. Alternatively, the distal end of the instrument may be dipped or otherwise applied to the conductive media prior to introduction into the patient's body. In all of these embodiments, the electrically conductive media is applied or delivered such that it provides a current flow path between the active and return electrode(s). In other embodiments, electrically conductive fluid naturally present in the patient's tissue may be used as a substitute for, or as a supplement to, the electrically conductive media that is applied or delivered to the target site In still another aspect, the present invention provides a method for treating tissue in the vicinity of a facet joint between adjacent vertebrae. The method comprises positioning one or more active electrode(s) adjacent to the tissue in the vicinity of the facet joint. A high frequency voltage difference is applied between the active electrode and a return electrode so as to shrink the tissue in the vicinity of the facet joint thereby stiffening the joint between the adjacent vertebrae. Systems according to the present invention generally include an electrosurgical instrument having a probe or catheter shaft with proximal and distal ends, an electrode assembly at the distal end, and one or more connectors coupling the electrode assembly to a source of high frequency electrical energy. The probe or catheter may assume a wide variety of configurations, with the primary purpose being to introduce the electrode assembly to the patient's spine (in an open or endoscopic procedure) and to permit the treating physician to manipulate the electrode assembly from a proximal end of the shaft. The electrode assembly includes one or more active electrode(s) configured for tissue ablation and a return electrode spaced from the active electrode(s) either on the instrument shaft or separate from the instrument shaft.

The system further includes a power source coupled to the electrodes on the instrument shaft for applying a high frequency voltage between the active and return electrodes. In one embodiment, the system comprises a voltage reduction element coupled between the power source and active electrode to control the voltage delivered to the active electrode. The voltage reduction element will typically comprise a passive element, such as a capacitor, resistor, inductor, or the like. In the representative embodiment, the power supply can apply a voltage of about 150 volts RMS to 600 volts RMS between the active and return electrodes, but the voltage reduction element will reduce this voltage to about 20 volts RMS to 300 volts RMS to the active electrode. In this manner, the voltage delivered to the active electrode is below the threshold for ablation of tissue, but high enough to sufficiently heat and shrink the tissue.

The active electrode(s) may comprise a single active electrode, or an electrode array, extending from an electrically insulating support member, typically made of a inorganic material such as a ceramic, a polyimide, a silicone rubber, or a glass. The active electrode will usually have a smaller exposed surface area than the return electrode, such that the current densities are much higher at the active electrode than at the return electrode. Preferably, the return electrode has a relatively large, smooth surface extending around the instrument shaft to reduce current densities, thereby minimizing damage to adjacent nontarget tissue.

The apparatus may further include a fluid delivery element for delivering electrically conductive fluid to the active electrode(s) and the target site. The fluid delivery element may be located on the instrument, e.g., a fluid lumen or tube, or it may be part of a separate instrument. Alternatively, an electrically conductive gel or spray, such as a saline electrolyte or other conductive gel, may be applied to the electrode assembly or the target site by other means. In this embodiment, the apparatus may not have a fluid delivery element. In both embodiments, the electrically conductive fluid will preferably generate a current flow path between the active electrode(s) and the return electrode(s).

In another aspect, the present invention provides a method of using an electrosurgical system for treating a defect or disorder of an intervertebral column of a patient, wherein the electrosurgical system includes a power supply coupled to at least one active electrode disposed on a shaft distal end of an electrosurgical probe or catheter. Such defects and disorders include excessive mobility or instability in the vertebral column, which may be associated with excessively loose facet joints between adjacent vertebrae. Excessive mobility or instability of the vertebral column may be due to stretched or loose interspinous tissue, such as various ligaments, which surrounds or lies between the spinous process, the superior articular processes, the inferior articular process, or the transverse processes of the vertebrae. In one aspect, a method for treating the spine involves positioning the shaft distal end such that the at least one active electrode is in the vicinity of the tissue targeted for treatment (interspinous ligament, etc.), and thereafter applying a high frequency voltage between the at least one active electrode and at least one return electrode in a subablation mode, such that the tissue targeted for treatment undergoes shrinkage due to controlled thermal heating. Typically, the controlled heating involves elevating the temperature of the target tissue to a temperature in the range of 45° to 90° C., more typically 60° to 70° C. Elevation of the temperature of the targeted tissue within the latter range is particularly suited to effecting shrinkage of collagen fibers of the target tissue. As a result of such treatment, the interspinous tissue shrinks or contracts, typically resulting in increased stability to the spine and concomitant alleviation of symptoms.

In one embodiment, there is provided an electrosurgical system for treating the spine of a patient, the system including a probe having at least one active electrode coupled to a high frequency power supply. The power supply is adapted for applying a suitable high frequency voltage between the at least one active electrode and a return electrode. In one aspect, the system is adapted for toggling between an ablation mode in which a relatively high voltage is applied between the active and return electrodes, and a subablation mode (e.g., thermal heating mode) in which a lower voltage is applied between the active and return electrodes. The subablation mode provides controlled heating of target tissue within a defined temperature range suitable for substantially irreversible shrinkage of target tissue. In one aspect, the system can be readily toggled between the ablation and subablation modes by an operator of the system using a convenient actuator, such as a hand- or foot-operated switch.

In one embodiment, treatment of interspinous tissue to increase stability of the spine may be combined with electrosurgical treatment of a defective intervertebral disc (e.g., ablation, coagulation, or contraction of disc tissue), and/or with an epidural steroid injection. In one embodiment, a method for treating a defective disc or an interspinous tissue involves advancing the shaft distal end of the probe through an introducer needle, with or without an introducer extension tube, towards the target tissue. The use of an introducer needle and introducer extension tube may facilitate positioning the shaft distal end in relation to the tissue targeted for treatment. In one embodiment, the shaft may be positioned, steered, or guided to a target site or tissue under fluoroscopy. Treatment of interspinous tissue according to the invention may be performed in a percutaneous procedure using a posterior lateral approach.

In one aspect, the interspinous tissue may be treated and shrunk using an electrosurgical catheter or probe having a bendable or pre-bent shaft. After introducing the shaft into an appropriate region of the spine, the shaft distal end of such an instrument may be precisely guided to one or more target sites (e.g., interspinous tissue) by a combination of axial translation of the shaft and rotation of the shaft about its longitudinal axis, or by use of pull wires, shape memory actuators, etc. In one aspect of the invention, the shaft distal end may be steered during a surgical procedure so as to adopt a suitable conformation, thereby allowing the shaft distal end to be guided to a target site, for example, to a site between the processes of two adjacent vertebrae. By applying a high frequency voltage between the at least one active electrode and at least one return electrode at a suitable voltage level below the threshold value for ablation (i.e., in a subablation mode), interspinous tissue at the target site undergoes controlled shrinkage. The method may be conveniently performed percutaneously, or alternatively in an open procedure.

For a further understanding of the nature and advantages of the invention, reference should be made to the following description taken in conjunction with the accompanying drawings.

BRIEF DESCRIPTION OF THE DRAWINGS

FIGS. 7A–7C are cross-sectional views of the distal portions of three different embodiments of an electrosurgical probe, according to the present invention;

FIGS. 13A–13C illustrate an alternative embodiment incorporating a screen electrode;

DESCRIPTION OF SPECIFIC EMBODIMENTS

Figure 1:
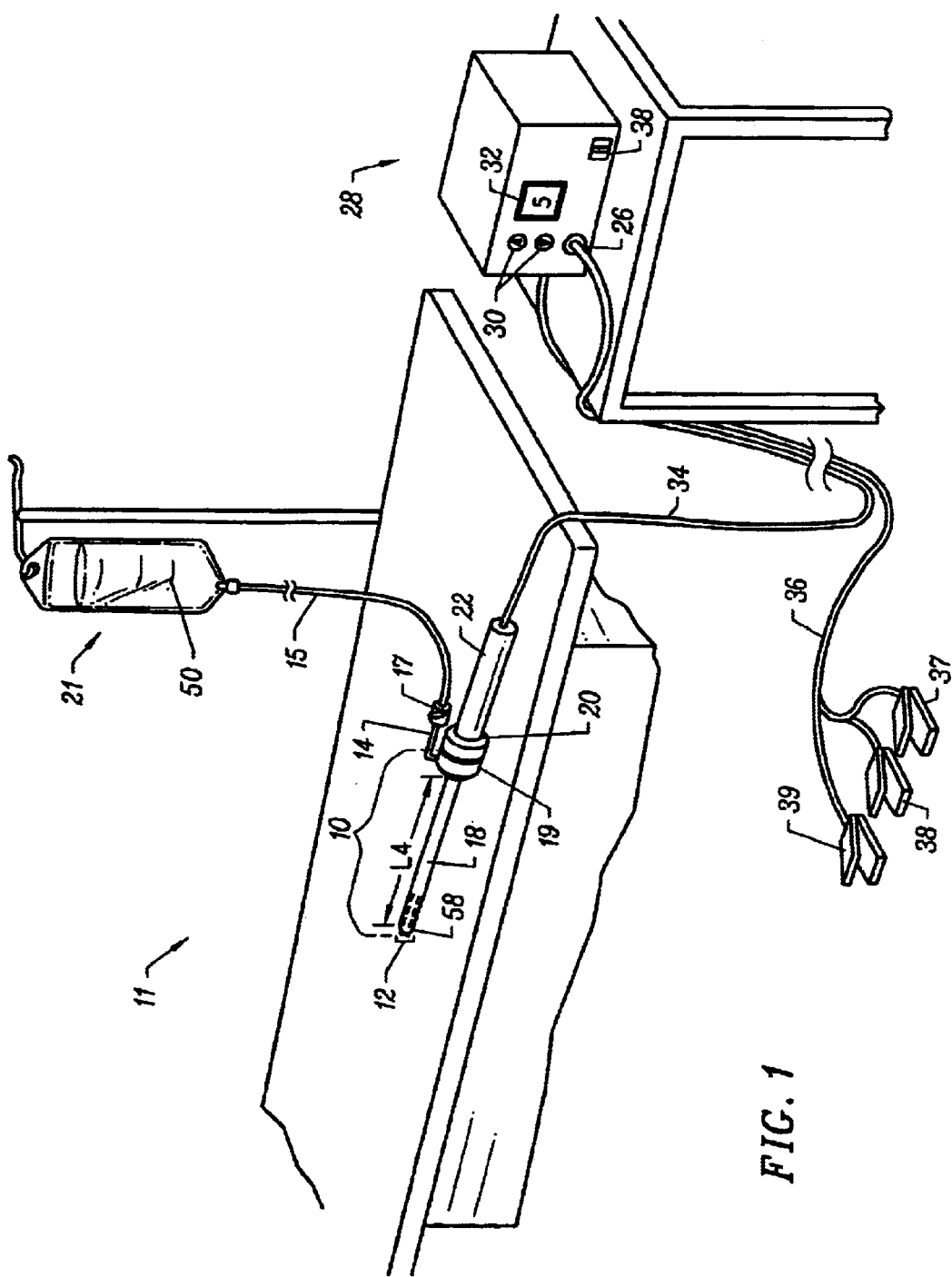
FIG. 1 is a perspective view of an electrosurgical system incorporating a power supply and an electrosurgical probe for tissue ablation, resection, incision, contraction and for vessel hemostasis according to the present invention.

The present invention provides systems and methods for selectively applying electrical energy to a target location within or on a patient's body, particularly including support tissue or other body structures in the spine. These procedures include treating interspinous tissue, degenerative discs, laminectomy/discectomy procedures for treating herniated discs, decompressive laminectomy for stenosis in the lumbosacral and cervical spine, localized tears or fissures in the annulus fibrosus, nucleotomy, disc fusion procedures, medial facetectomy, posterior lumbosacral and cervical spine fusions, treatment of scoliosis associated with vertebral disease, foraminotomies to remove the roof of the intervertebral foramina to relieve nerve root compression and anterior cervical and lumbar discectomies. These procedures may be performed through open procedures, or using minimally invasive techniques, such as thoracoscopy, arthroscopy, laparascopy or the like.

The present invention involves a system and method for treating the interspinous tissue (e.g., ligaments, tendons, cartilage, synovial tissue between the vertebrae, and other support tissue within and surrounding the vertebral column). In some embodiments, RF energy is used to heat and shrink the interspinous tissue to stabilize the vertebral column and reduce pain in the back and neck. In one aspect of the invention, an active electrode is positioned adjacent the interspinous tissue and the interspinous tissue is heated, preferably with RF energy, to a sufficient temperature to shrink the interspinous tissue. In a specific embodiment, a high frequency voltage difference is applied between one or more active electrode(s) and one or more return electrode(s) to develop high electric field intensities in the vicinity of the target tissue to controllably heat the target tissue.

The present invention also involves techniques for treating disc defects or disorders with RF energy. In some embodiments, RF energy is used to ablate, debulk and/or stiffen the tissue structure of the disc to reduce the volume of the disc, thereby relieving neck and back pain. In one aspect of the invention, spinal disc tissue is volumetrically removed or ablated to form holes, channels, divots or other spaces within the disc. In this procedure, a high frequency voltage is applied between one or more active electrode(s) and one or more return electrode(s) to develop high electric field intensities in the vicinity of the target tissue. The high electric field intensities adjacent the active electrode(s) lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to prior art electrosurgical desiccation and vaporization of tissue which typically involve dehydrating the tissue by the removal of water from within the cells and extracellular fluids.

The high electric field intensities may be generated by applying a high frequency voltage that is sufficient to vaporize an electrically conductive fluid over at least a portion of the active electrode(s) in the region between the distal tip of the active electrode(s) and the target tissue. The electrically conductive fluid may be a liquid or gas, such as isotonic saline, blood, or extracellular fluid, delivered to, or already present at, the target site; or a viscous fluid, such as a gel, applied to the target site. Since the vapor layer or vaporized region has a relatively high electrical impedance, it minimizes current flow into the electrically conductive fluid. This ionization, under the conditions described herein, induces the discharge of energetic electrons and photons from the vapor layer and to the surface of the target tissue. A more detailed description of this phenomena, termed Coblation® can be found in commonly assigned U.S. Pat. No. 5,697,882 the complete disclosure of which is incorporated herein by reference.

Applicant believes that the principal mechanism of tissue removal in the Coblation® mechanism of the present invention is molecular dissociation of tissue components induced by energetic electrons or ions that have been energized in a plasma adjacent to the active electrode(s). When a liquid is heated enough that atoms vaporize from the surface faster than they recondense, a gas is formed. When the gas is heated sufficiently that the atoms collide with each other and their electrons are removed in the process, an ionized gas or plasma is formed (the so-called "fourth state of matter"). A more complete description of plasmas can be found in *Plasma Physics*, by R. J. Goldston and P. H. Rutherford of the Plasma Physics Laboratory of Princeton University (1995), the entire contents of which are incorporated herein by reference. When the density of the vapor layer (or within a bubble formed in the electrically conductive liquid) becomes sufficiently low (i.e., less than approximately $10_{20}$ atoms/cm$^3$ for aqueous solutions), the electron mean free path increases to enable subsequently injected electrons to cause impact ionization within these regions of low density (i.e., vapor layers or bubbles). Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species.

Plasmas may be formed by heating a gas and ionizing the gas by driving an electric current through it, or by transmitting radio waves into the gas. Generally, these methods of plasma formation give energy to free electrons in the plasma directly, and then electron-atom collisions liberate more electrons, and the process cascades until the desired degree of ionization is achieved. Often, the electrons carry the electrical current or absorb the radio waves and, therefore, are hotter than the ions. Thus, in applicant's invention, the electrons, which are carried away from the tissue towards the return electrode, carry most of the plasma's heat with them, allowing the ions to break apart the tissue molecules in a substantially non-thermal manner.

In some embodiments, the present invention applies high frequency (RF) electrical energy in an electrically conductive media environment to shrink (e.g., to decrease the dimensions, tighten, contract, or reduce the volume), or remove (e.g., resect, cut, or ablate) a tissue structure, and to seal transected vessels within the region of the target tissue. The present invention may also be useful for sealing larger arterial vessels, e.g., on the order of about 1 mm in diameter. In some embodiments, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue. In other embodiments, an electrosurgical instrument is provided having one or more coagulation electrode(s) configured for sealing a severed vessel, such as an arterial vessel; and one or more active electrodes configured for either contracting the collagen fibers within the tissue, or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate or shrink with the active electrode(s). In other embodiments, the power supply is combined with the coagulation instrument such that the coagulation electrode is used when the power supply is in the coagulation mode (low voltage), and the active electrode (s) are used when the power supply is in the ablation mode (higher voltage).

In one method of the present invention, one or more active electrodes are brought into close proximity to tissue at a target site, and the power supply is activated in the ablation mode such that sufficient voltage is applied between the active electrodes and the return electrode to volumetrically remove the tissue through molecular dissociation, as described below. During this process, vessels within the tissue will be severed. Smaller vessels will be automatically sealed with the system and method of the present invention. Larger vessels, and those with a higher flow rate, such as arterial vessels, may not be automatically sealed in the ablation mode. In these cases, the severed vessels may be sealed by activating a control (e.g., a foot pedal) to reduce the voltage of the power supply into the coagulation mode. In this mode, the active electrodes may be pressed against the severed vessel to provide sealing and/or coagulation of the vessel. Alternatively, a coagulation electrode located on the same or a different instrument may be pressed against the severed vessel. Once the vessel is adequately sealed, the surgeon activates a control (e.g., another foot pedal) to increase the voltage of the power supply back into the ablation mode.

In another aspect, the present invention may be used to shrink or contract collagen connective tissue which support the vertebral column, or tissue within the disc. In these procedures, the RF energy heats the tissue directly by virtue of the electrical current flow therethrough, and/or indirectly through the exposure of the tissue to fluid heated by RF energy, to elevate the tissue temperature from normal body temperatures (e.g., 37° C.) to temperatures in the range of 45° C. to 90° C., preferably in the range from about 60° C. to 70° C. Thermal shrinkage of collagen fibers occurs within a small temperature range, which, for mammalian collagen, is in the range from 60° C. to 70° C. (Deak, G., et al., "*The Thermal Shrinkage Process of Collagen Fibres as Revealed by Polarization Optical Analysis of Topooptical Staining Reactions,*" Acta Morphological Acad. Sci. of Hungary, Vol. 15(2), pp. 195–208, 1967). Previously reported research has attributed thermal shrinkage of collagen to the cleaving of the internal stabilizing cross-linkages within the collagen matrix (Deak, ibid). It has also been reported that when the collagen temperature is increased above 70° C., the collagen matrix begins to relax again and the shrinkage effect is reversed resulting in no net shrinkage (Allain, J. C., et al., "*Isometric Tensions Developed During the Hydrothermal Swelling of Rat Skin,*" Connective Tissue Research, Vol. 7, pp 127–133, 1980), the complete disclosure of which is incorporated herein by reference. Consequently, the controlled heating of tissue to a precise depth is critical to the achievement of therapeutic collagen shrinkage. A more detailed description of collagen shrinkage can be found in U.S. patent application Ser. No. 08/942,580 filed on Oct. 2, 1997, the complete disclosure of which is incorporated herein by reference.

The preferred depth of heating to effect the shrinkage of collagen in the heated region (i.e., the depth to which the tissue is elevated to temperatures between 60° C. to 70° C.) generally depends on (1) the thickness of the target tissue, (2) the location of nearby structures (e.g., nerves) that should not be exposed to damaging temperatures, and/or (3) the location of the collagen tissue layer within which therapeutic shrinkage is to be effected. The depth of heating is usually in the range from 1.0 mm to 5.0 mm. In some embodiments of the present invention, the tissue is purposely damaged in a thermal heating mode to create necrosed or scarred tissue at the tissue surface. The high frequency voltage in the thermal heating mode is below the threshold of ablation as described above, but sufficient to cause some thermal damage to the tissue immediately surrounding the electrodes without vaporizing or otherwise debulking this tissue in situ.

Typically, it is desired to achieve a tissue temperature in the range of about 60° C. to 100° C. to a depth of about 0.2 mm to 5 mm, usually about 1 mm to 2 mm. The voltage required for this thermal damage will partly depend on the electrode configurations, the conductivity of the area immediately surrounding the electrodes, the time period in which the voltage is applied and the depth of tissue damage desired. With the electrode configurations described in this application (e.g., FIGS. 15A–15D), the voltage level for thermal heating will usually be in the range of about 20 volts RMS to 300 volts RMS, preferably about 60 volts RMS to 200 volts RMS. The peak-to-peak voltages for thermal heating with a square wave form having a crest factor of about 2 are typically in the range of about 40 volts peak-to-peak to 600 volts peak-to-peak, preferably about 120 volts peak-to-peak to 400 volts peak-to-peak. In some embodiments, capacitors or other electrical elements may be used to increase the crest factor up to 10. The higher the voltage is within this range, the less time required. If the voltage is too high, however, the surface tissue may be vaporized, debulked or ablated, which is generally undesirable.

In yet another embodiment, the present invention may be used for treating degenerative discs which have one or more fissures or tears. In these embodiments, the active and return electrode(s) are positioned in or around the inner wall of the annulus fibrosus such that the active electrode is adjacent to the fissure to be treated. High frequency voltage is applied between the active and return electrodes to heat the fissure and shrink the collagen fibers and create a seal or weld within the inner wall, thereby helping to close the fissure in the annulus. In these embodiments, the return electrode will typically be positioned proximally from the active electrode (s) on the instrument shaft, and an electrically conductive fluid will be applied to the target site to create the necessary current path between the active and return electrodes. In alternative embodiments, the disc tissue may complete this electrically conductive path.

The present invention is also useful for removing or ablating tissue around nerves, such as spinal, peripheral or cranial nerves. One of the significant drawbacks with prior art shavers or microdebriders, conventional electrosurgical devices, and lasers is that they do not differentiate between the target tissue and the surrounding nerves or bone. Therefore, the surgeon must be extremely careful during procedures using these devices to avoid damage to the bone or nerves within and around the target site. In the present invention, the Coblation® process for treating tissue results in no, or minimal, collateral tissue damage, as discussed above. This allows the surgeon to remove tissue close to a nerve without causing collateral damage to the nerve.

In addition to the generally precise nature of the novel mechanisms of the present invention, applicant has discovered an additional method of ensuring that adjacent nerves are not damaged during tissue removal. According to the present invention, systems and methods are provided for distinguishing between the fatty tissue immediately surrounding nerve fibers and the target tissue that is to be removed during the procedure. Peripheral nerves usually comprise a connective tissue sheath, or epineurium, enclosing the bundles of nerve fibers, each bundle being surrounded by its own sheath of connective tissue (the perineurium) to protect these nerve fibers. The outer protective tissue sheath or epineurium typically comprises a fatty tissue (e.g., adipose tissue) having substantially different electrical properties from those of the target tissue, such as intervertebral disc tissue and interspinous tissue. The system of the present invention measures the electrical properties of the tissue at the tip of the probe with one or more active electrode(s). These electrical properties may include electrical conductivity at one, several, or a range of frequencies (e.g., in the range from 1 kHz to 100 MHz), dielectric constant, capacitance or combinations of these. In this embodiment, an audible signal may be produced when the sensing electrode(s) at the tip of the probe detects the fatty tissue surrounding a nerve, or direct feedback control can be provided to only supply power to the active electrode (s) either individually or to the complete array of electrodes, if and when the tissue encountered at the tip or working end of the probe is "normal" (e.g., non-fatty) tissue based on the measured electrical properties.

In one embodiment, the current limiting elements (discussed in detail below) are configured such that the active electrodes will shut down or turn off when the electrical impedance reaches a threshold level. When this threshold level is set to the impedance of the fatty tissue surrounding nerves, the active electrodes will shut off whenever they come in contact with, or in close proximity to, nerves. Meanwhile, the other active electrodes, which are in contact with or in close proximity to target tissue, will continue to conduct electric current to the return electrode. This selective ablation of lower impedance tissue in combination with the Coblation® mechanism of the present invention allows the surgeon to precisely remove tissue around nerves or bone. Applicant has found that the present invention is capable of volumetrically removing tissue closely adjacent to nerves without impairing the function of the nerves, and without significantly damaging the tissue of the epineurium.

In addition to the above, applicant has discovered that the Coblation® mechanism of the present invention can be manipulated to ablate or remove certain tissue structures, while having little effect on other tissue structures. As discussed above, the present invention uses a technique of vaporizing electrically conductive fluid to form a plasma layer or pocket around the active electrode(s), and then inducing the discharge of energy from this plasma or vapor layer to break the molecular bonds of the tissue structure. Energy evolved by the energetic electrons (e.g., 4 eV to 5 eV) can subsequently bombard a molecule and break its bonds, dissociating a molecule into free radicals, which then combine into final gaseous or liquid species. The energy evolved by the energetic electrons may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors.

Since different tissue structures have different molecular bonds, the present invention can be configured to break the molecular bonds of certain tissue, while having too low an energy to break the molecular bonds of other tissue. For example, fatty tissue, (e.g., adipose tissue) has double bonds that require a substantially higher energy level than 4 eV to 5 eV to break (typically on the order of about 8 eV). Accordingly, the present invention in its current configuration generally does not ablate or remove such fatty tissue. However, the present invention may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomena can be found in co-pending U.S. patent application Ser. No. 09/032,375, filed Feb. 27, 1998, the complete disclosure of which is incorporated herein by reference.

In yet other embodiments, the present invention provides systems, apparatus and methods for selectively removing tumors, e.g., facial tumors, or other undesirable body structures while minimizing the spread of viable cells from the tumor. Conventional techniques for removing such tumors generally result in the production of smoke in the surgical setting, termed an electrosurgical or laser plume, which can spread intact, viable bacteria or viral particles from the tumor or lesion to the surgical team or to other portions of the patient's body. This potential spread of viable cells or particles has resulted in increased concerns over the proliferation of certain debilitating and fatal diseases, such as hepatitis, herpes, HIV and papillomavirus. In the present invention, high frequency voltage is applied between the active electrode(s) and one or more return electrode(s) to volumetrically remove at least a portion of the tissue of the tumor or lesion by the dissociation or disintegration of large organic molecules (e.g., proteins and nucleic acids) into non-viable atoms and low molecular species. Specifically, the present invention converts solid tissue into non-condensable gases that are no longer intact or viable, and thus, incapable of spreading viable tumor cells or infectious agents to other portions of the patient's body or to the surgical staff. The high frequency voltage is preferably selected to effect controlled removal of such target tissue while minimizing tissue damage to surrounding or underlying tissue. A more complete description of this phenomenon can be found in co-pending U.S. patent application Ser. No. 09/109,219, filed Jun. 30, 1998, the complete disclosure of which is incorporated herein by reference.

The electrosurgical probe or catheter of the present invention can comprise a shaft or a handpiece having a proximal end and a distal end which supports one or more active electrode(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

For endoscopic procedures within the spine, the shaft will have a suitable diameter and length to allow the surgeon to reach the target site (e.g., a disc or vertebra). Thus, the shaft will usually have a length in the range of about 5.0 cm to 30.0 cm, and a diameter in the range of about 0.2 mm to about 20 mm. Typically, the shaft is delivered directly through the patient's back in a posterior approach. The shaft may also be introduced through rigid or flexible endoscopes. Alternatively, the shaft may be a flexible catheter that is introduced through a percutaneous penetration in the patient. Specific shaft designs will be described in detail in connection with the drawings hereinafter.

In one embodiment, the probe may comprise a long, thin needle (e.g., on the order of about 1 mm in diameter or less) that can be percutaneously introduced through the patient's back directly into, or adjacent to, the spine. The needle will include one or more active electrode(s) for applying electrical energy to tissues within or surrounding the spine. The needle may include one or more return electrode(s), or the return electrode may be positioned on the patient as a dispersive pad. In either embodiment, sufficient electrical energy is applied to the active electrode(s) to either shrink the collagen fibers within the spinal disc, to volumetrically remove tissue within the disc, or to shrink interspinous tissue (e.g., ligaments) surrounding and supporting the vertebrae.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the drawings hereinafter.

The active electrode(s) are preferably supported within or by an insulating support positioned near the distal end of the instrument shaft. The return electrode may be located on the instrument shaft, on another instrument, or on the external surface of the patient (i.e., a dispersive pad). The close proximity of nerves and other sensitive tissue in and around the spinal cord, however, makes a bipolar design more preferable because this minimizes the current flow through non-target tissue and surrounding nerves. Accordingly, the return electrode is preferably either integrated with the instrument body, or with another device located in close proximity to the instrument body. The proximal end of the instrument(s) will include the appropriate electrical connections for coupling the return electrode(s) and the active electrode(s) to a high frequency power supply, such as an electrosurgical generator.

In some embodiments, the active electrode(s) have an active portion or surface with surface geometries shaped to promote high electric field intensity and associated current density along the leading edges of the electrodes. Suitable surface geometries may be obtained by creating electrode shapes that include preferential sharp edges, or by creating asperities or other surface roughness on the surface(s) of the active electrode(s). Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes.

Additionally or alternatively, the active electrode surface(s) may be modified through chemical, electrochemical or abrasive methods to create a multiplicity of surface asperities on the electrode surface. These surface asperities will promote high electric field intensities between the active electrode surface(s) and the target tissue to facilitate ablation or cutting of the tissue. For example, surface asperities may be created by etching the active electrodes with etchants having a pH less than 7.0, or by using a high velocity stream of abrasive particles (e.g., grit blasting) to create asperities on the surface of an elongated electrode. A more detailed description of such electrode configurations can be found in U.S. Pat. No. 5,843,019, the complete disclosure of which is incorporated herein by reference.

The return electrode is typically spaced proximally from the active electrode(s) a suitable distance to avoid electrical shorting between the active and return electrodes in the presence of electrically conductive fluid. In some of the embodiments described herein, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

The current flow path between the active electrodes and the return electrode(s) may be generated by submerging the tissue site in an electrical conducting fluid (e.g., within a viscous fluid, such as an electrically conductive gel) or by directing an electrically conductive fluid along a fluid path to the target site (i.e., a liquid, such as isotonic saline, hypotonic saline; or a gas, such as argon). The conductive gel may also be delivered to the target site to achieve a slower, more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conductive fluid between the active and return electrodes is described in U.S. Pat. No. 5,697,281, the complete disclosure of which is incorporated herein by reference.

Alternatively, the body's natural conductive fluids, such as blood or extracellular fluids, may be sufficient to establish a conductive path between the return electrode(s) and the active electrode(s), and to provide the conditions for establishing a vapor layer, as described above. However, conductive fluid that is introduced into the patient is generally preferred over blood because blood will tend to coagulate at certain temperatures. In addition, the patient's blood may not have sufficient electrical conductivity to adequately form a plasma in some applications. Advantageously, a liquid electrically conductive fluid (e.g., isotonic saline) may be used to concurrently "bathe" the target tissue surface to provide an additional means for removing any tissue, and to cool the region of the target tissue ablated in the previous moment.

The power supply may include a fluid interlock for interrupting power to the active electrode(s) when there is insufficient conductive fluid around the active electrode(s). This ensures that the instrument will not be activated when conductive fluid is not present, minimizing the tissue damage that may otherwise occur. A more complete description of such a fluid interlock can be found in commonly assigned, co-pending U.S. application Ser. No. 09/058,336, filed Apr. 10, 1998, the complete disclosure of which is incorporated herein by reference.

In some procedures, it may also be necessary to retrieve or aspirate the electrically conductive fluid and/or the non-condensable gaseous products of ablation. In addition, it may be desirable to aspirate small pieces of tissue or other body structures that are not completely disintegrated by the high frequency energy, or other fluids at the target site, such as blood, mucus, etc. Accordingly, the system of the present invention may include one or more suction lumen(s) in the instrument, or on another instrument, coupled to a suitable vacuum source for aspirating fluids from the target site. In addition, the invention may include one or more aspiration electrode(s) coupled to the distal end of the suction lumen for ablating, or at least reducing the volume of, non-ablated tissue fragments that are aspirated into the lumen. The aspiration electrode(s) function mainly to inhibit clogging of the lumen that may otherwise occur as larger tissue fragments are drawn therein. The aspiration electrode(s) may be different from the ablation active electrode(s), or the same electrode(s) may serve both functions. A more complete description of instruments incorporating aspiration electrode(s) can be found in commonly assigned, copending U.S. patent application Ser. No. 09/010,382 entitled "Systems And Methods For Tissue Resection, Ablation And Aspiration", filed Jan. 21, 1998, the complete disclosure of which is incorporated herein by reference.

As an alternative or in addition to suction, it may be desirable to contain the excess electrically conductive fluid, tissue fragments, and/or gaseous products of ablation at or near the target site with a containment apparatus, such as a basket, retractable sheath, or the like. This embodiment has the advantage of ensuring that the conductive fluid, tissue fragments, or ablation products do not flow through the patient's vasculature or into other portions of the body. In addition, it may be desirable to limit the amount of suction to limit the undesirable effect suction may have on hemostasis of severed blood vessels.

The present invention may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller or along the conductive path from the controller to the distal tip of the instrument. Alternatively, the resistance and/or capacitance may occur on the surface of the active electrode(s) due to oxide layers which form on certain metals (e.g., titanium), or a resistive coating on the surface of a metal (such as platinum).

The tip region of the instrument may comprise many independent active electrodes designed to deliver electrical energy in the vicinity of the tip. The selective application of electrical energy to the conductive fluid is achieved by connecting each individual active electrode and the return electrode to a power source having independently controlled or current limited channels. The return electrode(s) may comprise a single tubular member of conductive material proximal to the electrode array at the tip. The single tubular member may also serve as a conduit for the supply of the electrically conductive fluid between the active and return electrodes. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the active electrodes with conduction of high frequency current from each individual active electrode to the return electrode. The current flow from each individual active electrode to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the active electrode(s) for appropriate time intervals effects shrinking, cutting, removing, ablating, shaping, contracting or otherwise modifying the target tissue. In some embodiments of the present invention, the tissue volume over which energy is dissipated (i.e., over which a high current density exists) may be more precisely controlled by, for example, the use of a multiplicity of small active electrodes whose effective diameters or principal dimensions range from about 10 mm to 0.01 mm, preferably from about 2 mm to 0.05 mm, and more preferably from about 1 mm to 0.1 mm. In this embodiment, electrode areas for both circular and non-circular terminals will have a contact area (per active electrode) below 50 mm$^2$ for electrode arrays, and as large as 75 mm$^2$ for single electrode embodiments. In multiple electrode array embodiments, the contact area of each active electrode is typically in the range from 0.0001 mm$^2$ to 1 mm$^2$, and more preferably from 0.001 mm$^2$ to 0.5 mm$^2$. The circumscribed area of the electrode array or active electrode is in the range from 0.25 mm$^2$ to 75 mm$^2$, preferably from 0.5 mm$^2$ to 40 mm$^2$. In multiple electrode embodiments, the array will usually include at least two isolated active electrodes, often at least five active electrodes, often greater than 10 active electrodes and even 50 or more active electrodes, disposed over the distal contact surfaces on the shaft. The use of small diameter active electrodes increases the electric field intensity and reduces the extent or depth of tissue heating as a consequence of the divergence of current flux lines which emanate from the exposed surface of each active electrode.

The area of the tissue treatment surface can vary widely, and the tissue treatment surface can assume a variety of geometries, with particular areas and geometries being selected for specific applications. The geometries can be planar, concave, convex, hemispherical, conical, a linear "in-line" array, or virtually any other regular or irregular shape. Most commonly, the active electrode(s) or active electrode array will be formed at the distal tip of the electrosurgical instrument shaft, frequently being planar, disk-shaped, or hemispherical surfaces for use in reshaping procedures, or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

It should be clearly understood that the invention is not limited to electrically isolated active electrodes, or even to a plurality of active electrodes. For example, the array of active electrodes may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s), or the like.

In some embodiments, the electrode support and the fluid outlet may be recessed from an outer surface of the instrument or handpiece to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the active electrode(s) and the return electrode(s) to maintain the conductive path therebetween. In addition, this will help to maintain a vapor layer and subsequent plasma layer between the active electrode(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

In other embodiments, the active electrodes are spaced from the target tissue a sufficient distance to minimize or avoid contact between the tissue and the vapor layer formed around the active electrodes. In these embodiments, contact between the heated electrons in the vapor layer and the tissue is minimized as these electrons travel from the vapor layer back through the conductive fluid to the return electrode. The ions within the plasma, however, will have sufficient energy, under certain conditions such as higher voltage levels, to accelerate beyond the vapor layer to the tissue. Thus, the bonds of tissue components are dissociated or broken as in previous embodiments, while minimizing the electron flow, and thus the thermal energy, in contact with the tissue.

The electrically conductive fluid should have a minimum threshold conductivity to provide a suitable conductive path between the return electrode and the active electrode(s). The electrical conductivity of the fluid (in units of milliSiemens per centimeter or mS/cm) will usually be greater than 0.2 mS/cm, preferably greater than 2 mS/cm, and more preferably greater than 10 mS/cm. In an exemplary embodiment, the electrically conductive fluid is isotonic saline, which has an electrical conductivity of about 17 mS/cm. Applicant has found that a more conductive fluid, or one with a higher ionic concentration, will usually provide a more aggressive ablation rate. For example, a saline solution with higher levels of sodium chloride than isotonic saline (which is on the order of about 0.9% sodium chloride), e.g., on the order of greater than 1% or between about 3% and 20%, may be desirable. Alternatively, the invention may be used with different types of conductive fluids that increase the power of the plasma layer by, for example, increasing the quantity of ions in the plasma, or by providing ions that have higher energy levels than sodium ions. For example, the present invention may be used with elements other than sodium, such as potassium, magnesium, calcium and other metals in Groups located towards the left side of the Periodic Table. In addition, other electronegative elements may be used in place of chlorine, such as fluorine.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400–600 kHz) to minimize low frequency current flow into the heart or the nerves of the head and neck. The RMS (root mean square) voltage applied will usually be in the range from about 5 volts to 1000 volts, preferably being in the range from about 10 volts to 500 volts, often between about 150 to 400 volts depending on the active electrode size, the operating frequency and the operation mode of the particular procedure or desired effect on the tissue (i.e., contraction, coagulation, cutting, or ablation). Typically, the peak-to-peak voltage for ablation or cutting, with a square wave form, will be in the range of 10 volts to 2000 volts, and preferably in the range of 100 volts to 1800 volts, and more preferably in the range of about 300 volts to 1500 volts, often in the range of about 300 volts to 800 volts peak to peak (again, depending on the electrode size, number of electrodes, the operating frequency, and the operation mode). Lower peak-to-peak voltages will be used for tissue coagulation, thermal heating of tissue, or collagen contraction, and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude, with a sufficiently high frequency (e.g., on the order of 5 kHz to 20 MHz) such that the voltage is effectively applied continuously (as compared with e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001 %.

The preferred power source of the present invention delivers a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery, or other endoscopic surgery procedure. For cardiac procedures, and potentially for neurosurgery, the power source may have an additional filter, for filtering leakage voltages at frequencies below 100 kHz, particularly voltages around 60 kHz. Alternatively, a power source having a higher operating frequency, e.g., 300 kHz to 600 kHz may be used in certain procedures in which stray low frequency currents may be problematic. A description of one suitable power source can be found in co-pending patent applications Ser. Nos. 09/058,571 and 09/058,336, filed Apr. 10, 1998, the complete disclosure of both applications are incorporated herein by reference for all purposes.

The power source may be current limited or otherwise controlled so that undesired heating of the target tissue or surrounding (non-target) tissue does not occur. In a presently preferred embodiment of the present invention, current limiting inductors are placed in series with each independent active electrode, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from the active electrode into the low resistance medium (e.g., saline irrigant or blood).

Referring to FIG. 1, an exemplary electrosurgical system 11 for treatment of tissue in the spine will now be described in detail. Electrosurgical system 11 generally comprises an electrosurgical handpiece or probe 10 connected to a power supply 28 for providing high frequency voltage to a target site, and a fluid source 21 for supplying electrically conductive fluid 50 to probe 10. In addition, electrosurgical system 11 may include an endoscope (not shown) with a fiber optic head light for viewing the surgical site. The endoscope may be integral with probe 10, or it may be part of a separate instrument. The system 11 may also include a vacuum source (not shown) for coupling to a suction lumen or tube 205 (see FIG. 2) in probe 10 for aspirating the target site.

As shown, probe 10 generally includes a proximal handle 19 and an elongate shaft 18 having an array 12 of active electrodes 58 at its distal end. A connecting cable 34 has a connector 26 for electrically coupling active electrodes 58 to power supply 28. The active electrodes 58 are electrically isolated from each other and each of terminal of active electrodes 58 is connected to an active or passive control network within power supply 28 by means of a plurality of individually insulated conductors (not shown). A fluid supply tube 15 is connected to a fluid tube 14 of probe 10 for supplying electrically conductive fluid 50 to the target site. Fluid supply tube 15 may be connected to a suitable pump (not shown), if desired.

Power supply 28 has an operator controllable voltage level adjustment 30 to change the applied voltage level, which is observable at a voltage level display 32. Power supply 28 also includes first, second and third foot pedals 37, 38, 39 and a cable 36 which is removably coupled to power supply 28. The foot pedals 37, 38, 39 allow the surgeon to remotely adjust the energy level applied to active electrodes 58. In an exemplary embodiment, first foot pedal 37 is used to place the power supply into the "ablation" mode and second foot pedal 38 places power supply 28 into the "sub-ablation" mode (e.g., for coagulation or contraction of tissue). The third foot pedal 39 allows the user to adjust the voltage level within the "ablation" mode. In the ablation mode, a sufficient voltage is applied to the active electrodes to establish the requisite conditions for molecular dissociation of the tissue (i.e., vaporizing a portion of the electrically conductive fluid, forming charged particles within the vapor layer, and accelerating these charged particles). As discussed above, the requisite voltage level for ablation will vary depending on the number, size, shape and spacing of the electrodes, the distance to which the electrodes extend from the support member, etc. Once the surgeon places the power supply in the "ablation" mode, voltage level adjustment 30 or third foot pedal 39 may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the subablation mode, the power supply 28 applies a low enough voltage to the active electrodes to avoid vaporization of the electrically conductive fluid and subsequent molecular dissociation of the tissue. The surgeon may automatically toggle the power supply between the ablation and sub-ablation modes by alternately stepping on foot pedals 37, 38, respectively. In some embodiments, this allows the surgeon to quickly move between coagulation/thermal heating and ablation in situ, without having to remove his/her concentration from the surgical field or without having to request an assistant to switch the power supply. By way of example, as the surgeon is treating a target tissue in the ablation mode, the probe typically will simultaneously seal and/or coagulate small severed vessels within the tissue. However, larger vessels, or vessels with high fluid pressures (e.g., arterial vessels) may not be sealed in the ablation mode. Accordingly, the surgeon can simply step on foot pedal 38, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on foot pedal 37.

Figure 2:
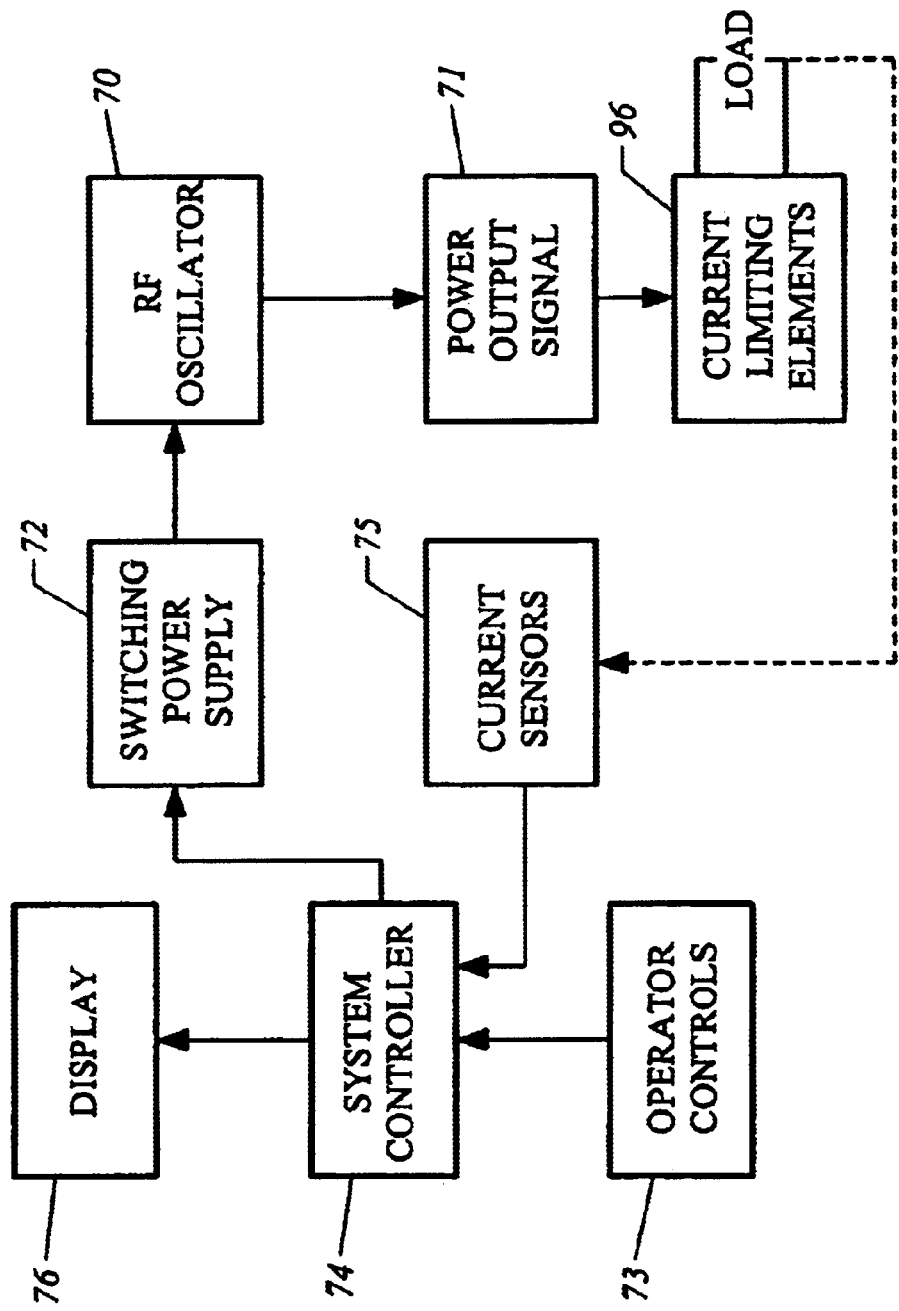
FIG. 2 schematically illustrates one embodiment of a power supply according to the present invention.
Figure 3:
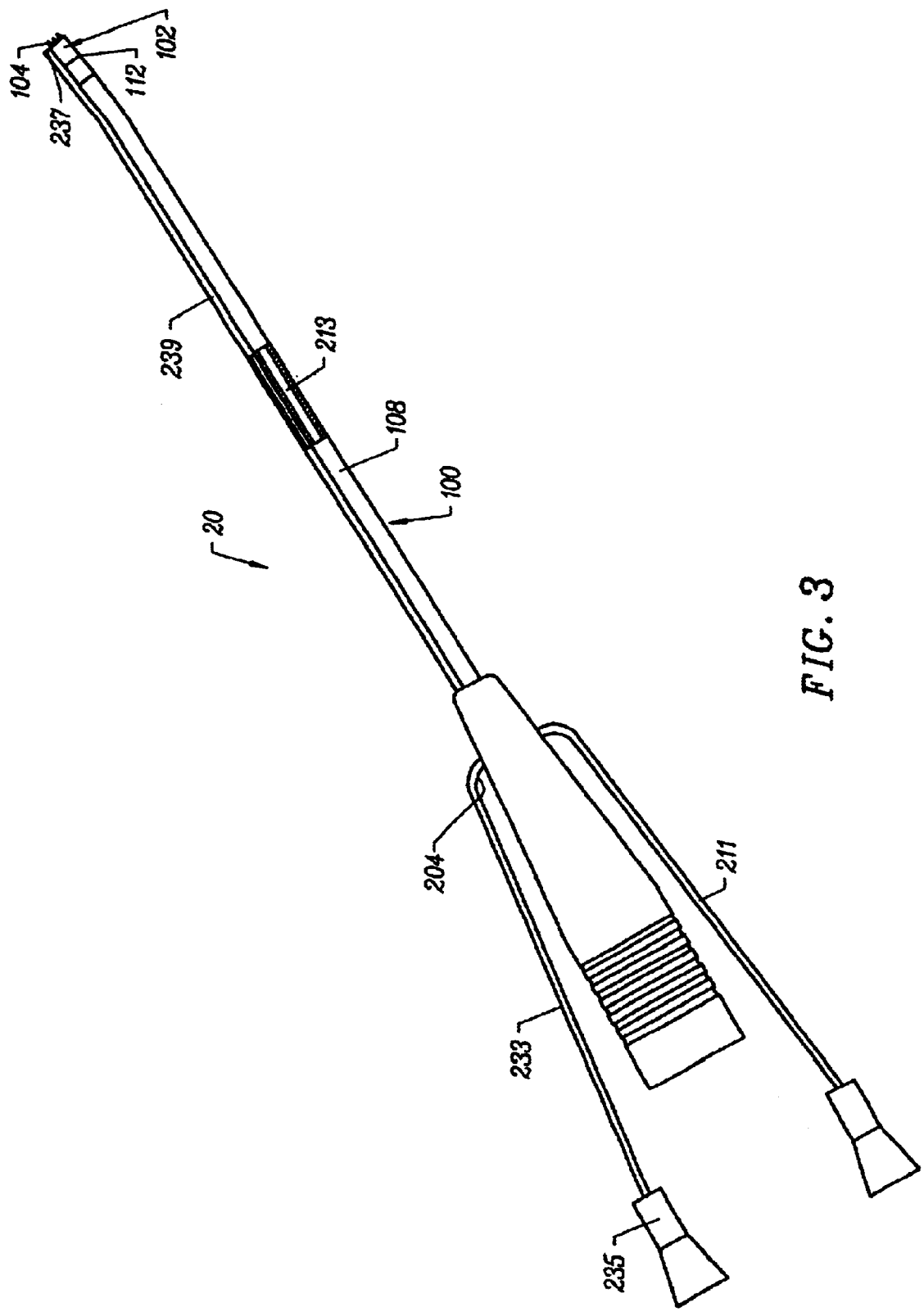
FIG. 3 is a side view of an electrosurgical probe according to the present invention.

Referring now to FIGS. 2 and 3, a representative high frequency power supply or generator for use according to the principles of the present invention will now be described. The high frequency power supply of the present invention is configured to apply a high frequency voltage of about 10 volts RMS to 500 volts RMS between one or more active electrodes (and/or a coagulation electrode) and one or more return electrodes. In the exemplary embodiment, the power supply applies about 70 volts RMS to 350 volts RMS in the ablation mode, and about 20 volts to 90 volts in a subablation mode, preferably 45 volts to 70 volts in the subablation mode (these values will, of course, vary depending on the probe configuration attached to the power supply and the desired mode of operation).

The preferred power source of the present invention delivers a high frequency current selectable to generate average power levels ranging from several milliwatts to tens of watts per electrode, depending on the volume of target tissue being treated, and/or the maximum allowed temperature selected for the probe tip. The power source allows the user to select the voltage level according to the specific requirements of a particular procedure, e.g., spinal surgery, arthroscopic surgery, dermatological procedure, ophthalmic procedures, open surgery, or other endoscopic surgery procedure.

As shown in FIG. 2, the power supply or generator generally comprises a radio frequency (RF) power oscillator 70 having output connections for coupling via a power output signal 71 to the load impedance, which is represented by the electrode assembly when the electrosurgical probe is in use. In the representative embodiment, RF oscillator 70 operates at about 100 kHz. The RF oscillator 70 is not limited to this frequency and may operate at frequencies of about 300 kHz to 600 kHz. In particular, for cardiac applications, the RF oscillator will preferably operate in the range of about 400 kHz to about 600 kHz. The RF oscillator will generally supply a square wave signal with a crest factor of about 1 to 2. Of course, this signal may be a sine wave signal or other suitable wave signal depending on the application and other factors, such as the voltage applied, the number and geometry of the electrodes, etc. The power output signal 71 is designed to incur minimal voltage decrease (i.e., sag) under load. This improves the applied voltage to the active electrodes and the return electrode, which improves the rate of volumetric removal of tissue during a procedure involving ablation.

Power is supplied to the oscillator 70 by a switching power supply 72 coupled between the power line and the RF oscillator rather than a conventional transformer. Switching power supply 72 allows the generator to achieve high peak power output without the large size and weight of a bulky transformer. The architecture of switching power supply 72 has also been designed to reduce electromagnetic noise such that U.S. and foreign EMI requirements are met. This architecture comprises a zero voltage switching or crossing, which causes the transistors to turn ON and OFF when the voltage is zero. Therefore, the electromagnetic noise produced by the transistors switching is vastly reduced. In an exemplary embodiment, the switching power supply 72 operates at about 100 kHz.

A system controller 74 coupled to the operator controls 73 (e.g., foot pedals and voltage selector) and display 76, is connected to a control input of switching power supply 72 for adjusting the generator output power by supply voltage variation. The controller 74 may be a microprocessor or an integrated circuit. The generator may also include one or more current sensors 75 for detecting the output current. The power supply is preferably housed within a metal casing which provides a durable enclosure for the electrical components therein. In addition, the metal casing reduces the electromagnetic noise generated within the power supply because the grounded metal casing functions as a "Faraday shield," thereby shielding the environment from internal sources of electromagnetic noise.

The power supply generally comprises a main or mother board containing generic electrical components required for many different surgical procedures (e.g., arthroscopy, urology, general surgery, dermatology, neurosurgery, etc.), and a daughter board containing application specific current-limiting circuitry (e.g., inductors, resistors, capacitors, and the like). The daughter board is coupled to the mother board by a detachable multi-pin connector to allow convenient conversion of the power supply to, e.g., applications requiring a different current limiting circuit design. For arthroscopy, for example, the daughter board preferably comprises a plurality of inductors of about 200 to 400 microhenries, usually about 300 microhenries, for each of the channels supplying current to the active electrodes.

Alternatively, in one embodiment, current limiting inductors are placed in series with each independent active electrode, where the inductance of the inductor is in the range of 10 uH to 50,000 uH, depending on the electrical properties of the target tissue, the desired tissue heating rate, and the operating frequency. Alternatively, capacitor-inductor (LC) circuit structures may be employed, as described previously in co-pending PCT application No. PCT/US94/05168, the complete disclosure of which is incorporated herein by reference. Additionally, current limiting resistors may be selected. Preferably, these resistors will have a large positive temperature coefficient of resistance so that, as the current level begins to rise for any individual active electrode in contact with a low resistance medium (e.g., saline irrigant or conductive gel), the resistance of the current limiting resistor increases significantly, thereby minimizing the power delivery from the active electrode into the low resistance medium (e.g., saline irrigant or conductive gel). Power output signal may also be coupled to a plurality of current limiting elements, which are preferably located on the daughter board since the current limiting elements may vary depending on the application. A more complete description of a representative power supply can be found in commonly assigned U.S. patent application Ser. No. 09/058,571, the disclosure of which is incorporated herein by reference.

Figure 4:
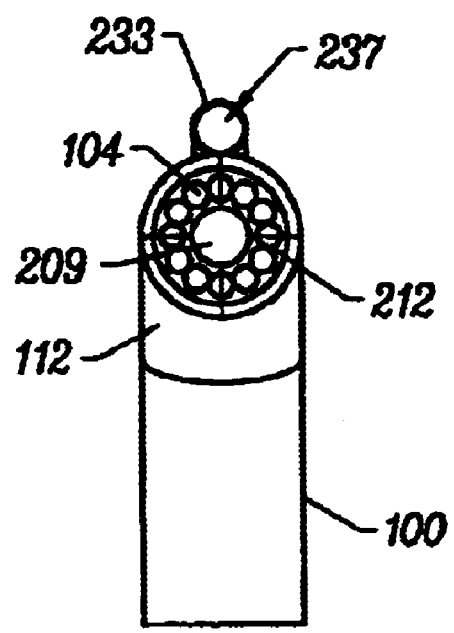
FIG. 4 is a view of the distal end portion of the probe of FIG. 3.
Figure 5:
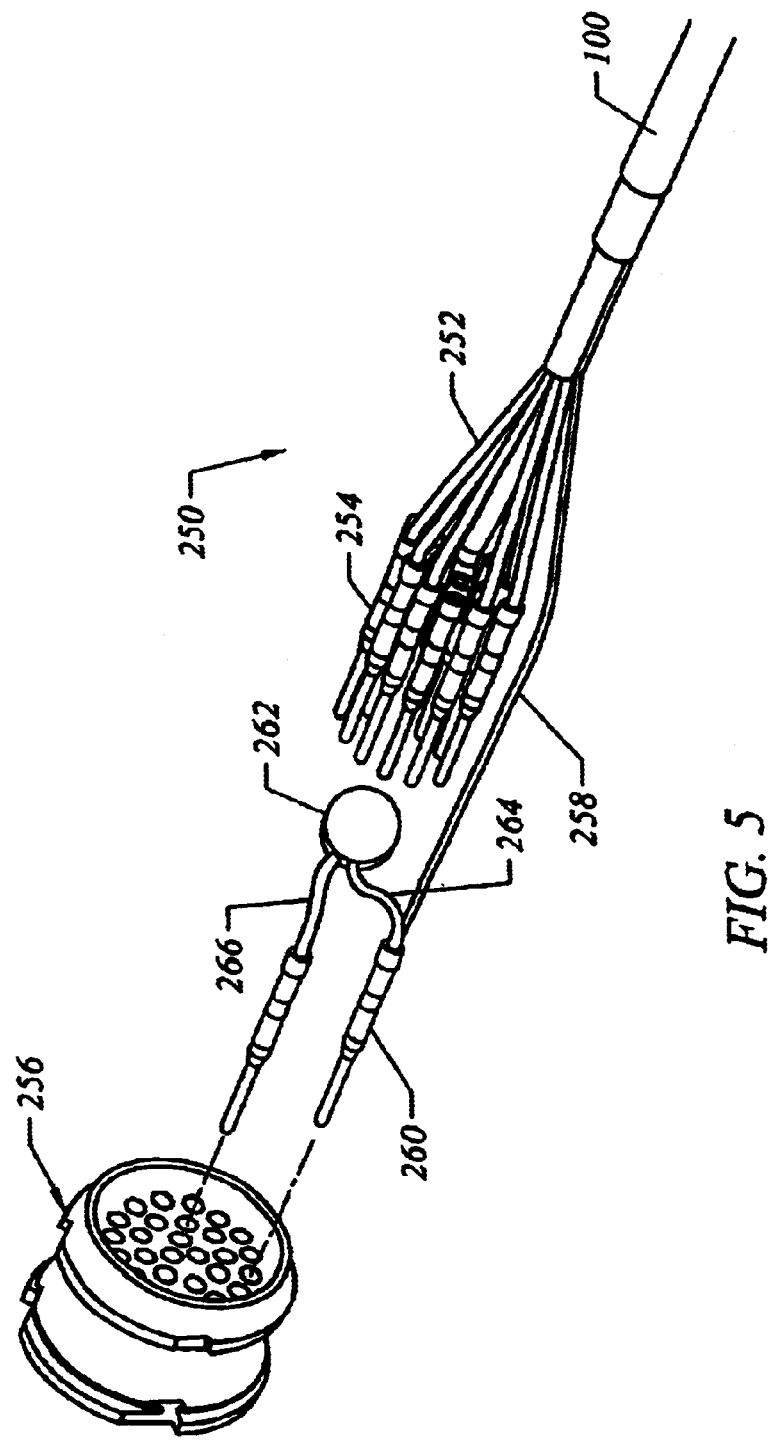
FIG. 5 is an exploded view of a proximal portion of the electrosurgical probe.

FIGS. 3–5 illustrate an exemplary electrosurgical probe 20 constructed according to the principles of the present invention. As shown in FIG. 3, probe 20 generally includes an elongated shaft 100 which may be flexible or rigid, a handle 204 coupled to the proximal end of shaft 100 and an electrode support member 102 coupled to the distal end of shaft 100. Shaft 100 preferably comprises an electrically conducting material, usually metal, such as tungsten, stainless steel alloys, platinum or its alloys, titanium or its alloys, molybdenum or its alloys, and nickel or its alloys. In this embodiment, shaft 100 includes an electrically insulating jacket 108, which is typically formed as one or more electrically insulating sheaths or coatings, such as polytetrafluoroethylene, polyimide, and the like. The provision of the electrically insulating jacket over the shaft prevents direct electrical contact between these metal elements and any adjacent non-target body structure or the surgeon. Such direct electrical contact between a body structure and an exposed electrode could result in unwanted heating and necrosis of the non-target structure at the point of contact. A return electrode 112 may comprise an annular band coupled to an insulating shaft and having a connector extending within the shaft to the shaft proximal end.

Handle 204 typically comprises a plastic material that is easily molded into a suitable shape for handling by the surgeon. Handle 204 defines an inner cavity (not shown) that houses the electrical connections 250 (FIG. 5), and provides a suitable interface for connection to an electrical connecting cable 22 (see FIG. 1). Electrode support member 102 extends from the distal end of shaft 100 (usually about 1 mm to 20 mm), and provides support for a plurality of electrically isolated active electrodes 104 (see FIG. 4). As shown in FIG. 4, a fluid tube 233 extends through an opening in handle 204, and includes a connector 235 for connection to a fluid supply source, for supplying electrically conductive fluid to the target site. Depending on the configuration of the distal surface of shaft 100, fluid tube 233 may extend through a single lumen (not shown) in shaft 100, or it may be coupled to a plurality of lumens (also not shown) that extend through shaft 100 to a plurality of openings at its distal end. In the representative embodiment, fluid tube 239 is a plastic tubing that extends along the exterior of shaft 100 to a point just distal of return electrode 112 (see FIG. 4). In this embodiment, the fluid is directed through an opening 237 past return electrode 112 to the active electrodes 104. Probe 20 may also include a valve 17 (FIG. 1) or equivalent structure for controlling the flow rate of the electrically conductive fluid to the target site.

As shown in FIG. 3, the distal portion of shaft 100 is preferably bent to improve access to the operative site of the tissue being treated. Electrode support member 102 has a substantially planar tissue treatment surface 212 (FIG. 4) that is usually at an angle of about 10 degrees to 90 degrees relative to the longitudinal axis of shaft 100, preferably about 30 degrees to 60 degrees and more preferably about 45 degrees. In alternative embodiments, the distal portion of shaft 100 comprises a flexible material which can be deflected relative to the longitudinal axis of the shaft. Such deflection may be selectively induced by mechanical tension of a pull wire, for example, or by a shape memory wire that expands or contracts by externally applied temperature changes. A more complete description of this embodiment can be found in U.S. Pat. No. 5,697,909, the complete disclosure of which is incorporated herein by reference.

Alternatively, shaft 100 of the present invention may be bent by the physician to the appropriate angle using a conventional bending tool or the like.

Figure 6A:
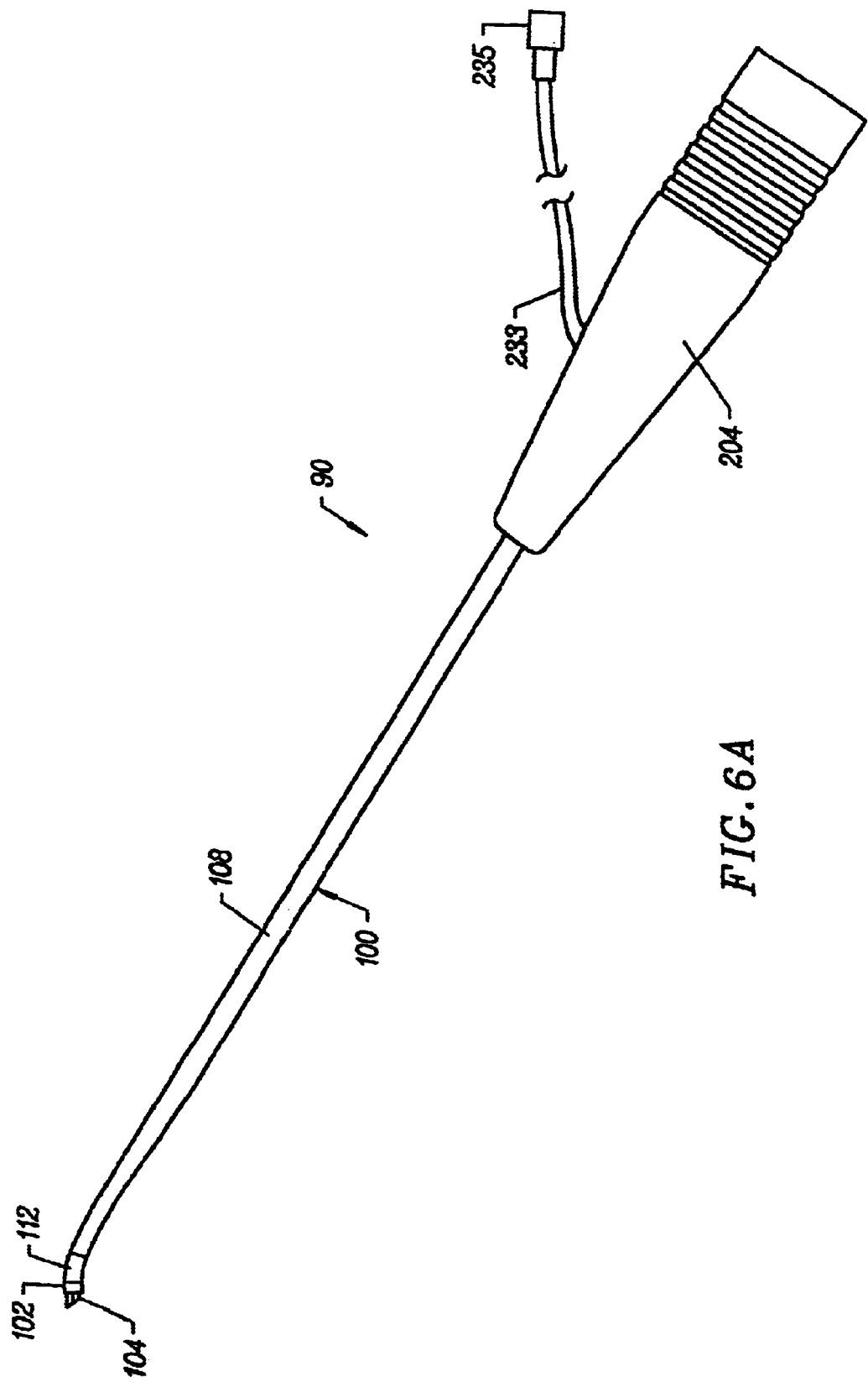
FIGS. 6A and 6B are perspective and end views, respectively, of an alternative electrosurgical probe incorporating an inner fluid lumen.
Figure 6B:
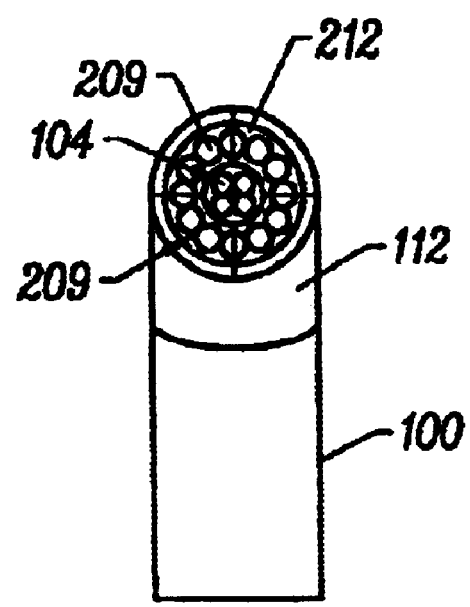

In the embodiment shown in FIGS. 4 to 6, probe 20 includes a return electrode 112 for completing the current path between active electrodes 104 and a high frequency power supply 28 (see FIG. 1). As shown, return electrode 112 preferably comprises an exposed portion of shaft 100 shaped as an annular conductive band near the distal end of shaft 100 slightly proximal to tissue treatment surface 212 of electrode support member 102, typically about 0.5 mm to 10 mm and more preferably about 1 mm to 10 mm. Return electrode 112 or shaft 100 is coupled to a connector 258 (FIG. 5) that extends to the proximal end of probe 10, where it is suitably connected to power supply 28 (FIG. 1).

As shown in FIG. 3, return electrode 112 is not directly connected to active electrodes 104. To complete a current path so that active electrodes 104 are electrically connected to return electrode 112, an electrically conductive fluid (e.g., isotonic saline) is positioned, or caused to flow, therebetween. In the representative embodiment, the electrically conductive fluid is delivered through fluid tube 233 to opening 237, as described above. Alternatively, the conductive fluid may be delivered by a fluid delivery element (not shown) that is separate from probe 20. In arthroscopic surgery, for example, the joint cavity will be flooded with isotonic saline and the probe 20 will be introduced into this flooded joint cavity. Electrically conductive fluid can be continually resupplied to maintain the conduction path between return electrode 112 and active electrodes 104. In other embodiments, the distal portion of probe 20 may be dipped into a source of electrically conductive fluid, such as a gel or isotonic saline, prior to positioning the probe distal portion at the target site. Applicant has found that the surface tension of the fluid and/or the viscous nature of a gel allows the conductive fluid to remain around the active and return electrodes for long enough to complete its function according to the present invention, as described below. Alternatively, the conductive fluid, such as a gel, may be applied directly to the target site.

Figure 7A:
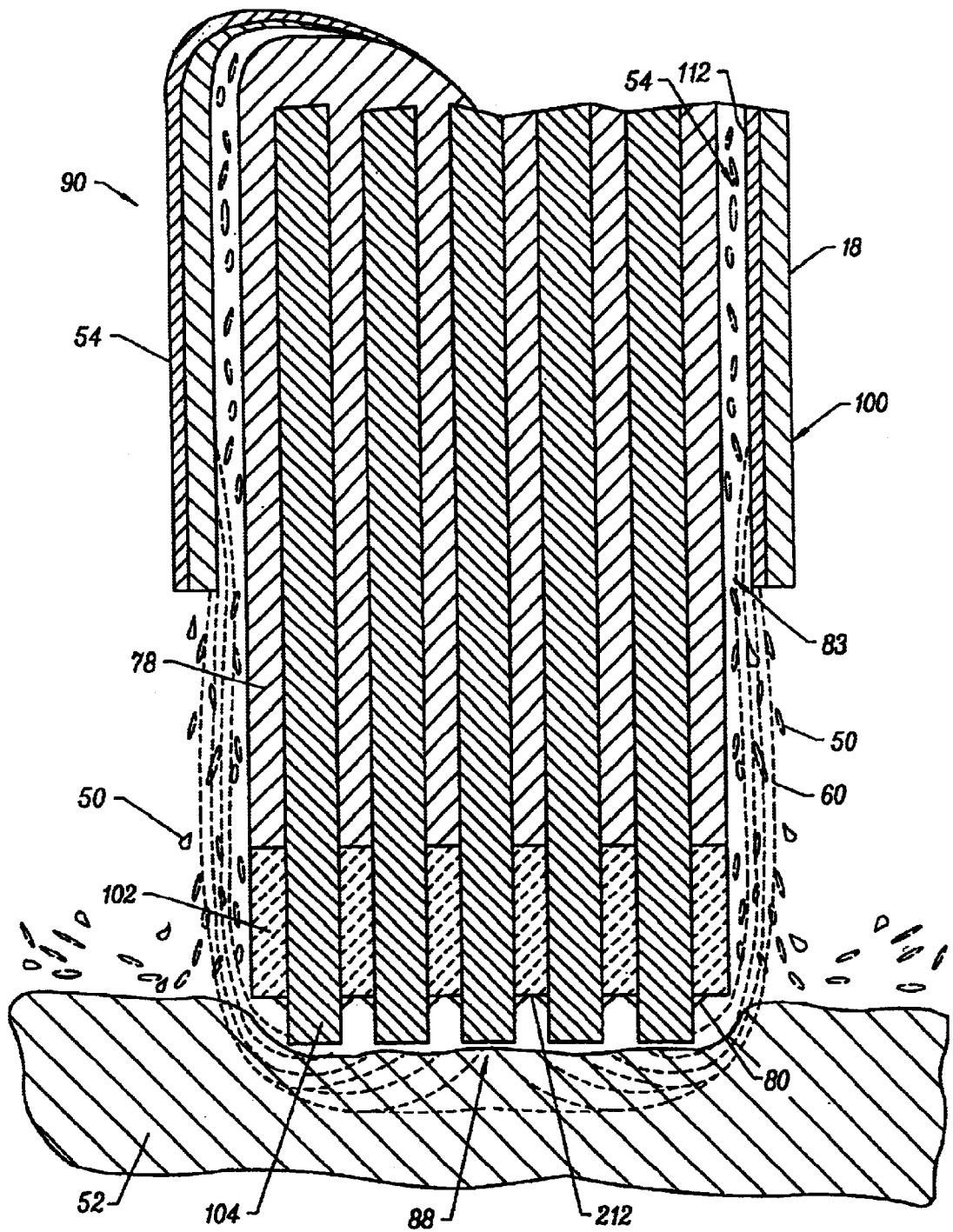

In alternative embodiments, the fluid path may be formed in probe 20 by, for example, an inner lumen or an annular gap between the return electrode and a tubular support member within shaft 100 (see FIGS. 7A and 7B). This annular gap may be formed near the perimeter of the shaft 100 such that the electrically conductive fluid tends to flow radially inward towards the target site, or it may be formed towards the center of shaft 100 so that the fluid flows radially outward. In both of these embodiments, a fluid source (e.g., a bag of fluid elevated above the surgical site or having a pumping device), is coupled to probe 20 via a fluid supply tube (not shown) that may or may not have a controllable valve. A more complete description of an electrosurgical probe incorporating one or more fluid lumen(s) can be found in U.S. Pat. No. 5,697,281, the complete disclosure of which is incorporated herein by reference.

Referring to FIG. 4, the electrically isolated active electrodes 104 are spaced apart over tissue treatment surface 212 of electrode support member 102. The tissue treatment surface and individual active electrodes 104 will usually have dimensions within the ranges set forth above. In the representative embodiment, the tissue treatment surface 212 has a circular cross-sectional shape with a diameter in the range of 1 mm to 20 mm. The individual active electrodes 104 preferably extend from tissue treatment surface 212 by a distance of about 0.1 mm to 4 mm, usually about 0.2 mm to 2 mm. Applicant has found that this configuration increases the high electric field intensities and associated current densities around active electrodes 104 to facilitate the ablation and shrinkage of tissue as described in detail above.

In the embodiment of FIGS. 3 to 5, the probe includes a single, larger opening 209 in the center of tissue treatment surface 212, and a plurality of active electrodes (e.g., about 3–15) around the perimeter of surface 212 (see FIG. 4). Alternatively, the probe may include a single, annular, or partially annular, active electrode at the perimeter of the tissue treatment surface. The central opening 209 is coupled to a suction lumen (not shown) within shaft 100 and a suction tube 211 (FIG. 3) for aspirating tissue, fluids and/or gases from the target site. In this embodiment, the electrically conductive fluid generally flows radially inward past active electrodes 104 and then back through the opening 209. Aspirating the electrically conductive fluid during surgery allows the surgeon to see the target site, and it prevents the fluid from flowing into the patient's body.

Of course, it will be recognized that the distal tip of probe may have a variety of different configurations. For example, the probe may include a plurality of openings 209 around the outer perimeter of tissue treatment surface 212 (see FIG. 6B). In this embodiment, the active electrodes 104 extend distally from the center of tissue treatment surface 212 such that they are located radially inward from openings 209. The openings are suitably coupled to fluid tube 233 for delivering electrically conductive fluid to the target site, and suction tube 211 for aspirating the fluid after it has completed the conductive path between the return electrode 112 and the active electrodes 104.

FIG. 5 illustrates the electrical connections 250 within handle 204 for coupling active electrodes 104 and return electrode 112 to the power supply 28. As shown, a plurality of wires 252 extend through shaft 100 to couple active electrodes 104 to a plurality of pins 254, which are plugged into a connector block 256 for coupling to a connecting cable 22 (FIG. 1). Similarly, return electrode 112 is coupled to connector block 256 via a wire 258 and a plug 260.

According to the present invention, the probe 20 further includes an identification element that is characteristic of the particular electrode assembly so that the same power supply 28 can be used for different electrosurgical operations. In one embodiment, for example, the probe 20 includes a voltage reduction element or a voltage reduction circuit for reducing the voltage applied between the active electrodes 104 and the return electrode 112. The voltage reduction element serves to reduce the voltage applied by the power supply so that the voltage between the active electrodes and the return electrode is low enough to avoid excessive power dissipation into the electrically conductive medium and/or ablation of the tissue at the target site. In some embodiments, the voltage reduction element allows the power supply 28 to apply two different voltages simultaneously to two different electrodes (see FIG. 14D). In other embodiments, the voltage reduction element primarily allows the electrosurgical probe 20/90 to be compatible with other power supply units (for example, various electrosurgical power supply units manufactured by ArthroCare Corporation, Sunnyvale, Calif.) that are adapted to apply higher voltages for ablation or vaporization of tissue. For thermal heating or coagulation of tissue, for example, the voltage reduction element will serve to reduce a voltage of about 100 volts RMS to 170 volts RMS (which is a setting of 1 or 2 on the ArthroCare Model 970 and 2000 Generators (ArthroCare Corporation, Sunnyvale, Calif.)) to about 45 volts RMS to 60 volts RMS, which is a suitable voltage for coagulation of tissue without ablation (e.g., molecular dissociation) of the tissue.

Of course, for some procedures, the probe will typically not require a voltage reduction element. Alternatively, the probe may include a voltage increasing element or circuit, if desired. Alternatively or additionally, the cable 22 that couples the power supply 28 to the probe 20/90 may be used as a voltage reduction element. The cable has an inherent capacitance that can be used to reduce the power supply voltage if the cable is placed into the electrical circuit between the power supply, the active electrodes and the return electrode. In this embodiment, the cable 22 may be used alone, or in combination with one of the voltage reduction elements discussed above, e.g., a capacitor. Further, it should be noted that the present invention can be used with a power supply that is adapted to apply a voltage within the selected range for treatment of tissue. In this embodiment, a voltage reduction element or circuitry may not be desired.

Figure 7C:
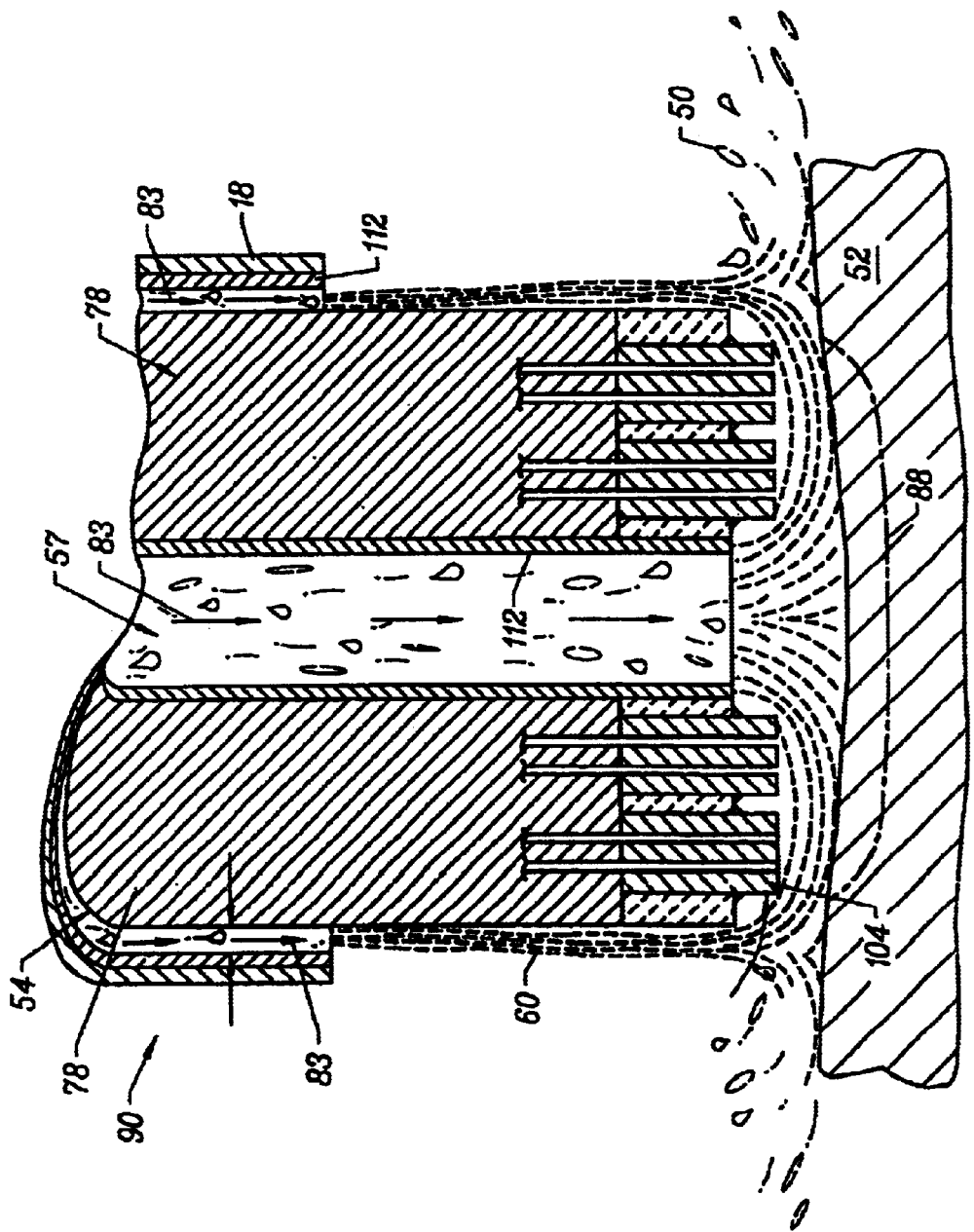

FIGS. 7A–7C schematically illustrate the distal portion of three different embodiments of probe 90 according to the present invention. As shown in 8A, active electrodes 104 are anchored in electrode support 102. Electrode support 102 may comprise a matrix of suitable insulating material (e.g., a silicone rubber, a ceramic, or glass material, such as alumina, zirconia and the like) which could be formed at the time of manufacture in a flat, hemispherical or other shape according to the requirements of a particular procedure. In one embodiment, the support matrix material is alumina (available from Kyocera Industrial Ceramics Corporation, Elkgrove, Ill.). Alumina has the advantages of high thermal conductivity, good electrically insulative properties, high flexural modulus. resistance to carbon tracking. biocompatibility, and high melting point. The support 102 is adhesively joined to a tubular support member 78 that extends most or all of the distance between support 102 and the proximal end of probe 90. Tubular member 78 preferably comprises an electrically insulating material, such as an epoxy or silicone-based material.

In a preferred construction technique, active electrodes 104 extend through pre-formed openings in the support 102 so that they protrude above tissue treatment surface 212 by the desired distance. The electrodes are then bonded to the tissue treatment surface 212 of support 102, typically by an inorganic sealing material 80. Sealing material 80 is selected to provide effective electrical insulation, and good adhesion to both alumina support 102 and the platinum or titanium active electrodes. Sealing material 80 additionally should have a compatible thermal expansion coefficient and a melting point well below that of platinum or titanium and alumina or zirconia, typically being a glass or glass ceramic.

In the embodiment shown in FIG. 7A, return electrode 112 comprises an annular member positioned around the exterior of shaft 100 of probe 90. Return electrode 112 may fully or partially circumscribe tubular support member 78 to form an annular gap 54 therebetween for flow of electrically conductive liquid 50 therethrough, as discussed below. Gap 54 preferably has a width in the range of 0.25 mm to 4 mm. Alternatively, probe may include a plurality of longitudinal ribs between tubular support member 78 and return electrode 112 to form a plurality of fluid lumens extending along the perimeter of shaft 100. In this embodiment, the plurality of lumens will extend to a plurality of openings.

Return electrode 112 is disposed within an electrically insulative jacket 18, which is typically formed as one or more electrically insulative sheaths or coatings, such as polytetrafluoroethylene, polyamide, and the like. The provision of the electrically insulative jacket 18 over return electrode 112 prevents direct electrical contact between return electrode 112 and any adjacent, non-target tissue or body structure. Such direct electrical contact between a body structure and an exposed electrode member 112 could result in unwanted heating and necrosis of the non-target structure at the point of contact.

As shown in FIG. 7A, return electrode 112 is not directly connected to active electrodes 104. To complete this current path so that terminals 104 are electrically connected to return electrode 112, electrically conductive liquid 50 (e.g., isotonic saline) is caused to flow along fluid path(s) 83. Fluid path 83 is formed by annular gap 54 between outer return electrode 112 and tubular support member 78. The electrically conductive liquid 50 flowing through fluid path 83 provides a pathway for electrical current flow between active electrodes 104 and return electrode 112, as illustrated by the current flux lines 60 in FIG. 7A. When a voltage is applied between active electrodes 104 and return electrode 112, high electric field intensities will be generated at the distal tips of active electrodes 104 with current flow from active electrodes 104 through the target tissue to return electrode 112, the high electric field intensities causing ablation of tissue 52 in zone 88.

FIG. 7B illustrates another alternative embodiment of electrosurgical probe 90 which has a return electrode 112 positioned within tubular member 78. Return electrode 112 is preferably substantially cylindrical defining an inner lumen 57 for allowing electrically conductive liquid 50 (e.g., isotonic saline) to flow therethrough in electrical contact with return electrode 112. In this embodiment, a voltage difference is applied between active electrodes 104 and return electrode 112 resulting in electrical current flow through the electrically conductive liquid 50 as shown by current flux lines 60. As a result of the applied voltage and concomitant high electric field intensities at the tips of active electrodes 104, tissue 52 becomes ablated or transected in zone 88.

FIG. 7C illustrates another embodiment of probe 90 that is a combination of the embodiments in FIGS. 7A and 7B. As shown, this probe includes both an inner lumen 57 and an outer gap or plurality of outer lumens 54 for flow of electrically conductive fluid. In this embodiment, the return electrode 112 may be positioned within tubular member 78 as in FIG. 7B, outside of tubular member 78 as in FIG. 7A, or in both locations.

Figure 8:
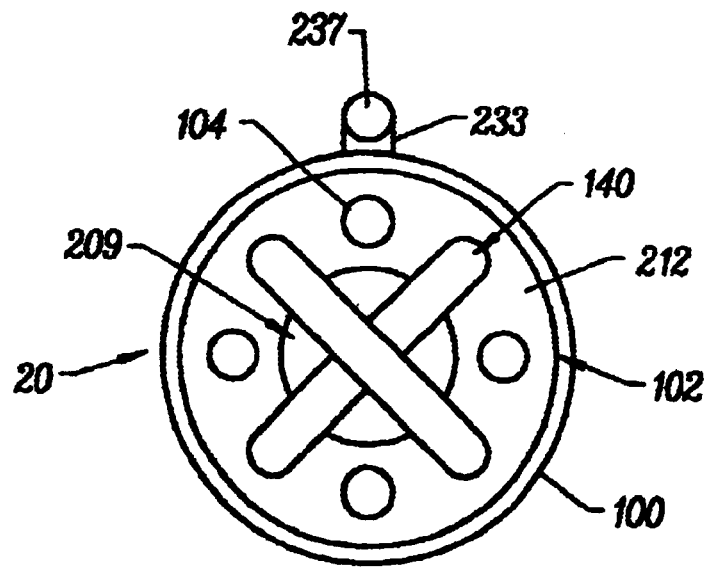
FIGS. 8–11 are end views of alternative embodiments of the probe of FIG. 3, incorporating aspiration electrode(s)
Figure 12:
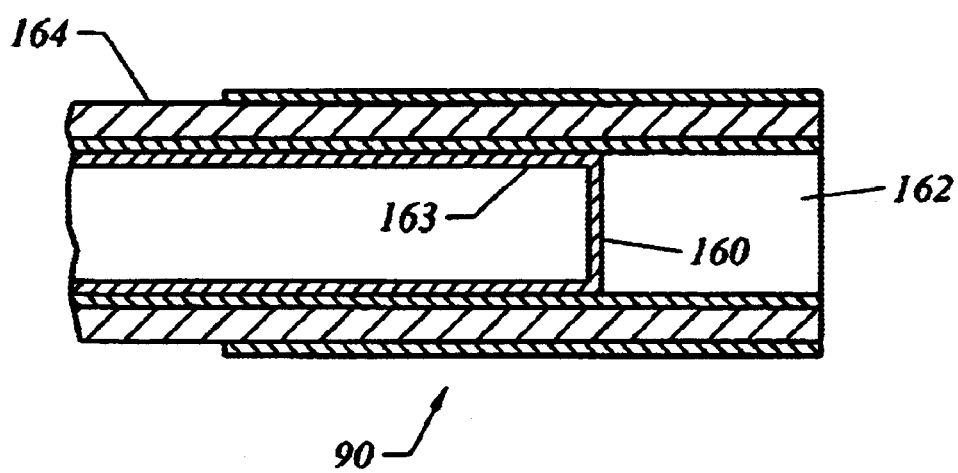
FIG. 12 shows a longitudinal section of the shaft distal portion of a probe having an aspiration electrode within an aspiration lumen, according to another embodiment of the present invention.

In some embodiments, the probe 20/90 will also include one or more aspiration electrode(s) coupled to the aspiration lumen for inhibiting clogging during aspiration of tissue fragments from the surgical site. As shown in FIG. 8, one or more of the active electrodes 104 may comprise loop electrodes 140 that extend across distal opening 209 of the suction lumen within shaft 100. In the representative embodiment, two of the active electrodes 104 comprise loop electrodes 140 that cross over the distal opening 209. Of course, it will be recognized that a variety of different configurations are possible, such as a single loop electrode, or multiple loop electrodes having different configurations than shown. In addition, the electrodes may have shapes other than loops, such as the coiled configurations shown in FIGS. 9 and 10. Alternatively, the electrodes may be formed within suction lumen proximal to the distal opening 209, as shown in FIG. 12. The main function of loop electrodes 140 is to ablate portions of tissue that are drawn into the suction lumen to prevent clogging of the lumen.

In some embodiments, loop electrodes 140 are electrically isolated from the other active electrodes 104. In other embodiments, the loop electrodes 140 and active electrodes 104 may be electrically connected to each other such that both are activated together. Loop electrodes 140 may or may not be electrically isolated from each other. Loop electrodes 140 will usually extend only about 0.05 mm to 4 mm, preferably about 0.1 mm to 1 mm, from the tissue treatment surface of electrode support member 102.

Figure 9:
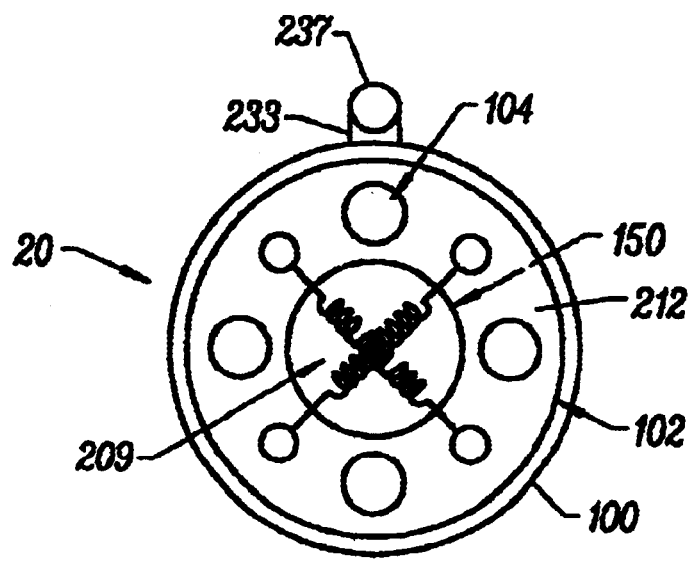
Figure 10:
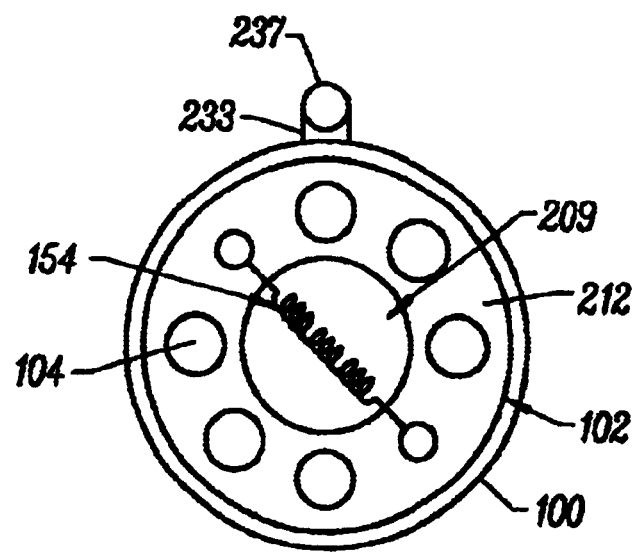

Referring now to FIGS. 9 and 10, alternative embodiments for aspiration electrodes will now be described. As shown in FIG. 9, the aspiration electrodes may comprise a pair of coiled electrodes 150 that extend across distal opening 209 of the suction lumen. The larger surface area of the coiled electrodes 150 usually increases the effectiveness of the electrodes 150 in ablating or digesting tissue fragments passing through opening 209. In FIG. 10, the aspiration electrode comprises a single coiled electrode 154 passing across the distal opening 209 of suction lumen. This single electrode 154 may be sufficient to inhibit clogging of the suction lumen. Alternatively, the aspiration electrodes may be positioned within the suction lumen proximal to the distal opening 209. Preferably, these electrodes are close to opening 209 so that tissue does not clog the opening 209 before it reaches electrode 154. In this embodiment, a separate return electrode 156 (not shown) may be provided within the suction lumen to confine the electric currents therein.

Referring to FIG. 12, another embodiment of the present invention incorporates an aspiration electrode 160 within the aspiration lumen 162 of the probe. As shown, the electrode 160 is positioned just proximal of distal opening 209 so that the tissue fragments are ablated as they enter lumen 162. In the representative embodiment, the aspiration electrode 160 comprises a loop electrode that extends across the aspiration lumen 162. However, it will be recognized that many other configurations are possible. In this embodiment, the return electrode 164 is located on the exterior of the probe as in the previously described embodiments. Alternatively, the return electrode(s) may be located within the aspiration lumen 162 with the aspiration electrode 160. For example, inner insulating coating 163 may be exposed at portions within the lumen 162 to provide a conductive path between this exposed portion of return electrode 164 and the aspiration electrode 160. The latter embodiment has the advantage of confining the electric currents to within the aspiration lumen. In addition, in dry fields in which the conductive fluid is delivered to the target site, it is usually easier to maintain a conductive fluid path between the active and return electrodes in the latter embodiment because the conductive fluid is aspirated through the aspiration lumen 162 along with the tissue fragments.

Figure 11:
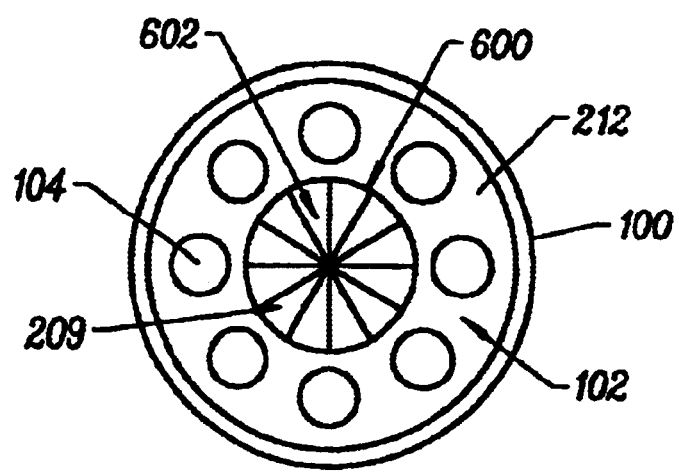

Referring to FIG. 11, another embodiment of the present invention incorporates a wire mesh electrode 600 extending across the distal portion of aspiration lumen 162. As shown, mesh electrode 600 includes a plurality of openings 602 to allow fluids and tissue fragments to flow through into aspiration lumen 162. The size of the openings 602 will vary depending on a variety of factors. The mesh electrode may be coupled to the distal or proximal surfaces of support member 102. Wire mesh electrode 600 comprises a conductive material, such as titanium, tantalum, steel, stainless steel, tungsten, copper, or gold, and the like. In the representative embodiment, wire mesh electrode 600 comprises a different material, having a different electric potential, than the active electrode(s) 104. In one embodiment, mesh electrode 600 comprises steel, and active electrode(s) comprises tungsten. Applicant has found that a slight variance in the electrochemical potential of mesh electrode 600 and active electrode(s) 104 improves the performance of the device. Of course, it will be recognized that the mesh electrode may be electrically insulated from active electrode(s) as in previous embodiments Referring now to FIGS. 13A–13C, an alternative embodiment incorporating a metal screen 610 is illustrated. As shown, metal screen 610 has a plurality of peripheral openings 612 for receiving active electrodes 104, and a plurality of inner openings 614 for allowing aspiration of fluid and tissue through opening 609 of the aspiration lumen. As shown, screen 610 is press fitted over active electrodes 104 and then adhered to shaft 100 of probe 20. Similar to the mesh electrode embodiment, metal screen 610 may comprise a variety of conductive metals, such as titanium, tantalum, steel, stainless steel, tungsten, copper, gold or the like. In the representative embodiment, metal screen 610 is coupled directly to, or integral with, active electrode(s) 104. In this embodiment, the active electrode(s) 104 and the metal screen 610 are electrically coupled to each other.

Figure 14A:
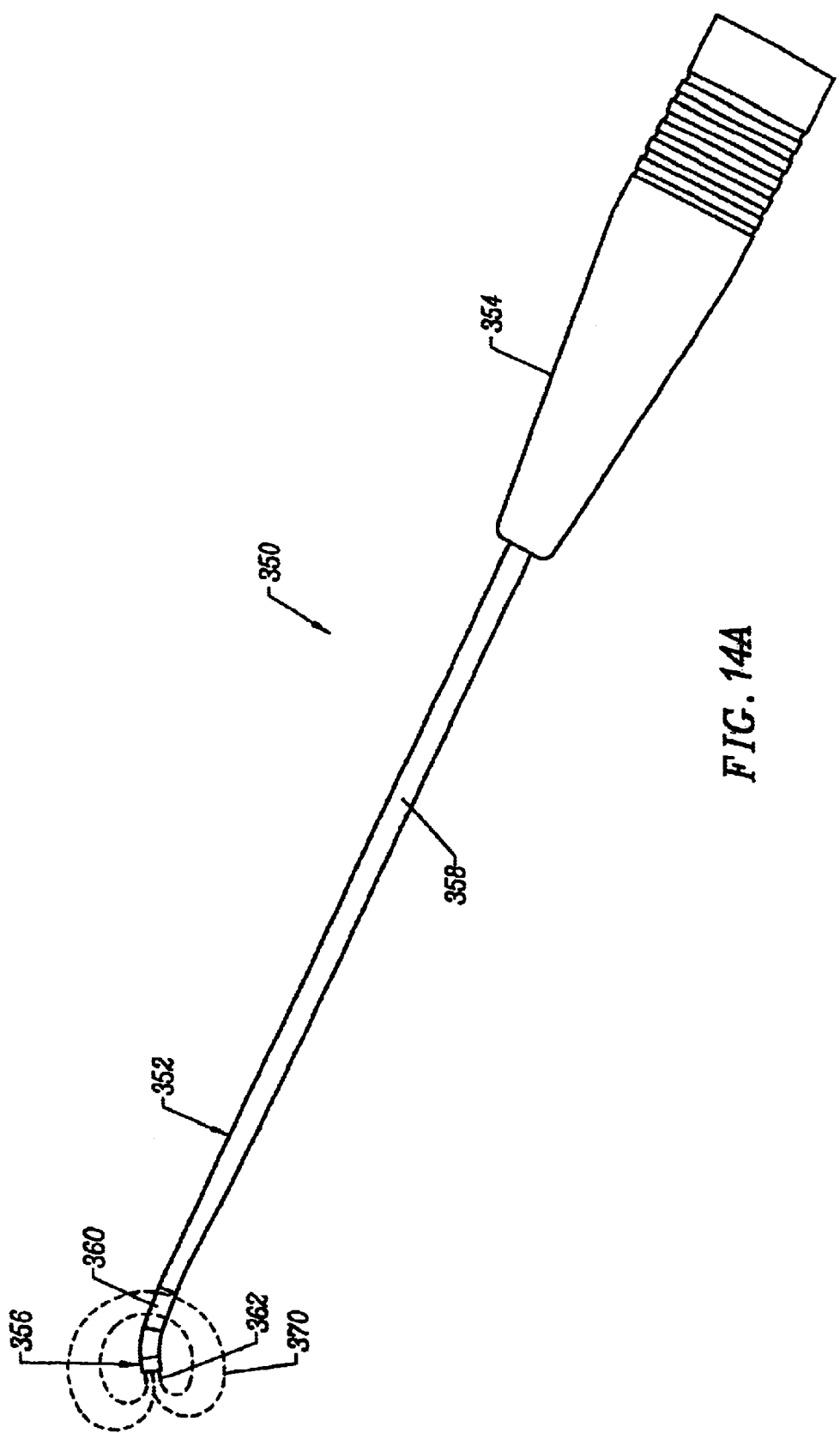
FIGS. 14A–14D illustrate four embodiments of electrosurgical probes specifically designed for treating spinal defects.

FIGS. 14A to 14D illustrate embodiments of an electrosurgical probe 350 specifically designed for the treatment of herniated or diseased spinal discs. Referring to FIG. 14A, probe 350 comprises an electrically conductive shaft 352, a handle 354 coupled to the proximal end of shaft 352 and an electrically insulating support member 356 at the distal end of shaft 352. Probe 350 further includes a shrink wrapped insulating sleeve 358 over shaft 352, and an exposed portion of shaft 352 that functions as the return electrode 360. In the representative embodiment, probe 350 comprises a plurality of active electrodes 362 extending from the distal end of support member 356. As shown, return electrode 360 is spaced a further distance from active electrodes 362 than in the embodiments described above. In this embodiment, the return electrode 360 is spaced a distance of about 2.0 mm to 50 mm, preferably about 5 mm to 25 mm. In addition, return electrode 360 has a larger exposed surface area than in previous embodiments, having a length in the range of about 2.0 mm to 40 mm, preferably about 5 mm to 20 mm. Accordingly, electric current passing from active electrodes 362 to return electrode 360 will follow a current flow path 370 that is further away from shaft 352 than in the previous embodiments. In some applications, this current flow path 370 results in a deeper current penetration into the surrounding tissue with the same voltage level, and thus increased thermal heating of the tissue. As discussed above, this increased thermal heating may have advantages in some applications of treating disc or other spinal defects or disorders. Typically, it is desired to achieve a tissue temperature in the range of about 60° C. to 100° C. to a depth of about 0.2 mm to 5 mm, usually about 1 mm to 2 mm. The voltage required for this thermal heating will partly depend on the electrode configurations, the conductivity of the tissue and the area immediately surrounding the electrodes, the time period in which the voltage is applied, and the depth of tissue heating desired. With the electrode configurations described in FIGS. 14A–14D, the voltage level for thermal heating will usually be in the range of about 20 volts RMS to 300 volts RMS, and preferably about 60 volts RMS to 200 volts RMS. The peak-to-peak voltages for thermal heating with a square wave form having a crest factor of about 2 are typically in the range of about 40 to 600 volts peak-to-peak, preferably about 120 to 400 volts peak-to-peak. The higher the voltage is within this range, the less time required. If the voltage is too high, however, the surface tissue may be vaporized, debulked or ablated, which is undesirable in certain procedures.

In alternative embodiments, the electrosurgical system used in conjunction with probe 350 may include a dispersive return electrode 450 (see FIG. 15) which allows for switching between bipolar and monopolar modes. In this embodiment, the system will switch between an ablation mode, where the dispersive pad 450 is deactivated and voltage is applied between active and return electrodes 362, 360, and a subablation or thermal heating mode, where the active electrode(s) 362 are deactivated and voltage is applied between the dispersive pad 450 and the return electrode 360. In the subablation mode, a lower voltage is typically applied and the return electrode 360 functions as the active electrode to provide thermal heating and/or coagulation of tissue surrounding return electrode 360.

Figure 14B:
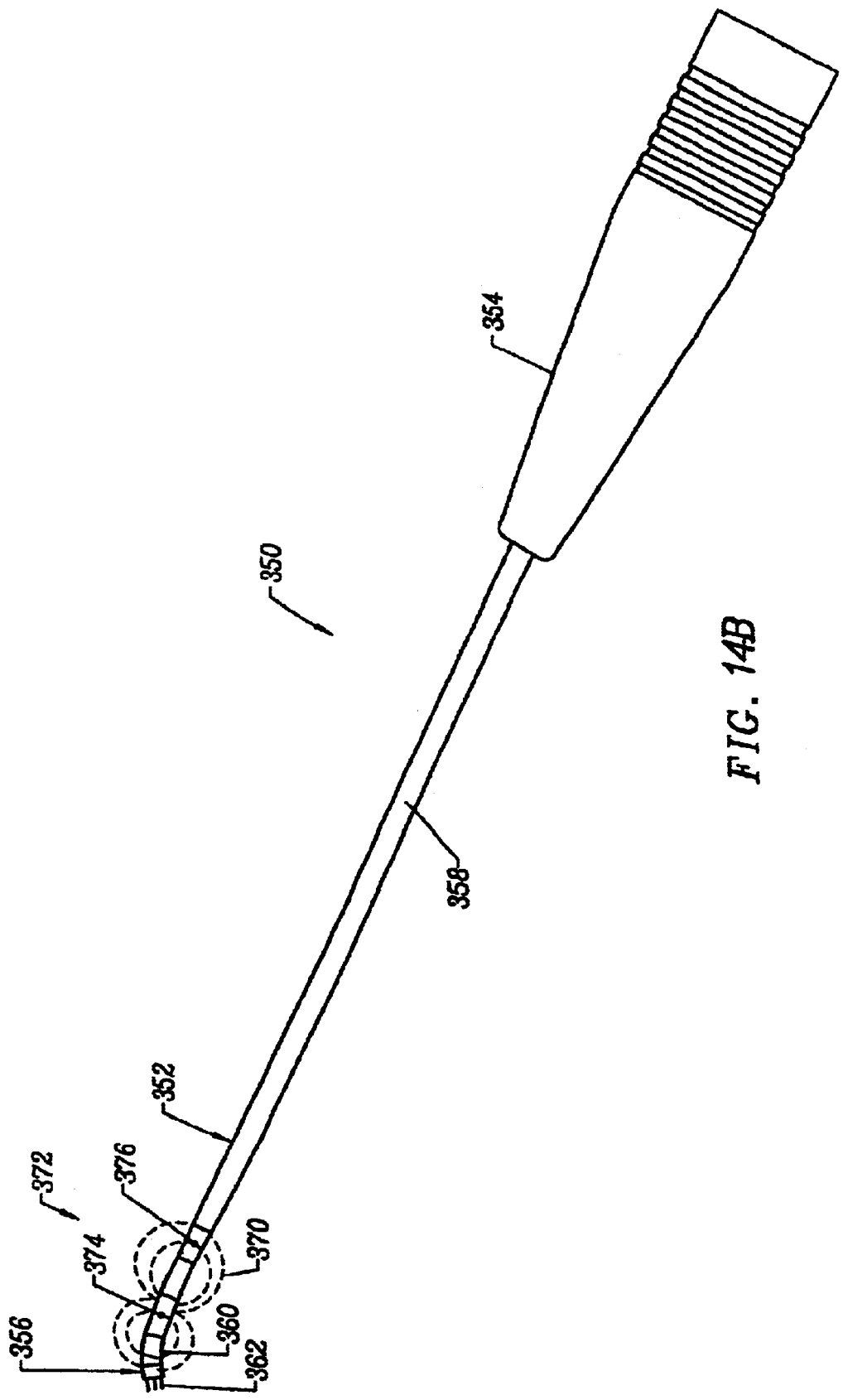

FIG. 14B illustrates yet another embodiment of the present invention. As shown, electrosurgical probe 350 comprises an electrode assembly 372 having one or more active electrode(s) 362 and a proximally spaced return electrode 360 as in previous embodiments. Return electrode 360 is typically spaced about 0.5 mm to 25 mm, preferably 1.0 mm to 5.0 mm from the active electrode(s) 362, and has an exposed length of about 1 mm to 20 mm. In addition, electrode assembly 372 includes two additional electrodes 374, 376 spaced axially on either side of return electrode 360. Electrodes 374, 376 are typically spaced about 0.5 mm to 25 mm, preferably about 1 mm to 5 mm from return electrode 360. In the representative embodiment, the additional electrodes 374, 376 are exposed portions of shaft 352, and the return electrode 360 is electrically insulated from shaft 352 such that a voltage difference may be applied between electrodes 374, 376 and electrode 360. In this embodiment, probe 350 may be used in at least two different modes, an ablation mode and a subablation or thermal heating mode. In the ablation mode, voltage is applied between active electrode(s) 362 and return electrode 360 in the presence of electrically conductive fluid, as described above. In the ablation mode, electrodes 374, 376 are deactivated. In the thermal heating or coagulation mode, active electrode(s) 362 are deactivated and a voltage difference is applied between electrodes 374, 376 and electrode 360 such that a high frequency current 370 flows therebetween, as shown in FIG. 14B. In the thermal heating mode, a lower voltage is typically applied, such that the applied voltage is below the threshold for plasma formation and ablation, but sufficient to cause some thermal effect on the tissue immediately surrounding the electrodes without vaporizing or otherwise debulking this tissue, so that the current 370 provides thermal heating and/or coagulation of tissue surrounding electrodes 360, 372, 374.

Figure 14C:
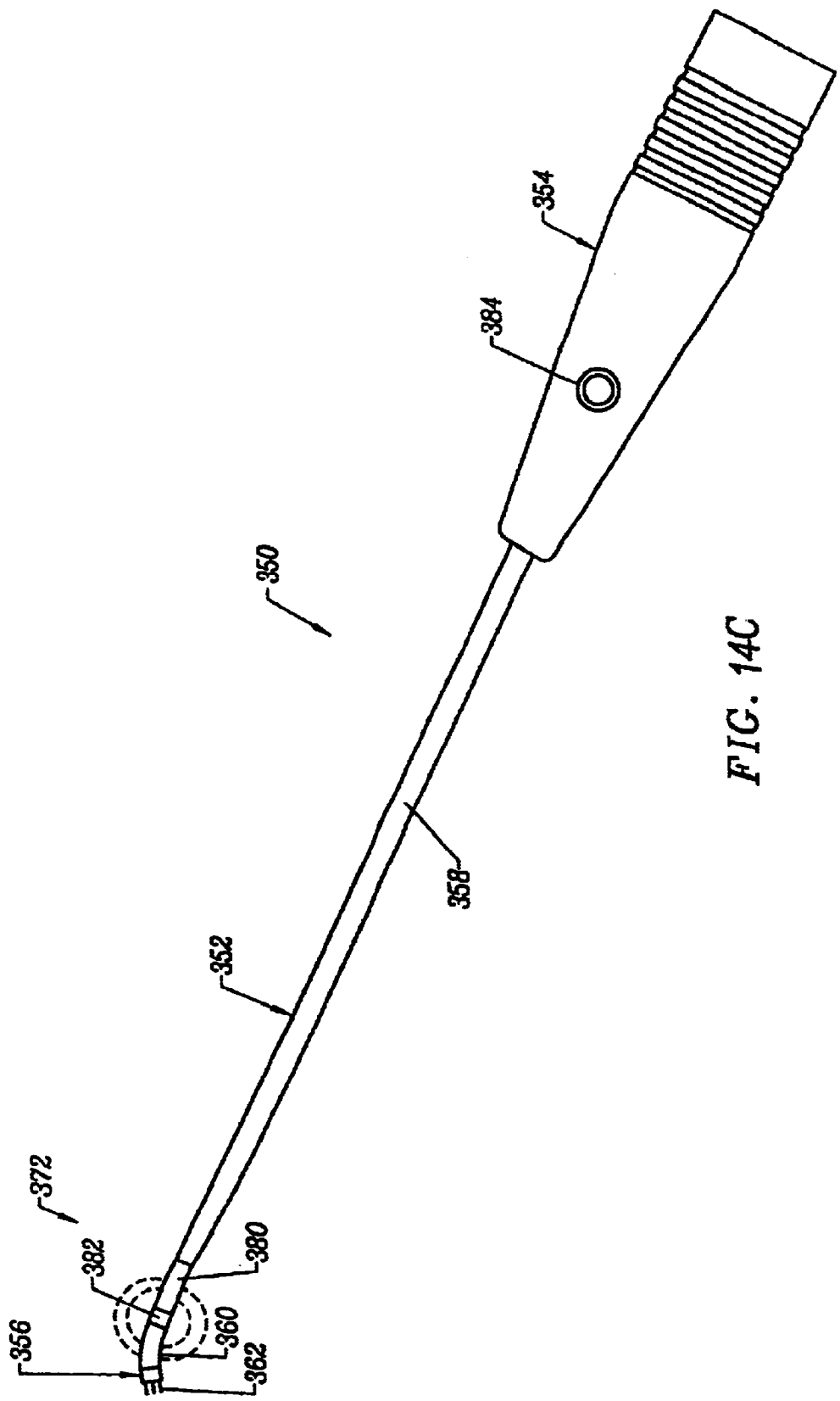

FIG. 14C illustrates another embodiment of probe 350 incorporating an electrode assembly 372 having one or more active electrode(s) 362 and a proximally spaced return electrode 360 as in previous embodiments. Return electrode 360 is typically spaced about 0.5 mm to 25 mm, preferably 1.0 mm to 5.0 mm from the active electrode(s) 362, and has an exposed length of about 1 mm to 20 mm. In addition, electrode assembly 372 includes a second active electrode 380 separated from return electrode 360 by an electrically insulating spacer 382. In this embodiment, handle 354 includes a switch 384 for toggling probe 350 between at least two different modes, an ablation mode and a subablation or thermal heating mode. In the ablation mode, voltage is applied between active electrode(s) 362 and return electrode 360 in the presence of electrically conductive fluid, as described above. In the ablation mode, electrode 380 is deactivated. In the thermal heating or coagulation mode, active electrode(s) 362 may be deactivated and a voltage difference is applied between electrode 380 and electrode 360 such that a high frequency current 370 flows therebetween. Alternatively, active electrode(s) 362 may not be deactivated as the higher resistance of the smaller electrodes may automatically send the electric current to electrode 380 without having to physically decouple electrode(s) 362 from the circuit. In the thermal heating mode, a lower voltage is typically applied below the threshold for plasma formation and ablation, but sufficient to cause some thermal effect on the tissue immediately surrounding the electrodes without vaporizing or otherwise debulking this tissue so that the current 370 provides thermal heating and/or coagulation of tissue surrounding electrodes 360, 380.

Of course, it will be recognized that a variety of other embodiments may be used to accomplish similar functions as the embodiments described above. For example, electrosurgical probe 350 may include a plurality of helical bands formed around shaft 352, with one or more of the helical bands having an electrode coupled to the portion of the band such that one or more electrodes are formed on shaft 352 spaced axially from each other.

Figure 14D:
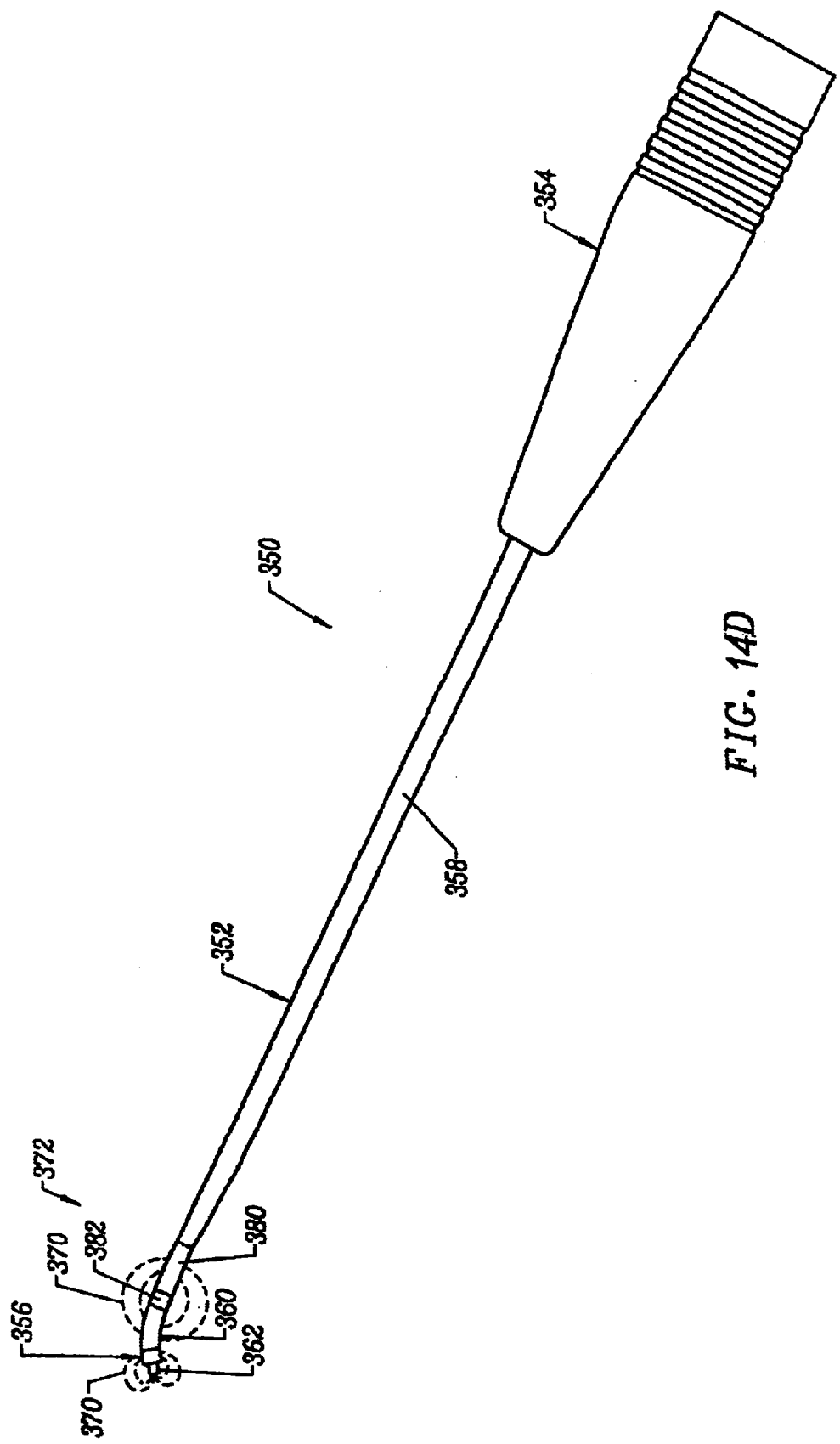

FIG. 14D illustrates another embodiment of the invention designed for channeling through tissue and creating lesions therein to treat spinal discs and/or snoring and sleep apnea. As shown, probe 350 is similar to the probe in FIG. 14C having a return electrode 360 and a third, coagulation electrode 380 spaced proximally from the return electrode 360. In this embodiment, active electrode 362 comprises a single electrode wire extending distally from insulating support member 356. Of course, the active electrode 362 may have a variety of configurations to increase the current densities on its surfaces, e.g., a conical shape tapering to a distal point, a hollow cylinder, loop electrode and the like. In the representative embodiment, support member 356 and spacer 382 are constructed of an electrically insulating material, such as a ceramic, a glass, a silicone rubber, and the like. The proximal insulating spacer 382 may alternatively comprise a more conventional organic insulating material, as this support member 382 will generally not be in the presence of a plasma that would otherwise etch or wear away an organic material.

The probe 350 in FIG. 14D does not include a switching element. In this embodiment, all three electrodes are activated when the power supply is activated. The return electrode 360 has an opposite polarity from the active and coagulation electrodes 362, 380 such that current 370 flows from the latter electrodes to the return electrode 360 as shown. In the preferred embodiment, the electrosurgical system includes a voltage reduction element or a voltage reduction circuit for reducing the voltage applied between the coagulation electrode 380 and return electrode 360. The voltage reduction element allows the power supply 28 to, in effect, apply two different voltages simultaneously to two different electrodes. Thus, for channeling through tissue, the operator may apply a voltage sufficient to provide ablation of the tissue at the tip of the probe (i.e., tissue adjacent to the active electrode 362). At the same time, the voltage applied to the coagulation electrode 380 will be insufficient to ablate tissue. For thermal heating or coagulation of tissue, for example, the voltage reduction element will serve to reduce a voltage in the range of about 100–300 volts RMS to about 45–90 volts RMS, the latter generally representing a suitable voltage range for coagulation of tissue without ablation (e.g., molecular dissociation) of the tissue.

In the representative embodiment, the voltage reduction element comprises a pair of capacitors forming a bridge divider (not shown) coupled to the power supply and coagulation electrode 380. The capacitor usually has a capacitance of about 200 pF to 500 pF (at 500 volts), and preferably about 300 pF to 350 pF (at 500 volts). Of course, the capacitors may be located in other places within the system, such as in, or distributed along the length of, the cable, the generator, the connector, etc. In addition, it will be recognized that other voltage reduction elements, such as diodes, transistors, inductors, resistors, capacitors or combinations thereof, may be used in conjunction with the present invention. For example, the probe 350 may include a coded resistor (not shown) that is constructed to lower the voltage applied between the return and coagulation electrodes 360, 380. In addition, electrical circuits may be employed for this purpose.

Of course, for some procedures, the probe will typically not require a voltage reduction element. Alternatively, the probe may include a voltage increasing element or circuit, if desired. Alternatively or additionally, the cable 22 that couples the power supply 28 to the probe 90 may be used as a voltage reduction element. The cable has an inherent capacitance that can be used to reduce the power supply voltage if the cable is placed into the electrical circuit between the power supply, the active electrodes and the return electrode. In this embodiment, the cable 22 may be used alone, or in combination with one of the voltage reduction elements discussed above, e.g., a capacitor. Further, it should be noted that the present invention can be used with a power supply that is adapted to apply two different voltages within the selected range for treatment of tissue. In this embodiment, a voltage reduction element or circuitry may not be desired.

In one specific embodiment, the probe 350 is manufactured by first inserting an electrode wire (active electrode 362) through a ceramic tube (insulating support member 356) such that a distal portion of the wire extends through the distal portion of the tube, and bonding the wire to the tube, typically with an appropriate epoxy. A stainless steel tube (return electrode 360) is then placed over the proximal portion of the ceramic tube, and a wire (e.g., nickel wire) is bonded, typically by spot welding, to the inside surface of the stainless steel tube. The stainless steel tube is coupled to the ceramic tube by epoxy, and the device is cured in an oven or other suitable heat source. A second ceramic tube (insulating spacer member 382) is then placed inside the proximal portion of the stainless steel tube, and bonded in a similar manner. The shaft 352 is then bonded to the proximal portion of the second ceramic tube, and insulating sleeve 358 (e.g. polyimide) is wrapped around shaft 352 such that only a distal portion of the shaft is exposed (i.e., coagulation electrode 380). The nickel wire connection will extend through the center of shaft 352 to connect return electrode 360 to the power supply. The active electrode 362 may form a distal portion of shaft 352, or it may also have a connector extending through shaft 352 to the power supply.

In use, the physician positions active electrode 362 adjacent to the tissue surface to be treated (e.g., a spinal disc). The power supply is activated to provide an ablation voltage between active and return electrodes 362, 360 and a coagulation or thermal heating voltage between coagulation and return electrodes 380, 360. An electrically conductive fluid can then be provided around active electrode 362, and in the junction between the active and return electrodes 360, 362 to provide a current flow path therebetween. This may be accomplished in a variety of manners, as discussed above. The active electrode 362 is then advanced through the space left by the ablated tissue to form a channel in the disc. During ablation, the electric current between the coagulation and return electrode is typically insufficient to cause any damage to the surface of the tissue as these electrodes pass through the tissue surface into the channel created by active electrode 362. Once the physician has formed the channel to the appropriate depth, he or she will cease advancement of the active electrode, and will either hold the instrument in place for approximately 5 seconds to 30 seconds, or can immediately remove the distal tip of the instrument from the channel (see detailed discussion of this below). In either event, when the active electrode is no longer advancing, it will eventually stop ablating tissue.

Prior to entering the channel formed by the active electrode 362, an open circuit exists between return and coagulation electrodes 360, 380. Once coagulation electrode 380 enters this channel, electric current will flow from coagulation electrode 380, through the tissue surrounding the channel, to return electrode 360. This electric current will heat the tissue immediately surrounding the channel to coagulate any severed vessels at the surface of the channel. If the physician desires, the instrument may be held within the channel for a period of time to create a lesion around the channel, as discussed in more detail below.

Figure 15:
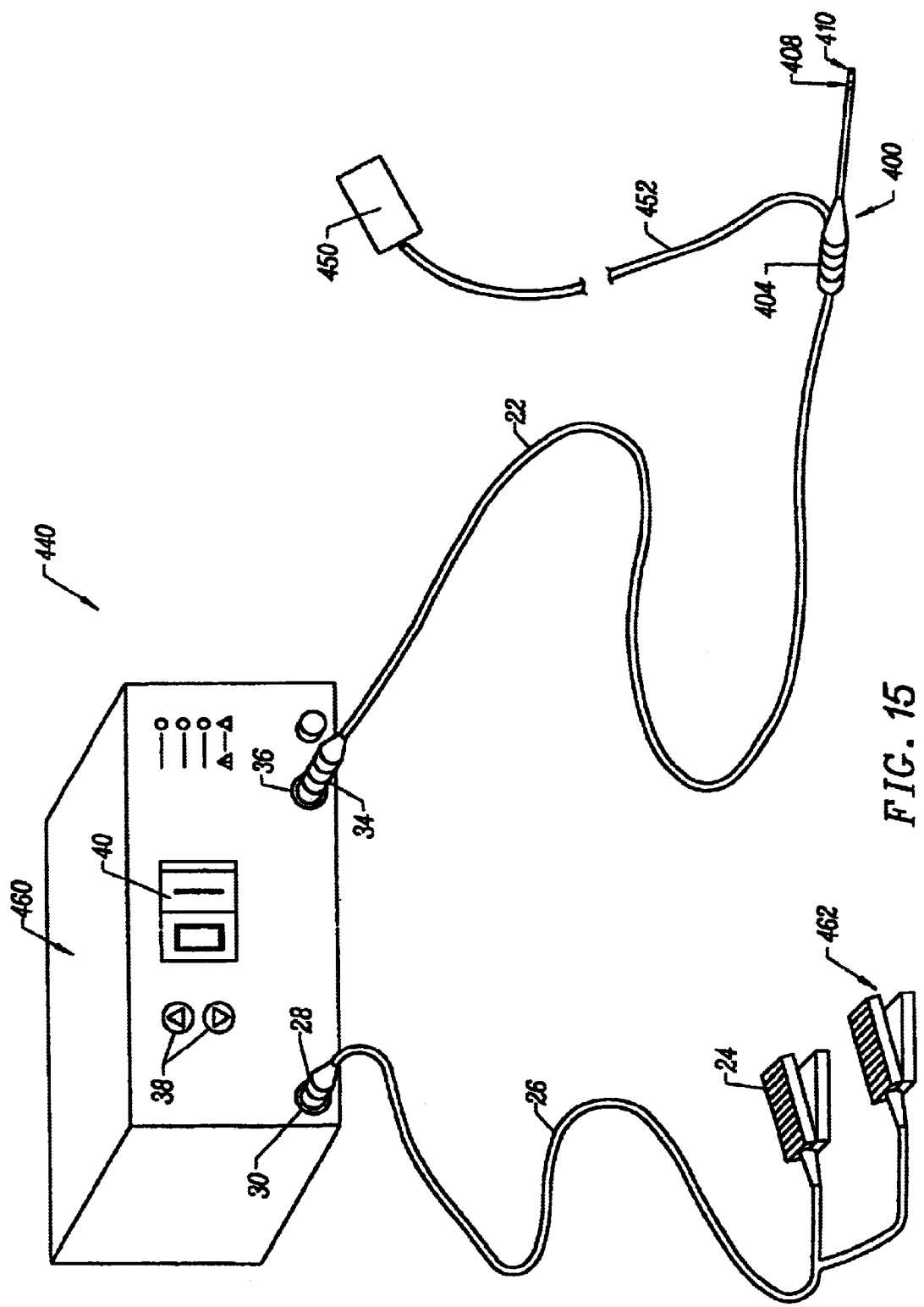
FIG. 15 illustrates an electrosurgical system incorporating a dispersive return pad for monopolar and/or bipolar operations.

FIG. 15 illustrates yet another embodiment of an electrosurgical system 440 incorporating a dispersive return pad 450 attached to the electrosurgical probe 400. In this embodiment, the invention functions in the bipolar mode as described above. In addition, the system 440 may function in a monopolar mode in which a high frequency voltage difference is applied between the active electrode(s) 410, and the dispersive return pad 450. In the exemplary embodiment, the pad 450 and the probe 400 are coupled together, and are both disposable, single-use items. The pad 450 includes an electrical connector 452 that extends into handle 404 of probe 400 for direct connection to the power supply. Of course, the invention would also be operable with a standard return pad that connects directly to the power supply. In this embodiment, the power supply 460 will include a switch, e.g., a foot pedal 462, for switching between the monopolar and bipolar modes. In the bipolar mode, the return path on the power supply is coupled to return electrode 408 on probe 400, as described above. In the monopolar mode, the return path on the power supply is coupled to connector 452 of pad 450, active electrode(s) 410 are decoupled from the electrical circuit, and return electrode 408 functions as the active electrode. This allows the surgeon to switch between bipolar and monopolar modes during, or prior to, the surgical procedure. In some cases, it may be desirable to operate in the monopolar mode to provide deeper current penetration and, thus, a greater thermal heating of the tissue surrounding the return electrodes. In other cases, such as ablation of tissue, the bipolar modality may be preferable to limit the current penetration to the tissue.

In one configuration, the dispersive return pad 450 is adapted for coupling to an external surface of the patient in a region substantially close to the target site. For example, during the treatment of tissue in the head and neck, the dispersive return pad is designed and constructed for placement in or around the patient's shoulder, upper back or upper chest region. This design limits the current path through the patient's body to the head and neck area, which minimizes the damage that may be generated by unwanted current paths in the patient's body, particularly by limiting current flow through the patient's heart. The return pad is also designed to minimize the current densities at the pad, to thereby minimize patient skin burns in the region where the pad is attached.

Figure 16:
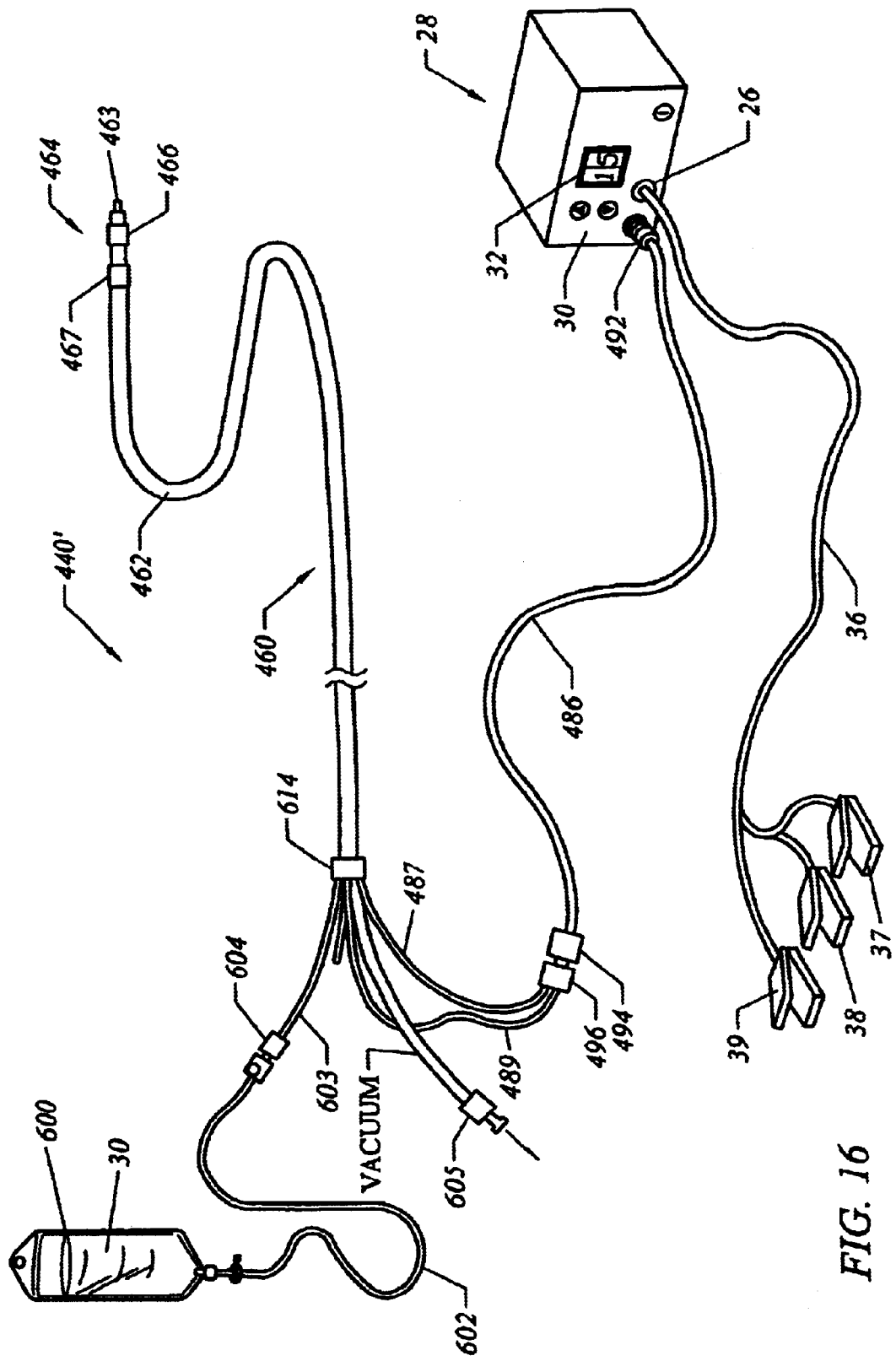
FIG. 16 illustrates a catheter system for electrosurgical treatment of intervertebral discs according to the present invention.
Figure 17:
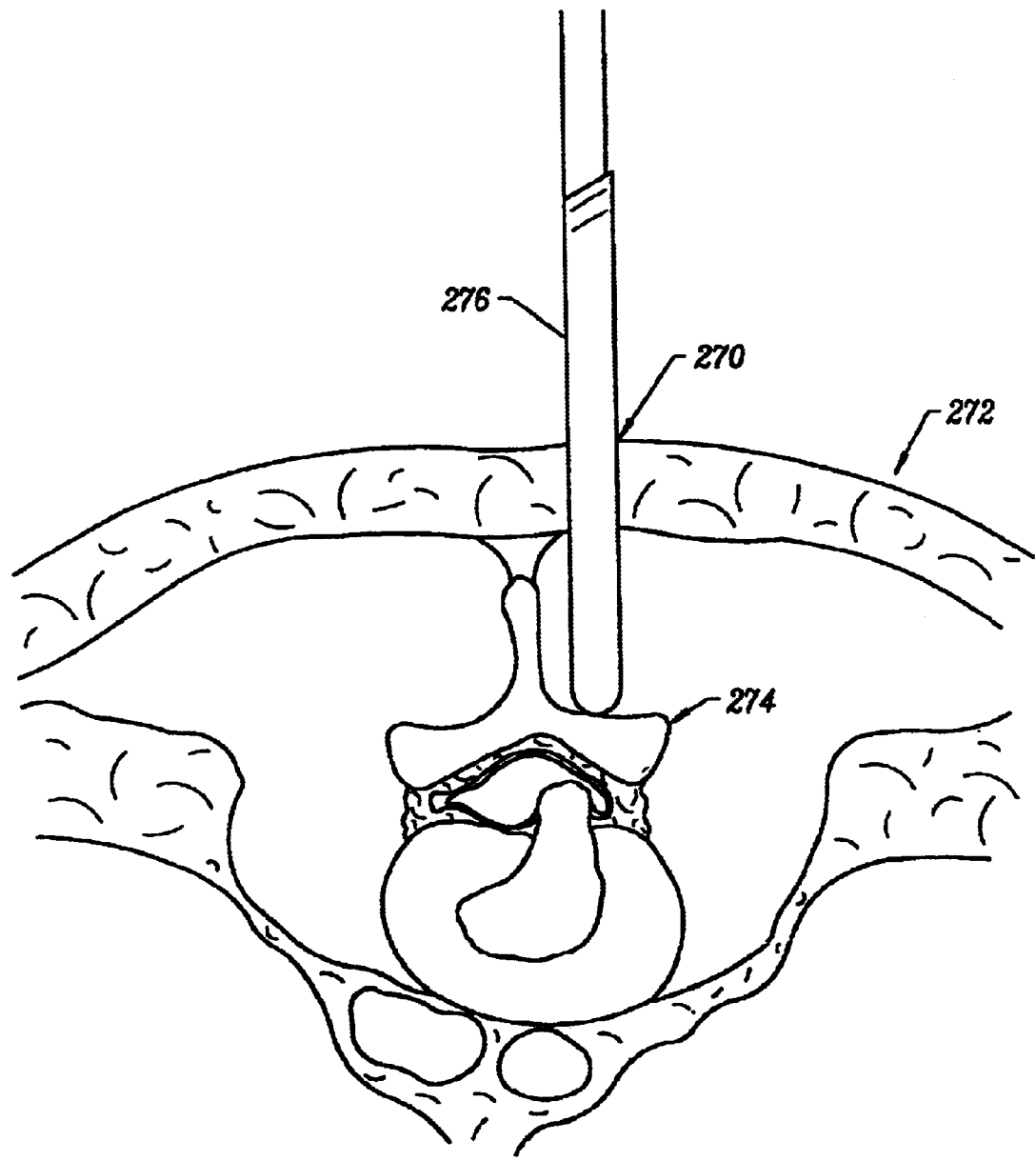
FIGS. 17–21 illustrate a method of performing a microendoscopic discectomy according to the principles of the present invention.

Referring to FIG. 16, the electrosurgical system according to the present invention may also be configured as a catheter system 440'. As shown in FIG. 16, a catheter system 440' generally comprises an electrosurgical catheter 460 connected to a power supply 28 by an interconnecting cable 486 for providing high frequency voltage to a target tissue and an irrigant reservoir or source 600 for providing electrically conductive fluid to the target site. Catheter 460 generally comprises an elongate, flexible shaft body 462 including a tissue removing or ablating region 464 at the distal end of body 462. The proximal portion of catheter 460 includes a multi-lumen fitment 614 which provides for interconnections between lumens and electrical leads within catheter 460 and conduits and cables proximal to fitment 614. By way of example, a catheter electrical connector 496 is removably connected to a distal cable connector 494 which, in turn, is removably connectable to power supply 28 through connector 492. One or more electrically conducting lead wires (not shown) within catheter 460 extend between one or more active electrodes 463 and a coagulation electrode 467 at tissue ablating region 464 and one or more corresponding electrical terminals (also not shown) in catheter connector 496 via active electrode cable branch 487. Similarly, a return electrode 466 at tissue ablating region 464 is coupled to a return electrode cable branch 489 of catheter connector 496 by lead wires (not shown). Of course, a single cable branch (not shown) may be used for both active and return electrodes.

Catheter body 462 may include reinforcing fibers or braids (not shown) in the walls of at least the distal ablation region 464 of body 462 to provide responsive torque control for rotation of active electrodes during tissue engagement. This rigid portion of the catheter body 462 preferably extends only about 7 mm to 10 mm while the remainder of the catheter body 462 is flexible to provide good trackability during advancement and positioning of the electrodes adjacent target tissue.

In some embodiments, conductive fluid 30 is provided to tissue ablation region 464 of catheter 460 via a lumen (not shown in FIG. 16) within catheter 460. Fluid is supplied to lumen from the source along a conductive fluid supply line 602 and a conduit 603, which is coupled to the inner catheter lumen at multi-lumen fitment 614. The source of conductive fluid (e.g., isotonic saline) may be an irrigant pump system (not shown) or a gravity-driven supply, such as an irrigant reservoir 600 positioned several feet above the level of the patient and tissue ablating region 464. A control valve 604 may be positioned at the interface of fluid supply line 602 and conduit 603 to allow manual control of the flow rate of electrically conductive fluid 30. Alternatively, a metering pump or flow regulator may be used to precisely control the flow rate of the conductive fluid.

System 440' can further include an aspiration or vacuum system (not shown) to aspirate liquids and gases from the target site. The aspiration system will usually comprise a source of vacuum coupled to fitment 614 by an aspiration connector 605.

Figure 19:
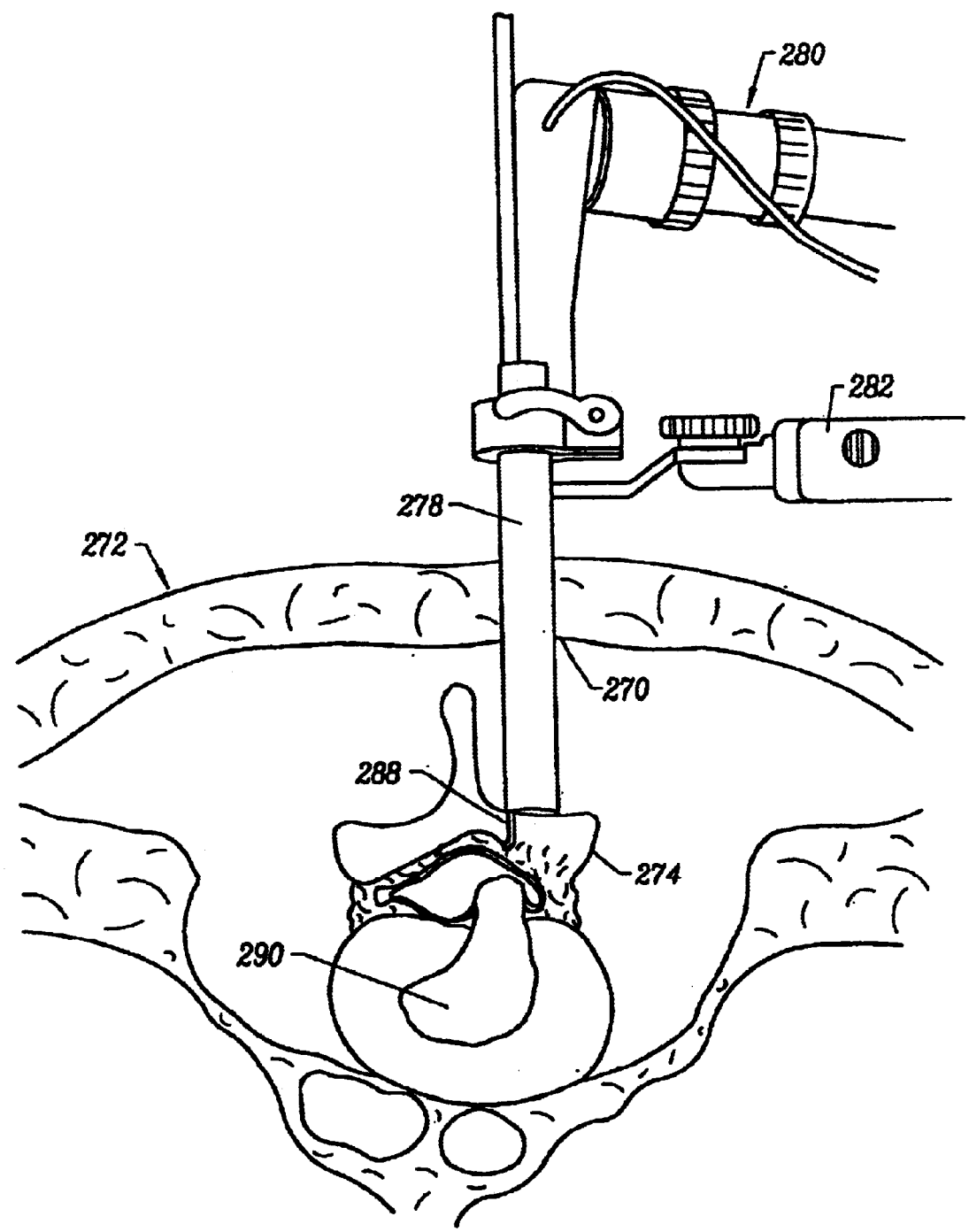
Figure 20:
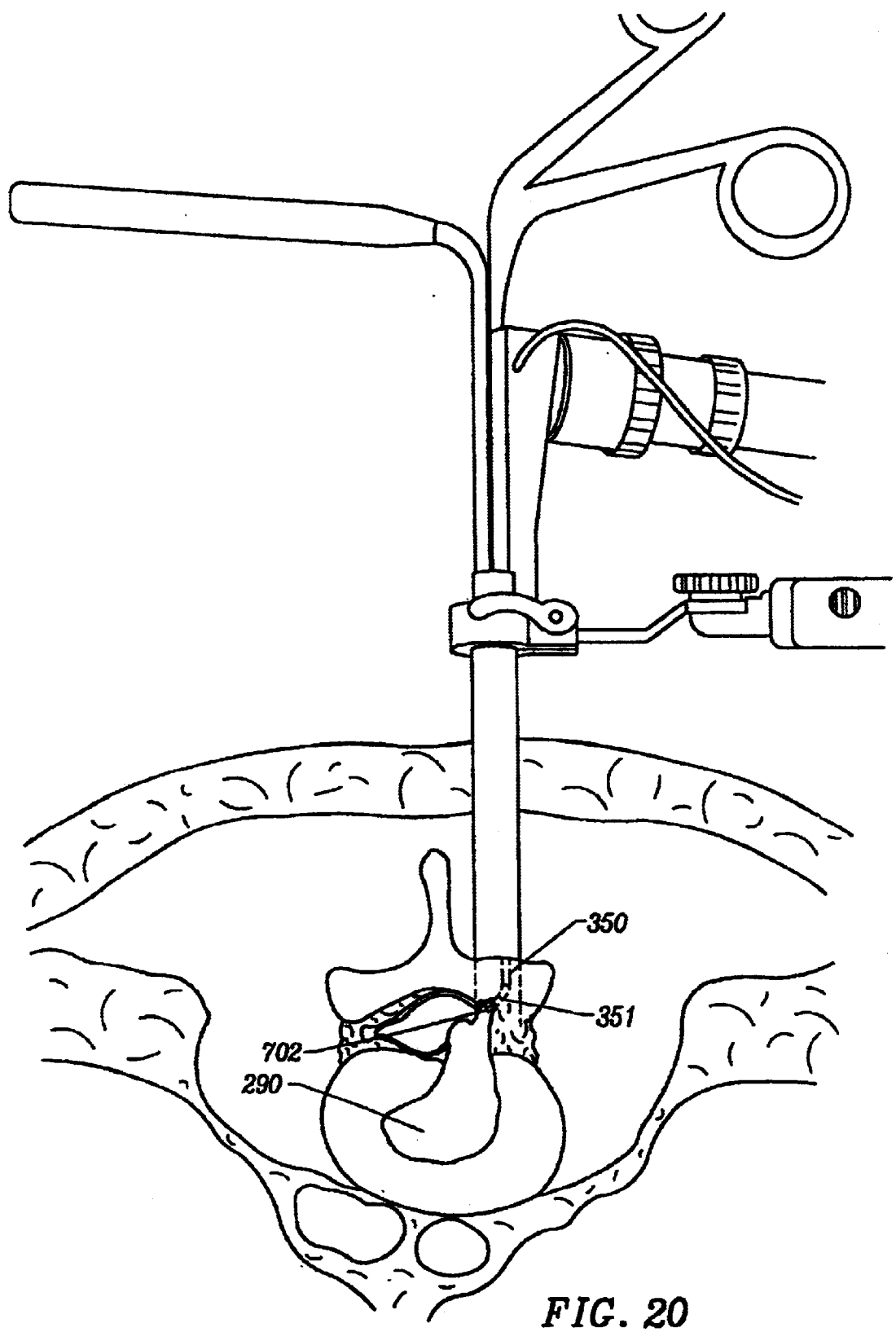

The present invention is particularly useful in microendoscopic discectomy procedures, e.g., for decompressing a nerve root with a lumbar discectomy. FIGS. 17–20 and 23 each schematically represent a section through a vertebra and vertebral disc, wherein the vertebra or disc is being accessed by an electrosurgical instrument of the invention. As shown in FIGS. 17–22, a percutaneous penetration 270 is made in the patients' back 272 so that the superior lamina 274 can be accessed. Typically, a small needle (not shown) is used initially to localize the disc space level, and a guidewire (not shown) is inserted and advanced under lateral fluoroscopy to the inferior edge of the lamina 274. Sequential cannulated dilators 276 are inserted over the guide wire and each other to provide a hole from the incision 220 to the lamina 274. The first dilator may be used to "palpate" the lamina 274, assuring proper location of its tip between the spinous process and facet complex just above the inferior edge of the lamina 274. As shown in FIGS. 19 and 20 a tubular retractor 278 is then passed over the largest dilator down to the lamina 274. The dilators 276 are removed, establishing an operating corridor within the tubular retractor 278.

Figure 18:
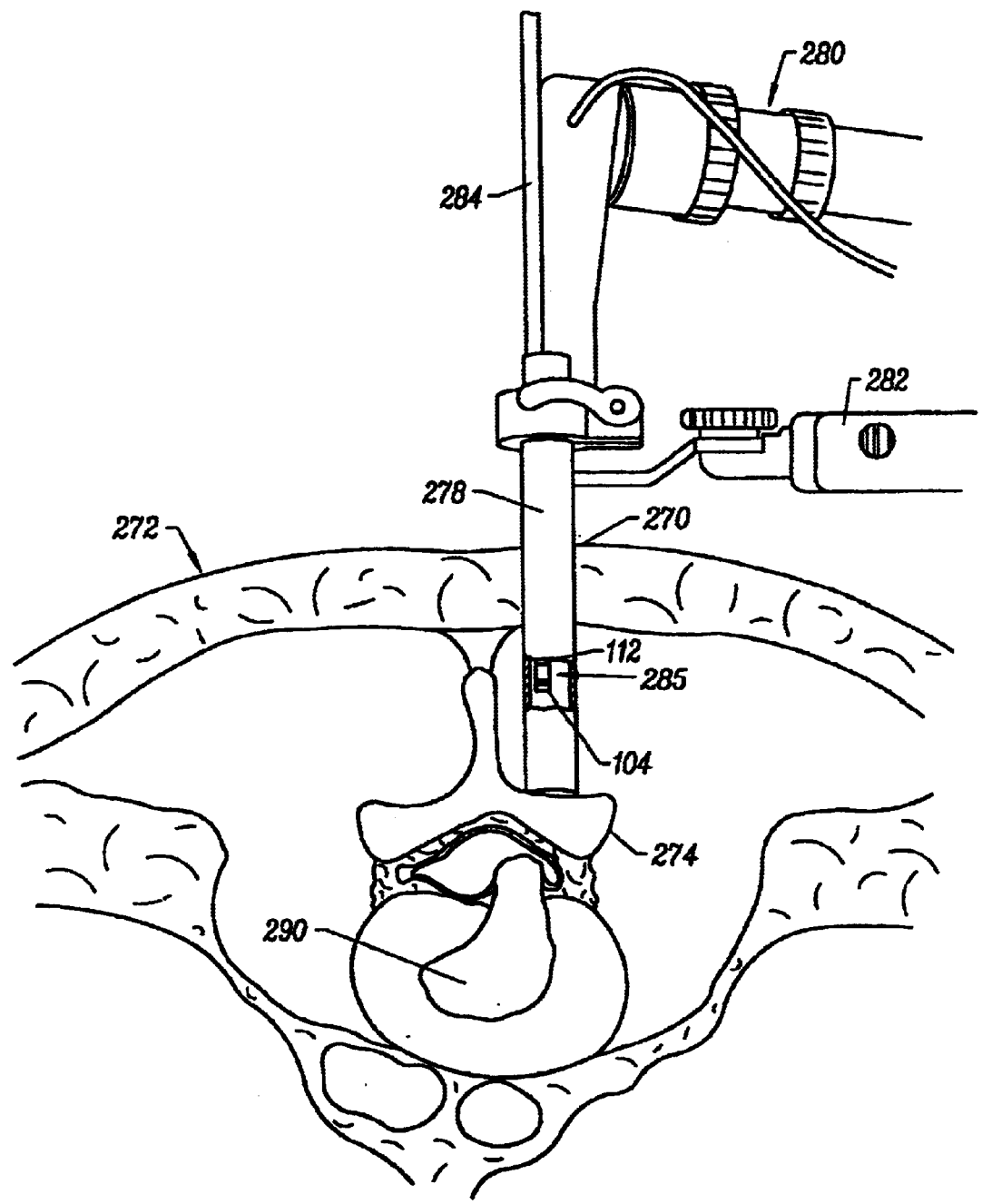

As shown in FIG. 18, an endoscope 280 is then inserted into the tubular retractor 278 and a ring clamp 282 is used to secure the endoscope 280. Typically, the formation of the operating corridor within retractor 278 requires the removal of soft tissue, muscle or other types of tissue that were forced into this corridor as the dilators 276 and retractor 278 were advanced down to the lamina 274. In prior art methods, this tissue is usually removed with mechanical instruments, such as pituitary rongeurs, curettes, graspers, cutters, drills, microdebriders, and the like. Unfortunately, these mechanical instruments greatly lengthen and increase the complexity of the procedure. In addition, these prior art instruments sever blood vessels within this tissue, usually causing profuse bleeding that obstructs the surgeon's view of the target site.

According to another aspect of the present invention, an electrosurgical probe or catheter 284 as described above is introduced into the operating corridor within the retractor 278 to remove the soft tissue, muscle and other obstructions from this corridor so that the surgeon can easily access and visualize the lamina 274. Once the surgeon has introduced the probe 284, electrically conductive fluid 285 can be delivered through tube 233 and opening 237 (see FIG. 2) to the tissue. The fluid flows past the return electrode 112 to the active electrodes 104 at the distal end of the probe shaft. The rate of fluid flow is controlled with valve 17 (FIG. 1) such that the zone between the tissue and electrode support 102 is constantly immersed in fluid 285. The power supply 28 is then turned on and adjusted such that a high frequency voltage difference is applied between active electrodes 104 and return electrode 112. The electrically conductive fluid provides the conduction path (see current flux lines) between active electrodes 104 and the return electrode 112.

The high frequency voltage is sufficient to convert the electrically conductive fluid (not shown) between the target tissue and active electrode(s) 104 into an ionized vapor layer or plasma (not shown). As a result of the applied voltage difference between active electrode(s) 104 and the target tissue (i.e., the voltage gradient across the plasma layer), charged particles in the plasma (e.g., electrons) cause molecular dissociation or disintegration of tissue structures. This molecular dissociation is accompanied by the volumetric removal of tissue and the production of low molecular weight gases, such as oxygen, nitrogen, carbon dioxide, hydrogen and methane.

During the process, the gases will be aspirated through opening 209 and suction tube 211 to a vacuum source. In addition, excess electrically conductive fluid, and other fluids (e.g., blood) will be aspirated from the operating corridor to facilitate the surgeon's view. During ablation of the tissue, the residual heat generated by the current flux lines (typically less than 150° C.), will usually be sufficient to coagulate any severed blood vessels at the site. If not, the surgeon may switch the power supply 28 into the coagulation mode by lowering the voltage to a level below the threshold for fluid vaporization, as discussed above. This simultaneous hemostasis results in less bleeding and facilitates the surgeon's ability to perform the procedure.

Another advantage of the present invention is the ability to precisely ablate soft tissue without causing necrosis or thermal damage to the underlying and surrounding tissues, nerves or bone. In addition, the voltage can be controlled so that the energy directed to the target site is insufficient to ablate the lamina 274 so that the surgeon can literally clean the tissue off the lamina 274, without ablating or otherwise effecting significant damage to the lamina.

Referring now to FIGS. 19 and 20, once the operating corridor is sufficiently cleared, a laminotomy and medial facetectomy is accomplished either with conventional techniques (e.g., Kerrison punch or a high speed drill) or with the electrosurgical probe 284 as discussed above. After the nerve root is identified, retraction can be achieved with a retractor 288, or an instrument of the present invention can be used to precisely ablate at least a portion of the disc. If necessary, epidural veins are cauterized either automatically or with the coagulation mode of the present invention. If an annulotomy is necessary, it can be accomplished with a microknife or the ablation mechanism of the present invention while protecting the nerve root with the retractor 288. The herniated disc 290 is then removed with a pituitary rongeur in a standard fashion, or once again through ablation as described above.

In another embodiment, the present invention involves a channeling technique in which small holes or channels are formed within the disc 290, and thermal energy is applied to the tissue surface immediately surrounding these holes or channels to cause thermal damage to the tissue surface, thereby stiffening and debulking the surrounding tissue structure of the disc. Applicant has discovered that such stiffening of the tissue structure in the disc helps to reduce the pressure applied against the spinal nerves by the disc, thereby relieving back and neck pain.

As shown in FIG. 20, the electrosurgical instrument 350 is introduced to the target site at the disc 290 as described above, or in another percutaneous manner (see FIGS. 22–24 below). The electrode assembly 351 is positioned adjacent to or against the disc surface, and electrically conductive fluid is delivered to the target site, as described above. Alternatively, the conductive fluid is applied to the target site, or the distal end of probe 350 is dipped into conductive fluid, e.g., liquid or gel, prior to introducing the probe 350 into the patient. The power supply 28 is then activated and adjusted such that a high frequency voltage difference is applied to the electrode assembly as described above.

Depending on the procedure, the surgeon may translate or otherwise move the electrodes relative to the target disc tissue to form holes, channels, stripes, divots, craters or the like within the disc. In addition, the surgeon may purposely create some thermal damage within these holes, or channels to form scar tissue that will stiffen and debulk the disc. In one embodiment, the physician axially translates the electrode assembly 351 into the disc tissue as the tissue is volumetrically removed to form one or more holes 392 therein (see also FIG. 21). The holes 392 will typically have a diameter of less than 2 mm, preferably less than 1 mm. In another embodiment (not shown), the physician translates the active electrode across the outer surface of the disc to form one or more channels or troughs. Applicant has found that the present invention can quickly and cleanly create such holes, divots or channels in tissue with the cold ablation technology described herein. A more complete description of methods for forming holes or channels in tissue can be found in U.S. Pat. No. 5,683,366, the complete disclosure of which is incorporated herein by reference for all purposes.

Figure 21:
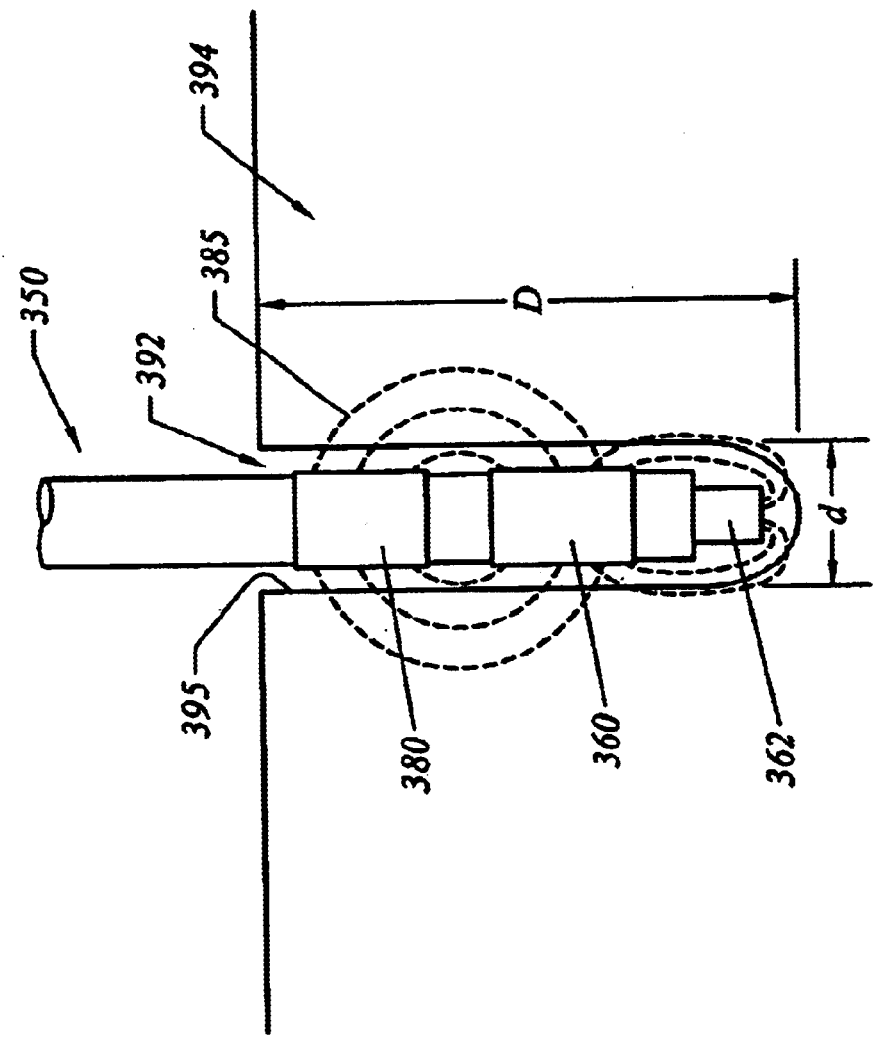

FIG. 21 is a more detailed viewed of the probe 350 of FIG. 14D forming a hole 392 in a disc 290. Hole 392 is preferably formed with the methods described in detail above. Namely, a high frequency voltage difference is applied between active and return electrodes 362, 360, respectively, in the presence of an electrically conductive fluid such that an electric current 361 passes from the active electrode 362, through the conductive fluid, to the return electrode 360. As shown in FIG. 21, this will result in shallow or no current penetration into the disc tissue 394. The fluid may be delivered to the target site, applied directly to the target site, or the distal end of the probe may be dipped into the fluid prior to the procedure. The voltage is sufficient to vaporize the fluid around active electrode 362 to form a plasma with sufficient energy to effect molecular dissociation of the tissue. The distal end of the probe 350 is then axially advanced through the tissue as the tissue is removed by the plasma in front of the probe 350. The holes 392 will typically have a depth D in the range of about 0.5 cm to 2.5 cm, preferably about 1.2 cm to 1.8 cm, and a diameter d of about 0.5 mm to 5 mm, preferably about 1.0 mm to 3.0 mm. The exact diameter will, of course, depend on the diameter of the electrosurgical probe used for the procedure.

During the formation of each hole 392, the conductive fluid between active and return electrodes 362, 360 will generally minimize current flow into the surrounding tissue, thereby minimizing thermal damage to the tissue. Therefore, severed blood vessels on the surface 395 of the hole 392 may not be coagulated as the electrodes 362 advance through the tissue. In addition, in some procedures, it may be desired to thermally damage the surface 395 of the hole 392 to stiffen the tissue. For these reasons, it may be desired in some procedures to increase the thermal damage caused to the tissue surrounding hole 392. In the embodiment shown in FIG. 14D, it may be necessary to either: (1) withdraw the probe 350 slowly from hole 392 after coagulation electrode 380 has at least partially advanced past the outer surface of the disc tissue 394 into the hole 392 (as shown in FIG. 21); or (2) hold the probe 350 within the hole 392 for a period of time, e.g., on the order of 1 seconds to 30 seconds. Once the coagulation electrode is in contact with, or adjacent to, tissue, electric current 385 flows through the tissue surrounding hole 392 and creates thermal damage therein. The coagulation and return electrodes 380, 360 both have relatively large, smooth exposed surfaces to minimize high current densities at their surfaces, which minimizes damage to the surface 395 of hole. Meanwhile, the size and spacing of these electrodes 360, 380 allows for relatively deep current penetration into the tissue 394. In the representative embodiment, the thermal necrosis will extend about 1.0 mm to 5.0 mm from surface 395 of hole 392. In this embodiment, the probe may include one or more temperature sensors (not shown) on probe 350 coupled to one or more temperature displays on the power supply 28 such that the physician is aware of the temperature within the hole 392 during the procedure.

In other embodiments, the physician switches the electrosurgical system from the ablation mode to the subablation or thermal heating mode after the hole 392 has been formed. This is typically accomplished by pressing a switch or foot pedal to reduce the voltage applied to a level below the threshold required for ablation for the particular electrode configuration and the conductive fluid being used in the procedure (as described above). In the subablation mode, the physician will then remove the distal end of the probe 350 from the hole 392. As the probe is withdrawn, high frequency current flows from the active electrodes 362 through the surrounding tissue to the return electrode 360. This current flow heats the tissue and coagulates severed blood vessels at surface 395.

In another embodiment, the electrosurgical probe of the present invention can be used to ablate and/or contract soft tissue within the disc 290 to allow the annulus fibrosus 292 (e.g., FIG. 19) to repair itself to prevent re-occurrence of this procedure. For tissue contraction, a sufficient voltage difference is applied between the active electrodes (e.g., 104) and the return electrode (e.g., 112) to elevate the tissue temperature from normal body temperatures (e.g., 37° C.) to temperatures in the range of 45° C. to 90° C., preferably in the range from 60° C. to 70° C. This temperature elevation causes contraction of the collagen connective fibers within the disc tissue so that the nucleus pulposus withdraws into the annulus fibrosus 292.

In one method of tissue contraction according to the present invention, an electrically conductive fluid is delivered to the target site as described above, and heated to a sufficient temperature to induce contraction or shrinkage of the collagen fibers in the target tissue. The electrically conductive fluid is heated to a temperature sufficient to substantially irreversibly contract the collagen fibers, which generally requires a tissue temperature in the range of about 45° C. to 90° C., usually about 60° C. to 70° C. The fluid is heated by applying high frequency electrical energy to the active electrode(s) in contact with the electrically conductive fluid. The current emanating from the active electrode(s) 104 heats the fluid and generates a jet or plume of heated fluid, which is directed towards the target tissue. The heated fluid elevates the temperature of the collagen sufficiently to cause hydrothermal shrinkage of the collagen fibers. The return electrode 112 draws the electric current away from the tissue site to limit the depth of penetration of the current into the tissue, thereby inhibiting molecular dissociation and breakdown of the collagen tissue and minimizing or completely avoiding damage to surrounding and underlying tissue structures beyond the target tissue site. In an exemplary embodiment, the active electrode(s) 104 are held away from the tissue a sufficient distance such that the RF current does not pass into the tissue at all, but rather passes through the electrically conductive fluid back to the return electrode. In this embodiment, the primary mechanism for imparting energy to the tissue is the heated fluid, rather than the electric current.

In an alternative embodiment, the active electrode(s) 104 are brought into contact with, or close proximity to, the target tissue so that the electric current passes directly into the tissue to a selected depth. In this embodiment, the return electrode draws the electric current away from the tissue site to limit its depth of penetration into the tissue. Applicant has discovered that the depth of current penetration also can be varied with the electrosurgical system of the present invention by changing the frequency of the voltage applied to the active electrode and the return electrode. This is because the electrical impedance of tissue is known to decrease with increasing frequency due to the electrical properties of cell membranes which surround electrically conductive cellular fluid. At lower frequencies (e.g., less than 350 kHz) (corresponding to higher tissue impedance) the presence of the return electrode and the active electrode configuration of the present invention (discussed in detail below) cause the current flux lines to penetrate the tissue less deeply resulting in a smaller depth of tissue heating. In an exemplary embodiment, an operating frequency of about 100 kHz to 200 kHz is applied to the active electrode(s) to obtain shallow depths of collagen shrinkage (e.g., usually less than 1.5 mm and preferably less than 0.5 mm).

In another aspect of the invention, the size (e.g., diameter or principal dimension) of the active electrodes employed for treating the tissue are selected according to the intended depth of tissue treatment. As described previously in copending patent application PCT International Application, U.S. National Phase Serial No. PCT/US94/05168, the depth of current penetration into tissue increases with increasing dimensions of an individual active electrode (assuming other factors remain constant, such as the frequency of the electric current, the return electrode configuration, etc.). The depth of current penetration (which refers to the depth at which the current density is sufficient to effect a change in the tissue, such as collagen shrinkage, irreversible necrosis, etc.) is on the order of the active electrode diameter for the bipolar configuration of the present invention when operating at a frequency of about 100 kHz to about 200 kHz. Accordingly, for applications requiring a smaller depth of current penetration, one or more active electrodes of smaller dimensions would be selected. Conversely, for applications requiring a greater depth of current penetration, one or more active electrodes of larger dimensions would be selected.

Figure 22:
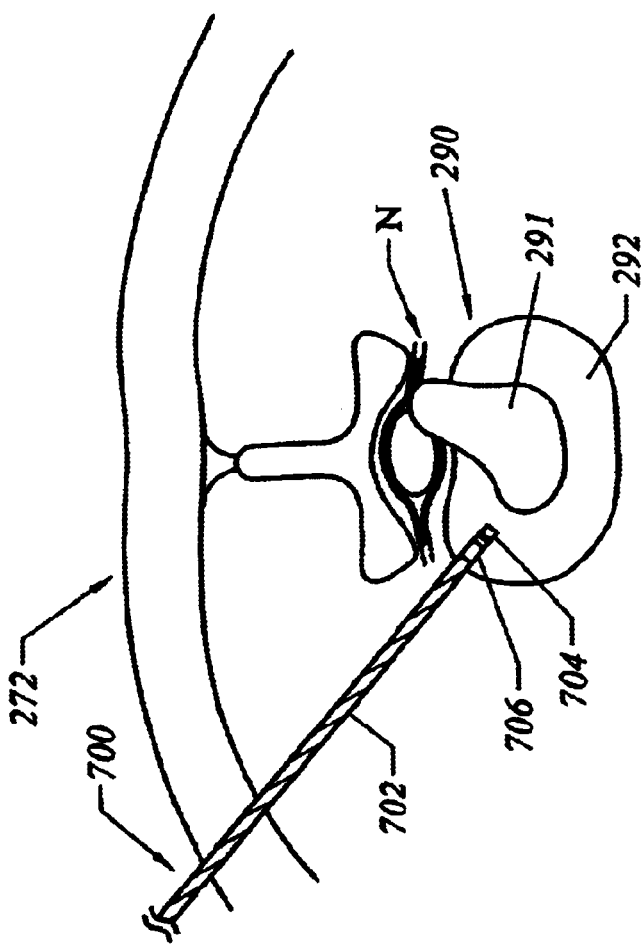
FIGS. 22–24 illustrate another method of treating a spinal disc with one of the catheters or probes of the present invention.
Figure 23:
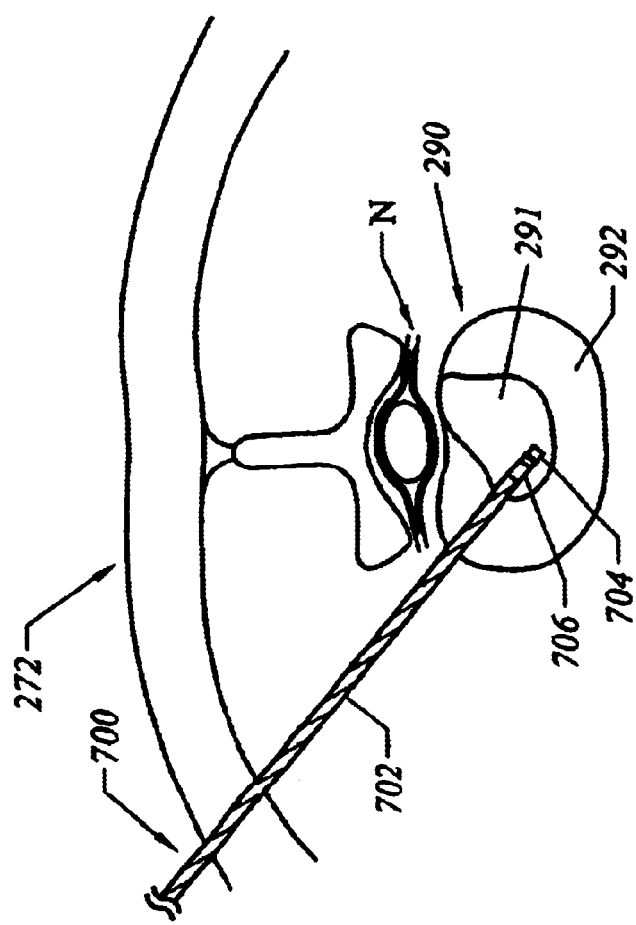
Figure 24:
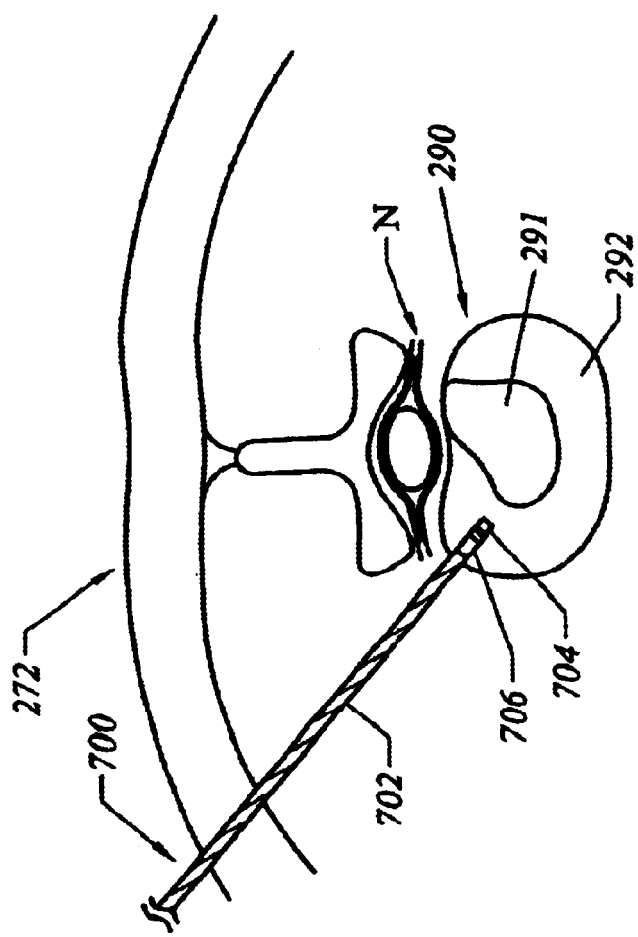

FIGS. 22–24 illustrate another system and method for treating swollen or herniated spinal discs according to the present invention. In this procedure, an electrosurgical probe 700 comprises a long, thin needle-like shaft 702 (e.g., on the order of about 1 mm in diameter or less) that can be percutaneously introduced posteriorly through the patient's back directly into the spine. The shaft 702 may or may not be flexible, depending on the method of access chosen by the physician. The probe shaft 702 will include one or more active electrode(s) 704 for applying electrical energy to tissues within the spine. The probe 700 may include one or more return electrode(s) 706, or the return electrode may be positioned on the patient's back as a dispersive pad (not shown). As discussed below, however, a bipolar design is preferable.

As shown in FIG. 22, the distal portion of shaft 702 is introduced posteriorly through a small percutaneous penetration in the patient's back 272, and advanced into the target vertebral disc 290. To facilitate this process, the distal end of shaft 702 may taper down to a sharper point (e.g., a needle), which can then be retracted to expose active electrode(s) 704. Alternatively, the electrodes may be formed around the surface of the tapered distal portion of shaft 702 (not shown). In either embodiment, the distal end of shaft 702 is delivered through the annulus fibrosus 292 to the target nucleus pulposus 291, which may be herniated, extruded, non-extruded, or simply swollen. As shown in FIG. 23, the distal, working end of shaft 702 may be advanced such that the shaft distal portion bearing active and return electrodes 704, 706 are positioned within nucleus pulposus 291. A high frequency voltage is applied between active electrode(s) 704 and return electrode(s) 706 to heat the surrounding tissue, for example to within a temperature range suitable for contraction of collagen fibers (i.e., typically about 55° C. to about 70° C.). As discussed above, this procedure may alternatively be accomplished with a monopolar configuration. However, applicant has found that the bipolar configuration shown in FIGS. 22–24 provides enhanced control of the high frequency current, which reduces the risk of spinal nerve damage.

As shown in FIGS. 23 and 24, once the nucleus pulposus 291 has been sufficiently contracted to prevent its impingement on a spinal nerve N or nerve root, probe 700 is removed from the target site. In the representative embodiment, the high frequency voltage is applied between active and return electrode(s) 704, 706 while the probe is being withdrawn through annulus fibrosus 292. This applied voltage is sufficient to cause contraction of the collagen fibers within the annulus fibrosus 292, which allows the annulus fibrosus 292 to contract around the hole formed by probe 700, thereby improving the healing of this hole. Thus, the probe 700 seals its own passage as it is withdrawn from the disc.

Figure 25:
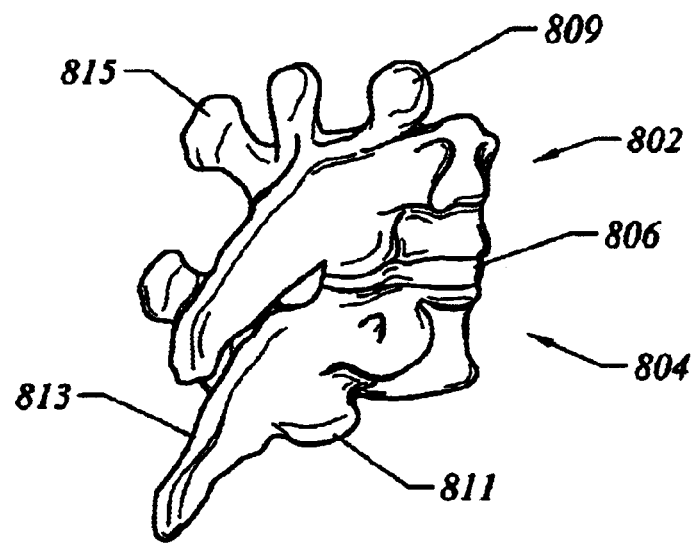
FIG. 25 is a perspective view of two adjacent thoracic vertebrae.

In yet another aspect, the present invention provides systems and methods for treating interspinous tissue within the vertebral column, and more specifically for shrinking ligaments, cartilage, and other tissue between and around adjacent vertebrae 802, 804 and discs 806 (e.g., FIG. 25). The interspinous tissue can be heated, typically with high frequency energy, to shrink and tighten the interspinous tissue and to bring the adjacent vertebral facets and processes closer together so as to provide greater stability to the vertebral column, thereby alleviating symptoms.

Figure 26:
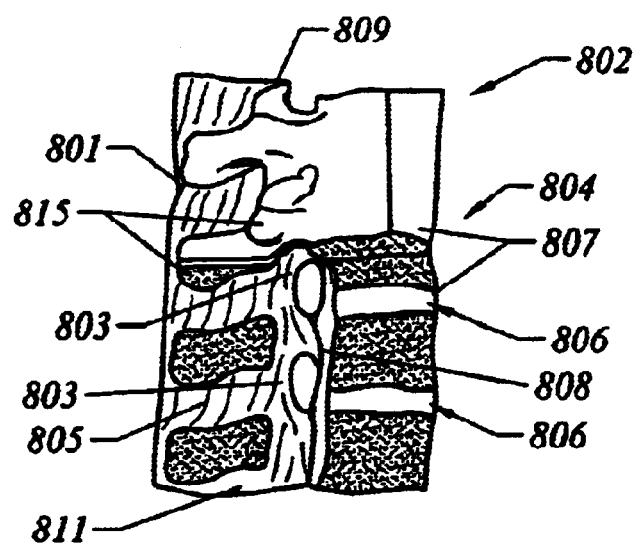
FIG. 26 is a partial cross section of the spinal column which illustrates the general position of some of the interspinous tissue which connects the adjacent vertebrae.

"Interspinous tissue" is used herein to generally mean any tissue that supports and/or surrounds the vertebral column. For example, as shown in FIG. 25 and 26, the interspinous tissue includes the supraspinous ligament 801, ligamentum flavum 803, interspinous ligament 805, anterior longitudinal ligament 807, posterior longitudinal ligament 808, the articular cartilage positioned between the vertebrae 807, articular capsule between the vertebrae (not shown), the capsule surrounding the facet joints, synovial tissue, other tissue adjacent the facets of the superior process 809, inferior process 811, spinous process 813, transverse process 815, and the like.

The systems and methods of the present invention can be used in conjunction with (e.g., before or after) other spinal surgical procedures or can be performed as a separate surgical procedure. For example, after performing any of the above described disc treatments or other conventional or proprietary spinal or disc procedures, an electrosurgical probe can be used to heat and shrink the capsule surrounding one of the facet joints such as the posterior facet joint, thereby tightening the joint, potentially reducing pain, and providing increased stability. Such surgical procedures can be performed either in a minimally invasive or open procedure. In the exemplary embodiments, the same electrosurgical instrument can be used to perform both the disc surgical procedure and the surgical procedure on the interspinous tissue. In other embodiments, however, separate electrosurgical instruments can be used to treat the interspinous tissue and the disc.

High frequency electrical energy is preferably used to treat the interspinous tissue. A sufficient voltage difference is applied between an active electrode(s) 822 and a return electrode 824 (see FIG. 28) to elevate the tissue temperature from normal body temperatures (e.g., 37° C.) to temperatures in the range of 45° C. to 90° C., preferably in the range from 60° C. to 70° C. This temperature elevation causes contraction of the interspinous tissue so that the adjacent vertebrae are drawn closer together, to a more stabilized position. As described above, in the exemplary embodiment the high frequency electrical energy is delivered through a bipolar electrosurgical. The bipolar design has the advantage of minimizing the current flow through non-target tissue including nearby nerves. Accordingly, a return electrode is preferably either integrated with the instrument body, or with another instrument located in close proximity to the instrument body. It should be appreciated however, that the present invention can also use a monopolar dispersive pad, resistive heating, or the like, to heat and shrink the interspinous tissue.

In one method according to the present invention, an electrically conductive fluid is delivered to the target site as described above, and heated to a sufficient temperature to induce contraction or shrinkage of the collagen fibers in the target tissue. The electrically conductive fluid is heated to a temperature sufficient to substantially irreversibly contract the collagen fibers, which generally requires a tissue temperature in the range of about 45° C. to 90° C., usually about 60° C. to 70° C. The fluid is heated by applying high frequency electrical energy to the active electrode(s) in contact with the electrically conductive fluid. The current emanating from the active electrode(s) 822 heats the fluid and generates a jet or plume of heated fluid, which is directed towards the target tissue. The heated fluid elevates the temperature of the collagen sufficiently to cause hydrothermal shrinkage of the collagen fibers. The return electrode 824 draws the electric current away from the tissue site to limit the depth of penetration of the current into the tissue, thereby inhibiting molecular dissociation and breakdown of the collagen tissue and minimizing or completely avoiding damage to surrounding and underlying tissue structures beyond the target tissue site. In an exemplary embodiment, the active electrode(s) 822 are held away from the tissue a sufficient distance such that the RF current does not pass into the tissue at all, but rather passes through the electrically conductive fluid back to the return electrode. In this embodiment, the primary mechanism for imparting energy to the tissue is the heated fluid, rather than the electric current.

In an alternative embodiment, the active electrode(s) 822 are brought into contact with, or close proximity to, the target tissue so that the electric current passes directly into the tissue to a selected depth. In this embodiment, the return electrode draws the electric current away from the tissue site to limit the depth of penetration into the tissue. The return electrode can be either on the same instrument as the active electrodes or on a separate instrument. The depth of current penetration can also be varied with the electrosurgical system of the present invention by changing the frequency of the voltage applied to the active electrode and the return electrode. This is because the electrical impedance of tissue is known to decrease with increasing frequency due to the electrical properties of cell membranes which surround electrically conductive cellular fluid. At lower frequencies (e.g., less than 350 kHz), i.e., at higher tissue impedance, the nature of the return electrode and active electrode configuration of the present invention (discussed in detail hereinabove) causes the current flux lines to penetrate the tissue less deeply resulting in a more shallow depth of tissue heating. In an exemplary embodiment, an operating frequency of about 100 kHz to 200 kHz is applied to the active electrode(s) to obtain shallow depths of collagen shrinkage (e.g., usually less than 1.5 mm and preferably less than 0.5 mm).

Figure 27:
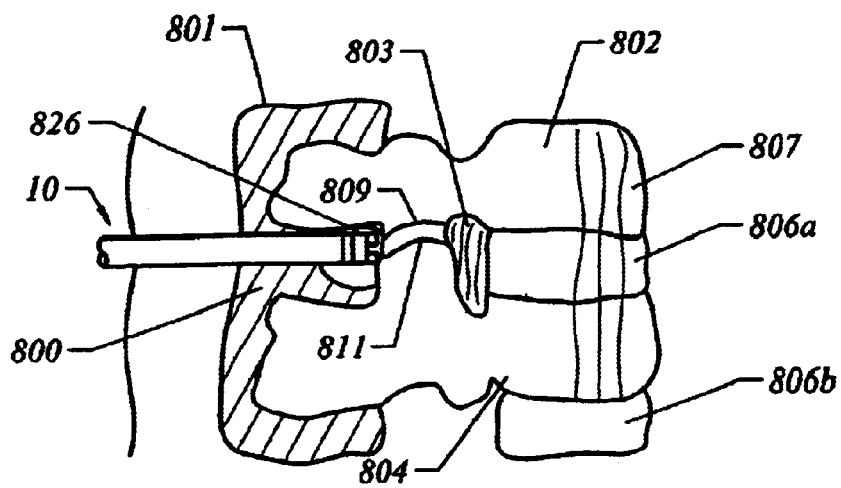
FIG. 27 illustrates positioning an electrosurgical probe adjacent the processes of the vertebrae.
Figure 28:
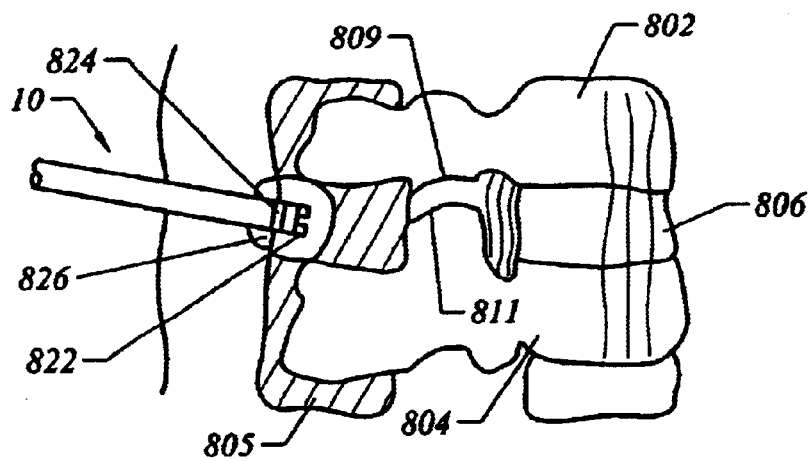
FIG. 28 illustrates heating and shrinking interspinous tissue surrounding the vertebrae.
Figure 29:
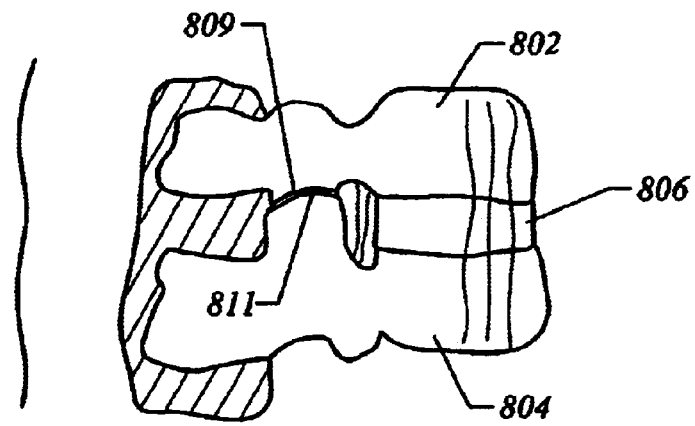
FIG. 29 illustrates the vertebral column after the electrosurgical probe has been removed from the surgical site and the adjacent vertebrae are in a closer configuration.

FIGS. 27 to 29 show an exemplary method of heating and shrinking the interspinous tissue. In use, the electrosurgical instrument typically accesses the spinal column either endoscopically or through an open procedure. As described above, the same electrosurgical instrument or probe 10 can be used to treat one or more defective intervertebral discs or other portions of the spinal column as well as the interspinous tissue. For example in one method, a distal portion of the electrosurgical probe 10 is introduced posteriorly through a small percutaneous penetration 820 into the annulus fibrosus of the target spinal disc 806. After the disc has been treated, the electrosurgical probe 10 is moved adjacent to a target site of the interspinous tissue. As shown in FIG. 27, the active electrode(s) 822 on the distal portion of the shaft of the electrosurgical probe 10 is positioned adjacent the tissue around the processes 809, 811 and a high frequency voltage is applied between the active electrode(s) 822 and a return electrode(s) 824 to heat the interspinous tissue to a suitable temperature for shrinkage (e.g., typically between 45° C. and 90° C.). Optionally, once the tissue has been sufficiently heated, the distal or working end of probe 10 can be repositioned to treat other regions of the interspinous tissue (FIG. 26), which can be subsequently heated and shrunk. Shrinkage of the interspinous tissue can bring the facets in the inferior and superior processes 809, 811 of the adjacent vertebrae 802, 804 to a more stable configuration.

As shown in FIGS. 27 and 28, in some embodiments, an electrically conductive fluid 826 can be placed or delivered to the target site and heated to a sufficient temperature to induce contraction or shrinkage of the collagen fibers in the target tissue. The shrunken interspinous tissue can move the adjacent vertebrae 802, 804 to a closer, more stabilized position. Once the interspinous tissue has been sufficiently contracted, the electrosurgical probe 10 is removed from the target site and the percutaneous opening is closed. As illustrated in FIG. 29, once the interspinous tissue has been treated in the manner described above, the adjacent vertebrae 802, 804 will be in a closer, more stable configuration.

Figure 30:
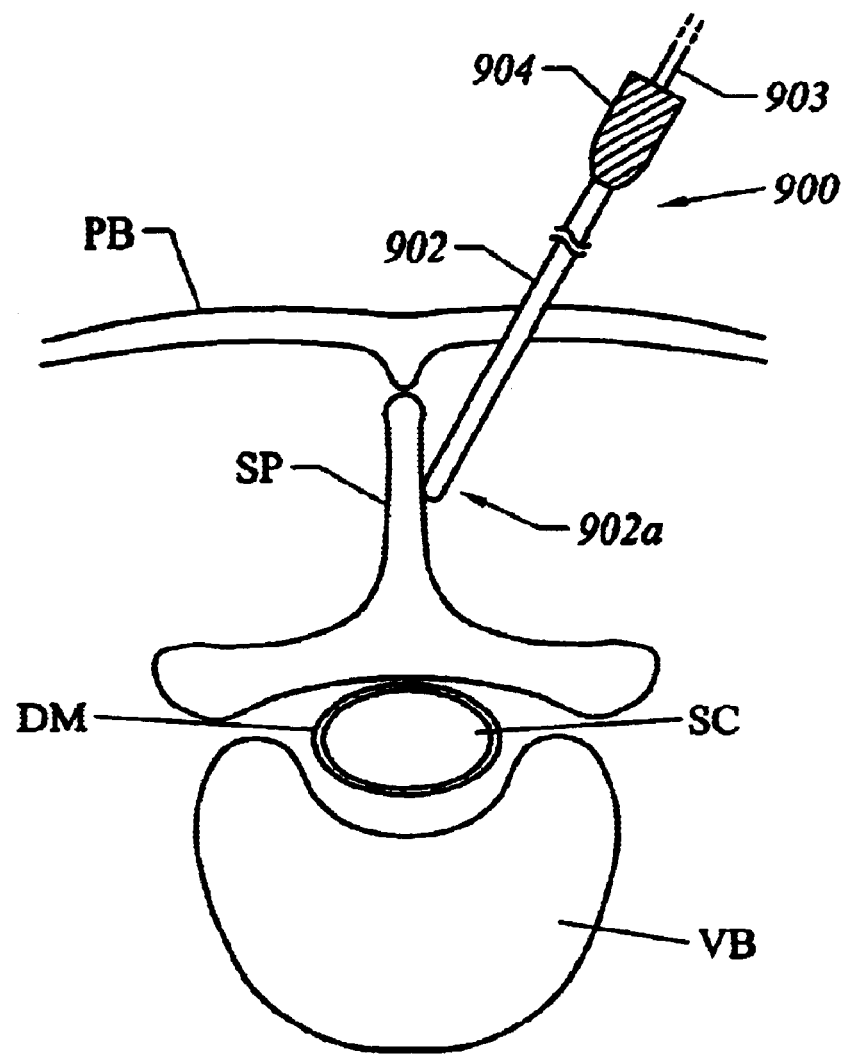
FIG. 30 schematically represents a vertebra, as seen in cross-section, in relation to an electrosurgical probe, according to one embodiment of the invention.

FIG. 30 schematically represents an electrosurgical probe 900 positioned in the vicinity of a spinous process SP of a vertebra, according to one aspect of the invention. Also shown in FIG. 30 is the body VB of the vertebra in relation to the spinal cord SC, and the dura mater DM. Probe 900 includes a handle 904, and a shaft 902 having shaft distal end 902a. Probe 900 typically includes at least one active electrode and at least one return electrode located at shaft distal end 902a (not shown in FIG. 30). Probe 900 is capable of operating in at least the subablation mode to provide thermal heating to tissue in contact with, or in close proximity to, shaft distal end 902a. Probe 900 may also be capable of operating in an ablation mode. For example, probe 900 may have an electrode configuration substantially the same or similar to those described above, for example, with reference to FIGS. 14B–14D. A cable or other connector 903 couples probe 900 to a suitable power supply (e.g., power supply 28, FIG. 1, FIG. 2) for supplying a high frequency voltage between the at least one active electrode and the at least one return electrode, essentially as described hereinabove. Upon application of suitable high frequency voltage between the at least one active electrode and the at least one return electrode of probe 900, the probe operates in the subablation mode to effect controlled thermal heating to a target interspinous tissue. Typically, an electrically conductive fluid is provided at shaft distal end 902a to provide a current flow path between the at least one active electrode and the at least one return electrode. As described hereinabove, thermal heating of the target tissue may be effected indirectly by conductive heat transfer, e.g., heat from the electrode or heating a quantity of electrically conductive fluid located at shaft distal end 902a, or the target tissue may be heated more directly by passing an electric current through at least a portion of the target tissue, or by a combination of these mechanisms. Typically, the target interspinous tissue is heated to a temperature in the range of about 60° and 70° C., thereby causing irreversible shrinkage or contraction of collagen fibers (and perhaps of other components) of the target tissue.

It should be understood that the invention is not limited to the particular position of probe 900 depicted in FIG. 30. Instead, shaft distal end 902a may be positioned in a variety of different tissues in or around the vertebral column, including the interspinous ligament between the spinous process of two adjacent vertebrae. Probe 900 may be conveniently positioned adjacent to interspinous tissue or other target tissue, in a percutaneous procedure using a posterior approach. Introduction and guiding of shaft distal end to targeted interspinous tissue may be facilitated by means of an introducer needle, with or without an extension tube (neither of which are shown in FIG. 30). Moreover, probe 900 may also be used in an electrosurgical disc procedure in which shaft distal end 902a is introduced into an intervertebral disc.

Figure 31:
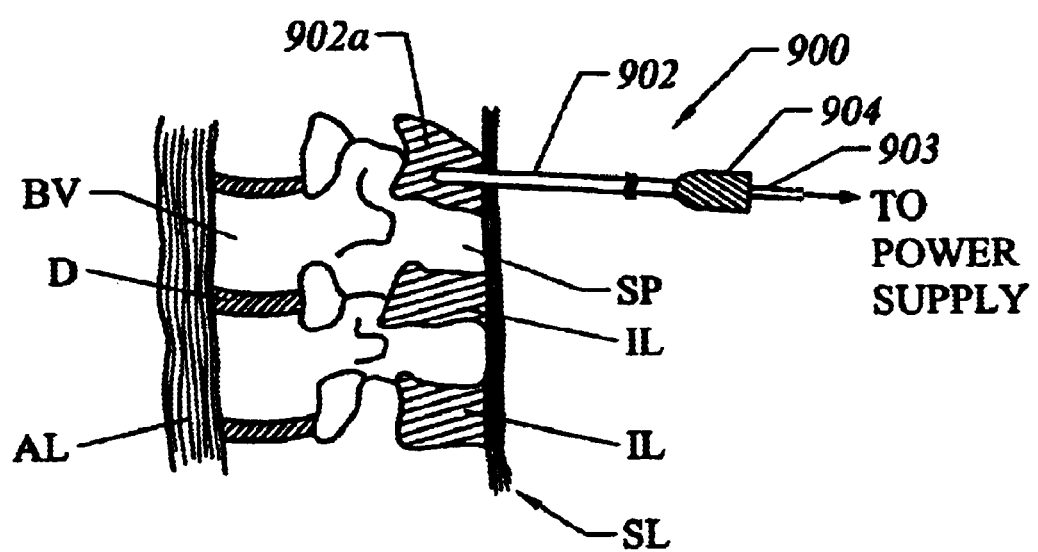
FIG. 31 schematically represents a portion of the vertebral column, as seen in left lateral view, wherein an electrosurgical probe is introduced within interspinous tissue.

FIG. 31 schematically represents a portion of the vertebral column, as seen in left lateral view, and an electrosurgical probe 900 introduced within interspinous tissue. Probe 900 is shown positioned such that shaft distal end 902a is within interspinous ligament, IL. Thus, probe 900 may be used to shrink or contract tissue of interspinous ligament, IL leading to greater stability of the vertebral column. However, as pointed out above (e.g., with reference to FIGS. 27–30) the invention is not limited to a particular position or tissue, but instead shaft distal end 902a may be positioned in a variety of different tissues in or around the vertebral column. Also shown in FIG. 31 are disc D, vertebral body BV, spinous process SP, anterior longitudinal ligament AL, and supraspinous ligament SL.

Figure 32A:
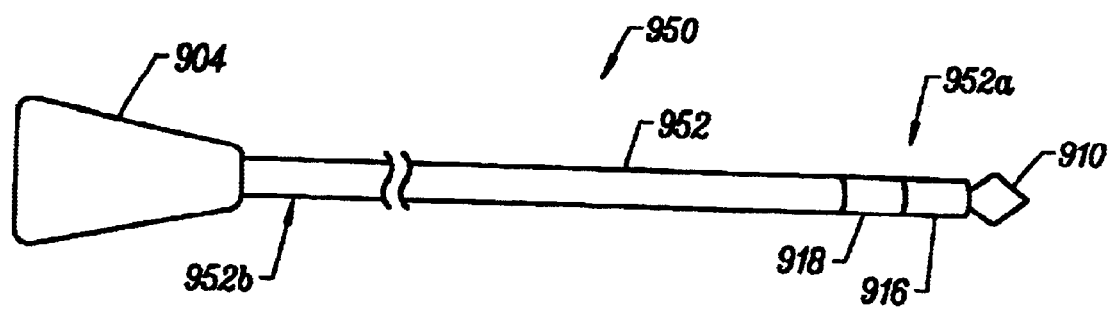
FIG. 32A shows a steerable electrosurgical probe wherein the shaft of the probe assumes a substantially linear configuration.
Figure 32B:
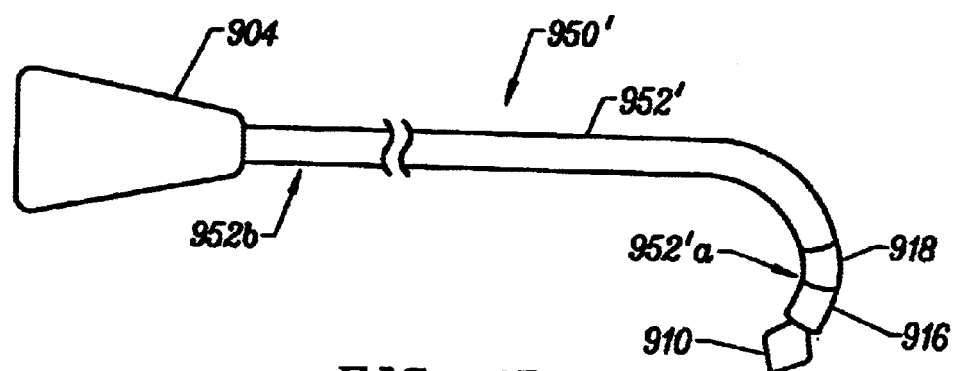
FIG. 32B shows the steerable electrosurgical probe of FIG. 33A, wherein the shaft distal end of the probe adopts a bent configuration.

FIG. 32A shows a steerable electrosurgical probe 950 including a shaft 952, according to another embodiment of the invention. Preferably, shaft 952 is flexible and may assume a substantially linear configuration as shown. Probe 950 includes handle 904, shaft distal end 952a, active electrode 910, insulating collar 916, and return electrode 918. As can be seen in FIG. 32B, under certain circumstances, e.g., upon application of a force to shaft 952 during guiding or steering of probe 950 during a procedure, shaft distal end 952a can adopt a non-linear configuration, designated 952'a. The deformable nature of shaft distal end 952'a allows active electrode 910 to be guided to a specific target site, e.g., within the vertebral column.

Figure 33A:
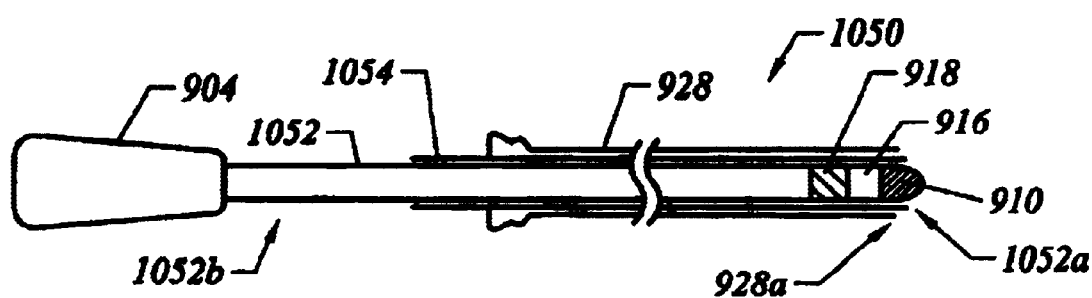
FIG. 33A shows the shaft distal end of an electrosurgical probe positioned within an introducer extension tube and within an introducer needle.

FIG. 33A shows an electrosurgical apparatus or system including a probe 1050 in combination with an introducer needle 928, and an introducer extension tube 1054, according to another aspect of the invention. Probe 1050 generally includes at least one active electrode 910 disposed at a shaft distal end 1052a, an electrically insulating spacer or support 916 proximal to active electrode 910, and a return electrode 918 proximal to support 916. FIG. 33A shows shaft distal end 1052a positioned within introducer extension tube 1054, which is in turn positioned within introducer needle 928. Introducer extension tube 1054 is adapted for passing shaft 1052 therethrough, and for being passed within introducer needle 928. Introducer extension tube 1054 may be advanced distally from introducer distal end 928a to a site targeted for treatment, e.g., to a selected location within an intervertebral disc. In this way, extension tube distal end 1054a (FIG. 61B) may define a starting point for advancement of shaft distal end 1052a into the target tissue, and in some embodiments extension tube distal end 1054a may define a starting point from which guiding or steering of shaft distal end 1052a is initiated. By selecting a starting point from which guiding or steering of shaft distal end 1052a is initiated, much greater control can be exerted over accessing a given target site, and in addition a much greater range of tissue can be accessed with a given probe (e.g., with a probe having a shaft of a given length and curvature).

Figure 33B:
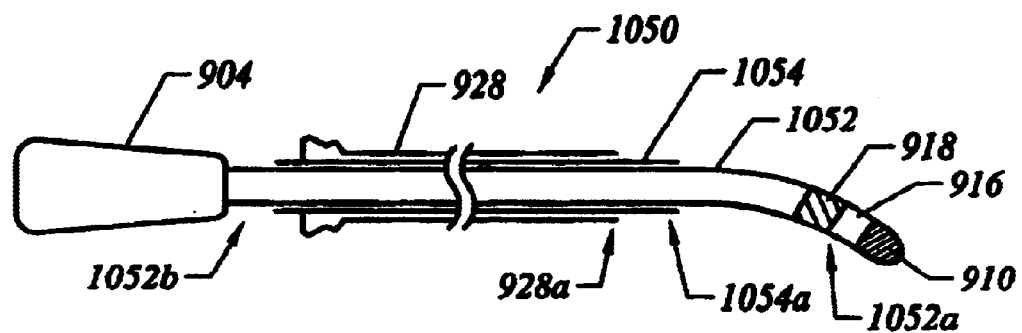
FIG. 33B shows the shaft distal end of the probe of FIG. 33A extending beyond the distal end of both the introducer extension tube and the introducer needle, with the shaft distal end adopting a curved configuration.

FIG. 33B shows shaft distal end 1052a of the probe of FIG. 33A extending beyond the distal end of both introducer extension tube 1054 and introducer needle 928, with shaft distal end 1052a adopting a curved configuration. Such a curved configuration allows access to a much greater number of regions or to a much larger volume of tissue, for example, by rotating shaft 1052. Such a curved configuration may be due to a predefined bend or curve in shaft 1052, or may be the result of a steering mechanism, the latter well known in the art. In the former situation, a pre-defined curvature in shaft 1052 may be restrained or compressed while shaft 1052 is within introducer extension tube 1054 or introducer needle 928. Introducer extension tube 1054 may be rigid or somewhat flexible. In an alternative embodiment, introducer extension tube 1054 may be omitted, and shaft 1052 may be introduced or advanced towards a target site via introducer needle 928 alone.

Figure 34:
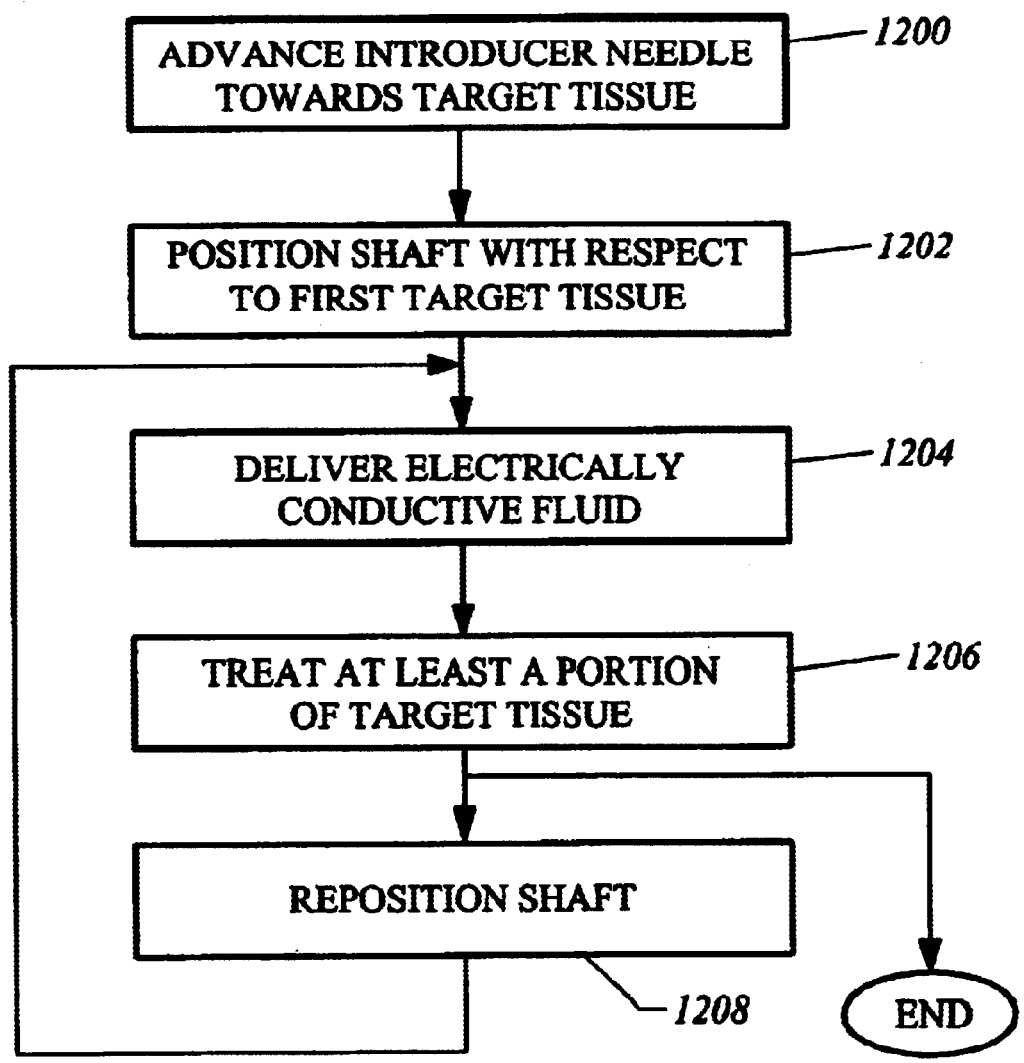
FIG. 34 schematically represents a series of steps involved in a method of treating spinal tissue with an electrosurgical probe according to the present invention.

FIG. 34 schematically represents a series of steps involved in a method of ablating or otherwise treating tissue in or around the vertebral column of a patient using an electrosurgical probe, according to the present invention. Step 1200 involves advancing an introducer needle towards a target tissue to be treated. The introducer needle may be used in combination with an introducer extension tube (FIGS. 33A, 33B). The target tissue may include, for example, a bulging nucleus pulposus of a disc, or various interspinous tissues, as described hereinabove. The introducer needle has a lumen having an internal diameter greater than the external diameter of the shaft distal end of the probe, thereby allowing free passage of the shaft distal end through the lumen of the introducer needle. In one embodiment, the introducer needle preferably has a length in the range of from about 3 cm to about 25 cm, and the lumen of the introducer needle preferably has a diameter in the range of from about 0.5 cm. to about 3.0 mm. The procedure may be performed percutaneously, via a posterior lateral approach. In one embodiment, the introducer needle may have dimensions similar to those of an epidural needle, the latter well known in the art.

Step 1202 involves positioning the shaft of the electrosurgical probe into at least close proximity with the target tissue, e.g., via the introducer needle, wherein the distal end portion of the shaft bears an active electrode and a return electrode. Optional step 1204 calls for introducing an electrically conductive fluid, such as saline, into the disc. Step 1206 involves treating at least a portion of the target tissue by application of a first high frequency voltage between the active electrode and the return electrode. Such treatment may be in the form of ablation or volumetric removal of tissue, coagulation, or shrinkage/contraction of tissue, or a combination thereof, depending on the nature of the target tissue and the particular procedure. Mechanisms for each of these forms of treatment have been described in detail hereinabove. As an example, in a single procedure a portion of the nucleus pulposus of a defective disc may be volumetrically removed with the probe operating in the ablation mode, and an interspinous tissue may be contracted or tightened with the probe operating in a subablation mode. The above and other stages of the procedure may be performed under fluoroscopy to allow visualization of the location of the shaft relative to the target tissue.

After step 1206, one or both of the shaft and introducer needle may be withdrawn from the patient and the procedure terminated. Alternatively, where it is deemed necessary or desirable to treat additional target tissue, the shaft distal end may be repositioned with respect to fresh target tissue, with or without withdrawing the shaft and introducer needle from the patient. For example, to treat a second target tissue which lies close to a previously treated target tissue, the shaft may be repositioned at the second target tissue without withdrawing the introducer needle by axial translation of the shaft or steering of the shaft distal end, or by a combination thereof. Once the shaft distal end is suitably repositioned, steps 1204 and 1206 may be repeated.

The above method may be used for a broad range of treatments in which either volumetric removal of tissue via Coblation® or controlled thermal heating of tissue is indicated, including contained herniations, and excessive spinal mobility. In one embodiment, an introducer needle may be introduced generally as described for step 1200, and a fluoroscopic fluid may be introduced through the lumen of the introducer needle for the purpose of visualizing and diagnosing a disc defect or disorder. Thereafter, depending on the diagnosis, a treatment procedure may be performed, e.g., according to steps 1202 through 1208, using the same introducer needle as access.

It is known in the art that epidural steroid injections can transiently diminish perineural inflammation of an affected nerve root, leading to alleviation of discogenic pain. In one embodiment of the invention, methods for treating tissue in or around the vertebral column described hereinabove may be conveniently performed in conjunction with an epidural steroid injection. For example, epidural injection could be carried out in conjunction with electrosurgical treatment of a disc or interspinous tissue as part of a single procedure, by the same surgeon, using equipment common to both procedures (e.g. visualization equipment). Combining electrosurgical treatment and epidural injection in a single procedure may provide substantial cost-savings as well as a significant improvement in patient care.

Figure 35:
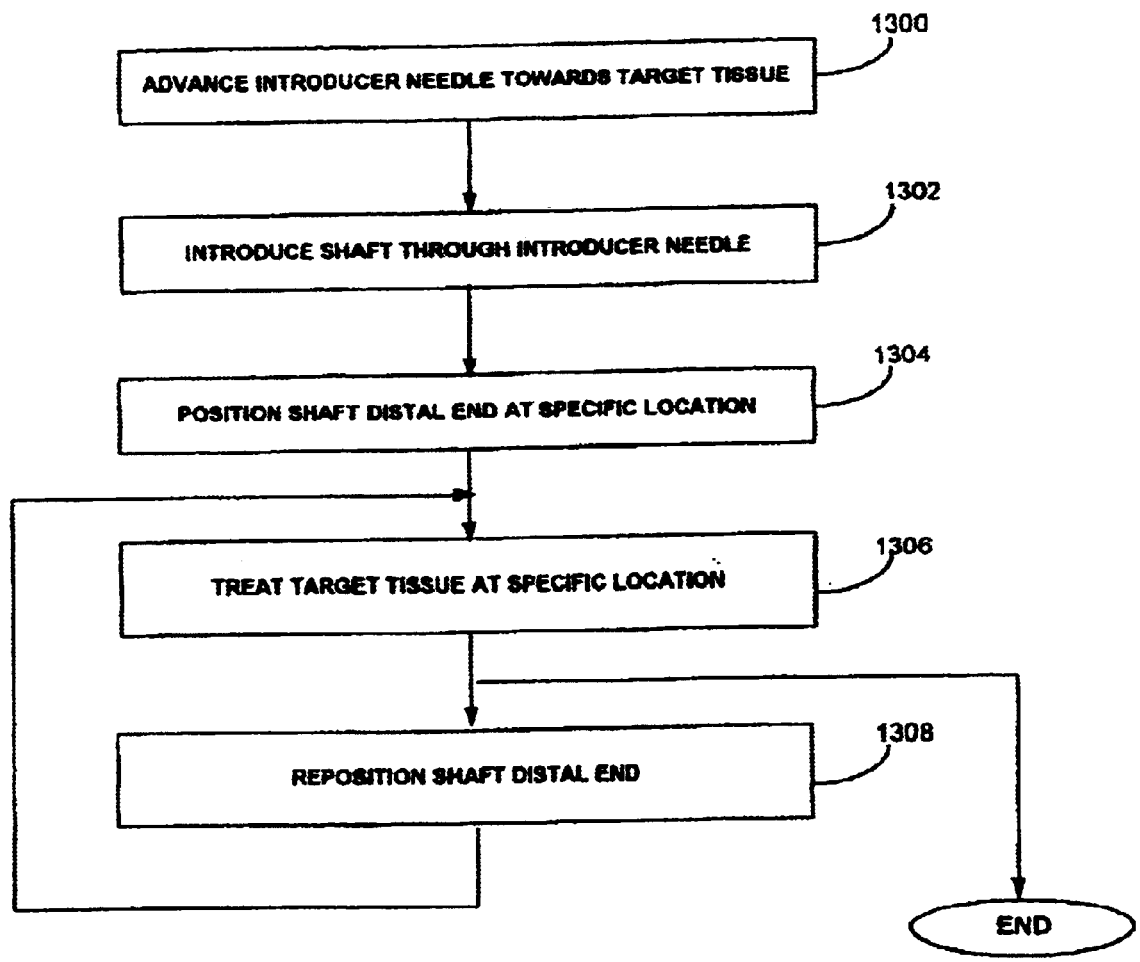
FIG. 35 schematically represents a series of steps involved in a method of treating a target tissue of the vertebral column, according to another embodiment of the invention.

FIG. 35 schematically represents a series of steps involved in a method of treating a target tissue with an electrosurgical probe, according to another embodiment. Such treatment may include, for example, ablation, shrinkage/contraction, or coagulation of tissue in or around the vertebral column. For example, the method may include treatment of specifically targeted disc tissue, or interspinous tissue. Step 1300 of FIG. 35 is analogous to step 1200 of FIG. 34. Thereafter, step 1302 involves introducing the shaft through the lumen of the introducer needle. Step 1304 involves positioning the shaft distal end to a specific location targeted for treatment. For example, the shaft distal end may be guided or steered to the specific location by moving a pre-bent or bendable shaft of the probe. The specific location may be pre-defined as a result of a previous procedure to visualize the defect, e.g., a defect visualized via X-ray examination, endoscopically, or fluoroscopically. In one embodiment, as a prelude to guiding the shaft distal end to a specific location at the target site, the shaft distal end may first be introduced to the general vicinity of the target site, from where the shaft distal end may be guided or steered in order to access the specific location. Guiding the shaft distal end to the specific location may involve advancing or retracting the introducer needle until the introducer needle distal end reaches, or is in close proximity to, the specific location. In another embodiment, the shaft distal end may be introduced at the specific location by advancing or retracting an introducer extension tube (FIGS. 33A, 33B) within the lumen of the introducer needle until the distal end of the introducer extension tube reaches, or is in close proximity to, the specific location.

Guiding the shaft distal end to the defined target site may be performed by axial and/or rotational movement of a curved or bendable shaft. Guiding the shaft distal end may be performed during visualization of the location of the shaft relative to the target site, wherein the visualization may be performed endoscopically or via fluoroscopy. Endoscopic examination may employ a fiber optic cable (not shown). The fiber optic cable may be integral with the electrosurgical probe, or be part of a separate instrument (endoscope). Step 1306 involves treating tissue at the target site, e.g., by shrinking interspinous tissue and/or ablating disc tissue, and is analogous to step 1206 (FIG. 34). Before or during step 1306, an electrically conductive fluid may be applied to the target tissue and/or to the shaft distal end, essentially as for step 1204 (FIG. 34), in order to provide a current flow path between the active and return electrodes located at the shaft distal end portion. After step 1306 has been completed the procedure may be terminated. Alternatively, after the shaft distal end has been guided to a first target site and tissue at that site has been treated, the shaft may be repositioned to access fresh tissue at a second or subsequent target site to be treated (step 1308). Repositioning of the shaft distal end may be performed with or without withdrawing the shaft and introducer needle from the patient, as described herein with reference to FIG. 34. After step 1308, step 1306 may be repeated to treat the tissue at the second or subsequent target site.

Figure 36:
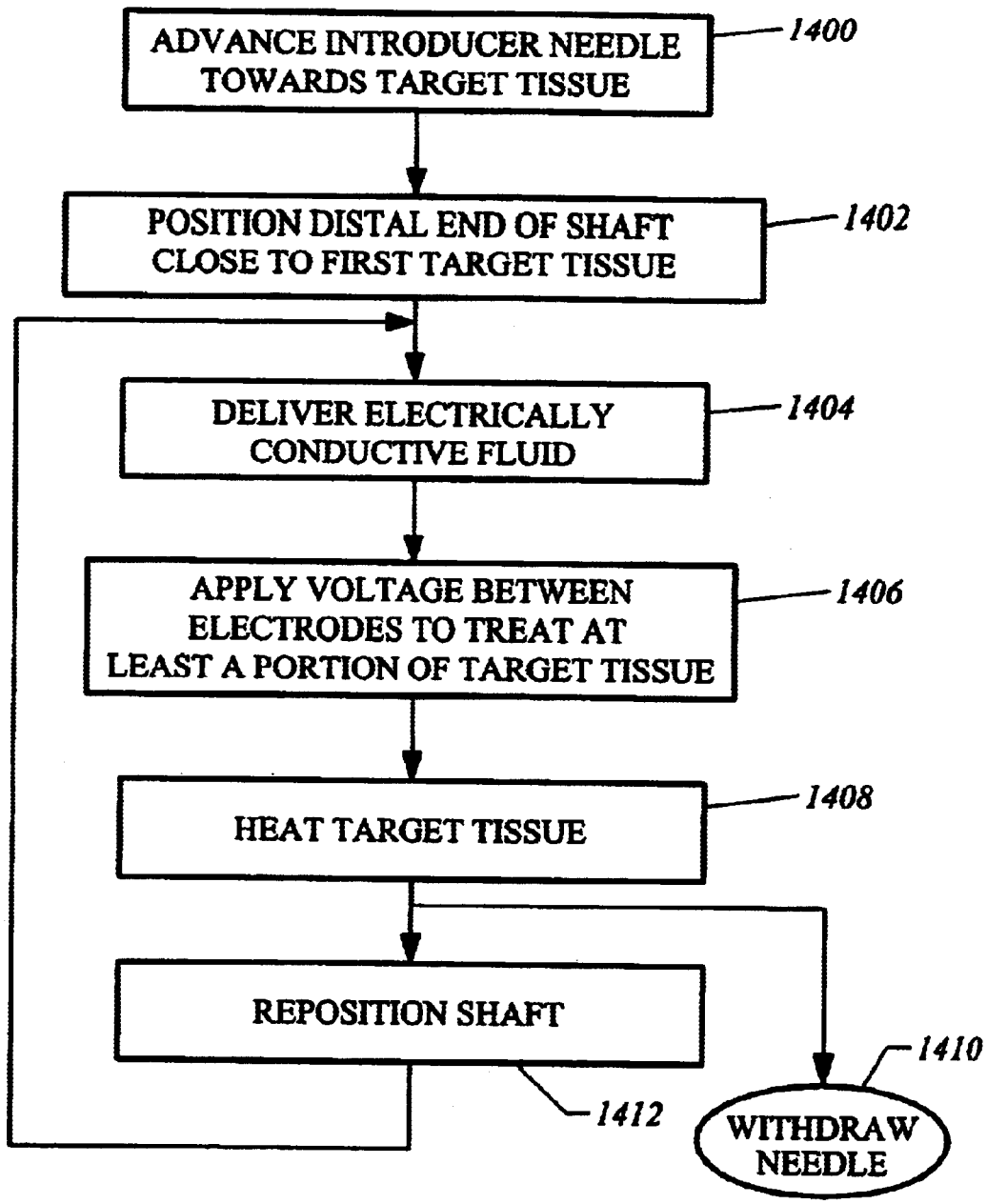
FIG. 36 schematically represents a series of steps involved in a method of treating interspinous tissue, according to another embodiment of the invention.

FIG. 36 schematically represents a series of steps involved in a method of treating interspinous tissue, according to another embodiment of the invention, wherein step 1400 is analogous to step 1200 and/or step 1300 (FIGS. 34 and 35, respectively). Step 1402 involves positioning the shaft of an electrosurgical probe, and in particular the working end (distal end) of the shaft, in contact with or close proximity to the tissue targeted for treatment. Typically, the tissue targeted for treatment comprises one or more interspinous tissues, such as tissues listed hereinabove which surround or are adjacent to various spinous processes or the facet joints of adjacent vertebrae. When such interspinous tissues have become stretched or loose, the patient experiences excessive mobility and decreased stability of the vertebral column.

Typically, the probe includes at least one active electrode and at least one return electrode, both of which are located at the shaft distal end. The probe, in conjunction with a suitable power supply (e.g., power supply 28, FIG. 1, FIG. 2), is adapted for use in at least a subablation mode, in which tissue targeted for treatment undergoes controlled thermal heating, as described hereinabove. Usually, the tissue targeted for treatment is heated in a controlled manner to a temperature within the optimum range for contraction or shrinkage of collagen fibers, i.e., in the range of about 60° to 70° C. The probe may further be adapted for use in one or more additional modes, namely an ablation mode and/or a coagulation mode. A probe used in the method of FIG. 36 may have an electrode array similar to one described hereinabove, for example, with reference to FIGS. 14B–14D.

Optional step 1404 involves delivering an electrically conductive fluid to the shaft distal end or to the target site. As described hereinabove, the electrically conductive fluid may be delivered by a fluid delivery element integral with the probe, or via a separate device. In another embodiment, an electrically conductive fluid, e.g., a gel, may be applied to the shaft distal end prior to introduction of the probe into the patient. Alternatively, the use of an electrically conductive fluid may be eliminated from the procedure.

Step 1406 involves applying a suitable high frequency voltage between the active and return electrodes, so that the probe operates in a subablation mode, wherein the target tissue undergoes thermal heating resulting in shrinkage and/or tightening of the target tissue. Voltage parameters for operating the probe in a thermal heating mode are provided hereinabove. A currently preferred voltage for thermal heating of target interspinous tissue is in the range of about 20 volts RMS to 90 volts RMS. The actual voltage applied may depend on a number of factors (enumerated hereinabove). Upon application of the high frequency voltage between the active and return electrodes, a quantity of an electrically conductive fluid located at the shaft distal end is heated, and the heated fluid causes heating of the target tissue in the proximity of the shaft distal end (step 1408). Alternatively, in some embodiments (e.g., when an electrically conductive fluid is not provided to the shaft distal end) the target tissue may be heated more directly by current flowing from the active electrode into the tissue at the target site. After the tissue at the first target site has been treated to effect shrinkage, contraction, or tightening of the tissue, the probe (and introducer needle) may be withdrawn from the patient (step 1410). In one embodiment, step 1410 signals the termination of the procedure. Alternatively, if is deemed necessary or desirable to treat other target tissue(s), the shaft may be repositioned, with or without withdrawing the probe from the patient, to allow treatment of additional target sites (step 1412). Whether the probe needs to be withdrawn from the patient depends, inter alia, on the location of the subsequent target site(s) relative to the previously treated target site, and the degree to which the shaft distal end can be guided or steered. Once the shaft has been repositioned so as to be in contact with or close proximity to an additional target site, steps 1404 through 1408 may be repeated as necessary. Repositioning the shaft in step 1412 may involve various guiding or steering mechanisms or steps described hereinabove with respect to other aspects and methods of the invention. For example, repositioning the shaft may involve guiding or steering a pre-bent or bendable shaft by means of introducer needles, introducer extension tubes, pull wires, or shape-memory actuators, etc.

While the exemplary embodiments of the present invention have been described in detail, by way of example and for clarity of understanding, a variety of changes, adaptations, and modifications will be obvious to those of skill in the art. Therefore, the scope of the present invention is limited solely by the appended claims.

What is claimed is:

1. A method of treating an interspinous tissue of a patient, comprising:
    a) positioning an active electrode adjacent to a target site of the interspinous tissue, said active electrode is disposed on the distal end of a shaft of an electrosurgical probe;
    b) heating the interspinous tissue at the target site with the active electrode by applying a high frequency voltage between the active electrode and a return electrode, the heating being sufficient to shrink at least a portion of the interspinous tissue; and
    wherein the electrosurgical probe is coupled to a high frequency power supply to provide a power supply/probe combination, the power supply/probe combination configured to operate in either an ablation mode wherein a first high frequency voltage is applied between the active electrode and the return electrode sufficient to effect molecular dissociation of the interspinous tissue, or in a subablation mode wherein a second high frequency voltage applied between the active electrode and the return electrode effects thermal heating and shrinkage of the interspinous tissue.

2. The method of claim 1 wherein the return electrode is disposed on the shaft distal end at a location proximal to the active electrode such that current is induced to flow from the active electrode away from the interspinous tissue.

3. The method of claim 1 wherein the high frequency voltage applied between the active and return electrodes is insufficient to cause ablation of tissue.

4. The method of claim 1 further comprising:
    c) providing a quantity of an electrically conductive fluid around the active electrode, wherein the electrically conductive fluid provides a current flow path between the active electrode and the return electrode.

5. The method of claim 4 wherein applying a high frequency voltage between the active electrode and the return electrode heats the quantity of electrically conductive fluid, and the heated electrically conductive fluid heats the interspinous tissue at the target site.

6. The method of claim 4 wherein said step c) comprises delivering the electrically conductive fluid to the shaft distal end, and said step c) is performed after the positioning step and prior to the applying step.

7. The method of claim 4 wherein the electrically conductive fluid comprises a gel, a liquid, or a gas.

8. The method of claim 1 wherein said step b) comprises heating the interspinous tissue in a controlled manner such that tissue at the target site is exposed to a temperature in the range of from about 60° to 70° C.

9. The method of claim 1 wherein said step b) causes shrinkage of collagen fibers of the interspinous tissue and increased rigidity of the vertebral column of the patient.

10. The method of claim 1 wherein the interspinous tissue is a ligament.

11. The method of claim 10 wherein the ligament is an anterior longitudinal ligament, a posterior longitudinal ligament, a supraspinous ligament, a ligamentum flavum, or an interspinous ligament.

12. The method of claim 1 wherein the interspinous tissue comprises cartilage or a capsule surrounding a facet joint between adjacent vertebrae.

13. The method of claim 1 wherein the interspinous tissue is located adjacent to a spinous processes.

14. The method of claim 1 wherein said step b) causes adjacent spinous processes to be drawn closer together.

15. The method of claim 1 wherein said step b) causes tightening of at least one facet joint between adjacent vertebrae.

16. The method of claim 1 further comprising:
    d) prior to said step a) or after said step b), introducing the shaft distal end into an intervertebral disc; and
    e) after said step d), applying high frequency voltage between the active electrode and the return electrode sufficient to treat the intervertebral disc.

17. The method of claim 16, wherein said step e) comprises applying a high frequency voltage between the active electrode and the return electrode sufficient to ablate or contract a nucleus pulposus of the intervertebral disc.

18. The method of claim 1 wherein the high frequency voltage is in the range of from about 20 volts RMS to 90 volts RMS.

19. The method of claim 1 wherein said step b) comprises controlled heating of the interspinous tissue to within a specific temperature range and to a defined depth of the interspinous tissue at the target site.

20. The method of claim 1 wherein said step b) comprises heating the interspinous tissue at the target site to a depth in the range of from about 0.2 mm to 2.5 mm.

21. The method of claim 1 wherein said step b) comprises applying a high frequency voltage between the active electrode and a return electrode such that an electric current flows through at least a portion of the interspinous tissue at the target site.

22. The method of claim 1, further comprising: advancing an introducer needle towards the target site.

23. The method of claim 1 wherein said step a) comprises advancing a shaft of an electrosurgical probe through an introducer needle.

24. The method of claim 23 wherein said step a) is performed percutaneously.

25. The method of claim 1 wherein said step a) comprises advancing a shaft of an electrosurgical probe through an introducer extension tube.

26. A method of treating a target tissue of the vertebral column of a patient, comprising:
    positioning an active electrode adjacent to the target tissue, wherein said active electrode is disposed on a shaft distal end of an electrosurgical probe;
    applying a first high frequency voltage between the active electrode and a return electrode, wherein the target tissue undergoes controlled thermal heating to a temperature in the range of from about 45° to 90° C. such that at least a portion of the target tissue is shrunk, whereby the vertebral column is substantially stabilized; and
    prior to the positioning step or after the applying step, introducing said shaft distal end into an intervertebral disc; and after the introducing step, applying a second high frequency voltage between the active electrode and the return electrode sufficient to treat the intervertebral disc.

27. The method of claim 2, wherein the active electrode and the return electrode are disposed on the shaft distal end of the electrosurgical probe, the return electrode spaced from the active electrode; the method further comprises providing an electrically conductive fluid between the active electrode and the return electrode, and the electrically conductive fluid is heated by applying the first high frequency voltage between the active electrode and the return electrode.

28. The method of claim 27, wherein applying the first high frequency voltage between the active electrode and the return electrode generates a plume of heated fluid which is directed towards the target tissue.

29. The method of claim 27 wherein the heated fluid elevates the temperature of the target tissue sufficiently to cause hydrothermal shrinkage of collagen fibers within the target tissue.

30. The method of claim 26 wherein applying the first high frequency voltage effects controlled thermal heating of the target tissue to a depth in the range of from about 0.2 to 5.0 mm.

31. The method of claim 26, wherein applying the first high frequency voltage effects heating of the target tissue to a temperature in the range of from about 60° to 70° C.

32. The method of claim 26, wherein the target tissue comprises interspinous tissue, and the controlled thermal heating is sufficient to irreversibly shrink and stiffen the interspinous tissue, whereby at least one joint between adjacent vertebrae of the vertebral column is stabilized.

33. The method of claim 32, wherein the interspinous tissue comprises an interspinous ligament.

34. The method of claim 26, wherein the first high frequency voltage is in the range of from about 20 volts RMS to 90 volts RMS.

35. A method of treating an interspinous tissue of a patient, comprising:
positioning an active electrode adjacent to a target site of the interspinous tissue wherein the active electrode is disposed on the distal end of a shaft of an electrosurgical probe; and
heating the interspinous tissue at the target site by applying a first high frequency voltage between the active electrode and a return electrode, the heating being sufficient to shrink at least a portion of the interspinous tissue
prior to the positioning step or after the heating step, introducing the shaft distal end into an intervertebral disc; and
after the introducing step, applying a second high frequency voltage between the active electrode and the return electrode sufficient to treat the intervertebral disc.

36. The method of claim 35 wherein the return electrode is disposed on the shaft distal end at a location proximal to the active electrode such that current is induced to flow from the active electrode away from the interspinous tissue.

37. The method of claim 35 wherein the first high frequency voltage applied between the active and return electrodes is insufficient to cause ablation of tissue.

38. The method of claim 35 further comprising:
providing a quantity of an electrically conductive fluid around the active electrode, wherein the electrically conductive fluid provides a current flow path between the active electrode and the return electrode.

39. The method of claim 38 wherein applying a first high frequency voltage between the active electrode and the return electrode heats the quantity of electrically conductive fluid, and the heated electrically conductive fluid heats the interspinous tissue at the target site.

40. The method of claim 38 wherein providing the quantity of electrically conductive fluid comprises delivering the electrically conductive fluid to the shaft distal end, and the providing step is performed after the positioning step and prior to the applying a first high frequency voltage step.

41. The method of claim 35 wherein the heating step comprises heating the interspinous tissue in a controlled manner such that tissue at the target site is exposed to a temperature in the range of from about 60° to 70° C.

42. The method of claim 35 wherein the heating step causes shrinkage of collagen fibers of the interspinous tissue and increased rigidity of the vertebral column of the patient.

43. The method of claim 35 wherein the interspinous tissue is a ligament.

44. The method of claim 43 wherein the ligament is an anterior longitudinal ligament, a posterior longitudinal ligament, a supraspinous ligament, a ligamentum flavum, or an interspinous ligament.

45. The method of claim 35 wherein the interspinous tissue comprises cartilage or a capsule surrounding a facet joint between adjacent vertebrae.

46. The method of claim 35 wherein the interspinous tissue is located adjacent to a spinous processes.

47. The method of claim 35 wherein the heating step causes adjacent spinous processes to be drawn closer together.

48. The method of claim 35 wherein the heating step causes tightening of at least one facet joint between adjacent vertebrae.

49. The method of claim 35, wherein applying the second high frequency voltage is sufficient to ablate or contract a nucleus pulposus of the intervertebral disc.

50. The method of claim 38 wherein the electrically conductive fluid comprises a gel, a liquid, or a gas.

51. The method of claim 35 wherein the first high frequency voltage is in the range of from about 20 volts RMS to 90 volts RMS.

52. The method of claim 35 wherein the heating step comprises controlled heating of the interspinous tissue to within a specific temperature range and to a defined depth of the interspinous tissue at the target site.

53. The method of claim 35 wherein said heating step comprises heating the interspinous tissue at the target site to a depth in the range of from about 0.2 mm to 2.5 mm.

54. The method of claim 35 wherein the heating step is carried out such that an electric current flows through at least a portion of the interspinous tissue at the target site.

55. The method of claim 35 wherein the positioning step comprises advancing said shaft of an electrosurgical probe through an introducer needle.

56. The method of claim 35 wherein the positioning step comprises advancing said shaft of an electrosurgical probe through an introducer extension tube.

57. The method of claim 55 wherein the positioning step is performed percutaneously.

58. The method of claim 35 wherein said introducing step is performed prior to said positioning step.

59. The method of claim 35 wherein said introducing step is performed subsequent to said positioning step.

* * * * *